United States Patent
Dillard et al.

(10) Patent No.: US 9,045,500 B2
(45) Date of Patent: Jun. 2, 2015

(54) INHIBITORS OF BETA-SECRETASE

(71) Applicant: Vitae Pharmaceuticals, Inc., Fort Washington, PA (US)

(72) Inventors: Lawrence Wayne Dillard, Yardley, PA (US); Jing Yuan, Lansdale, PA (US); Katerina Leftheris, San Diego, CA (US); Shankar Venkatraman, Lansdale, PA (US); Guosheng Wu, Yardley, PA (US); Lanqi Jia, Horsham, PA (US); Zhenrong Xu, Chalfont, PA (US); Salvacion Cacatian, Conshohocken, PA (US); Angel Morales-Ramos, Blue Bell, PA (US); Suresh B. Singh, Kendall Park, NJ (US); Yajun Zheng, Hockessin, DE (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

(21) Appl. No.: 14/509,498

(22) Filed: Oct. 8, 2014

(65) Prior Publication Data

US 2015/0031691 A1 Jan. 29, 2015

Related U.S. Application Data

(62) Division of application No. 13/575,679, filed as application No. PCT/US2011/025912 on Feb. 23, 2011, now Pat. No. 8,889,703.

(60) Provisional application No. 61/307,625, filed on Feb. 24, 2010.

(51) Int. Cl.
| | |
|---|---|
| *C07D 471/04* | (2006.01) |
| *C07D 491/107* | (2006.01) |
| *C07D 209/54* | (2006.01) |
| *C07D 487/04* | (2006.01) |
| *A61K 31/5395* | (2006.01) |
| *A61K 31/519* | (2006.01) |
| *C07D 513/04* | (2006.01) |
| *C07D 498/04* | (2006.01) |

(52) U.S. Cl.
CPC ............ *C07D 513/04* (2013.01); *C07D 498/04* (2013.01); *C07D 487/04* (2013.01); *C07D 471/04* (2013.01); *C07D 491/107* (2013.01); *C07D 209/54* (2013.01)

(58) Field of Classification Search
USPC ........................................ 544/230; 514/259.1
See application file for complete search history.

(56) References Cited

U.S. PATENT DOCUMENTS

| | | | |
|---|---|---|---|
| 4,874,869 A | 10/1989 | Ueda et al. | |
| 5,430,048 A | 7/1995 | Gadwood | |
| 7,423,158 B2 | 9/2008 | Malamas et al. | |
| 7,607,246 B2 | 10/2009 | Valiyambath Krishnan et al. | |
| 7,872,009 B2 | 1/2011 | Albrecht et al. | |
| 8,426,447 B2 | 4/2013 | White et al. | |
| 8,450,308 B2 | 5/2013 | Dillard et al. | |
| 8,633,212 B2 | 1/2014 | Cacatian et al. | |
| 2005/0282825 A1 | 12/2005 | Malamas et al. | |
| 2005/0282826 A1 | 12/2005 | Malamas et al. | |
| 2006/0111370 A1 | 5/2006 | Zhu et al. | |
| 2006/0281730 A1 | 12/2006 | Zhu et al. | |
| 2006/0287294 A1 | 12/2006 | Zhu et al. | |
| 2007/0004730 A1 | 1/2007 | Zhou et al. | |
| 2007/0004786 A1 | 1/2007 | Malamas et al. | |
| 2007/0027199 A1 | 2/2007 | Malamas et al. | |
| 2007/0072925 A1 | 3/2007 | Malamas et al. | |
| 2007/0203116 A1 | 8/2007 | Quagliato et al. | |
| 2007/0287692 A1 | 12/2007 | Wu et al. | |
| 2009/0209529 A1 | 8/2009 | Andreini et al. | |
| 2011/0152253 A1 | 6/2011 | Motoki et al. | |
| 2011/0218192 A1 | 9/2011 | Dillard et al. | |
| 2012/0065195 A1 | 3/2012 | Clark et al. | |
| 2013/0053377 A1 | 2/2013 | Dillard et al. | |
| 2013/0289050 A1 | 10/2013 | Bukhtiyarov et al. | |

FOREIGN PATENT DOCUMENTS

| | | |
|---|---|---|
| JP | 2008-515989 A | 5/2008 |
| WO | 2005058311 A1 | 6/2005 |

(Continued)

OTHER PUBLICATIONS

Gadwood et al., "Synthesis and Biological Activity of Spirocyclic Benzopyran Imidazolone Potassium Channel Openers," J. Med. Chem., 36(10):1480-1487 (1993).
International Search Report for related International Application No. PCT/US2009/004686, Feb. 12, 2010.
International Search Report and Written Opinion for related International Application No. PCT/US2011/025912, Dated: Apr. 1, 2011.
Malamas et al., "Aminoimidazoles as Potent and Selective Human Beta-Secretase (BACE1) Inhibitors," J. Med. Chem., 52:6314-6323 (2009).

(Continued)

*Primary Examiner* — Kahsay Habte
(74) *Attorney, Agent, or Firm* — McCarter & English, LLP; Steven G. Davis; Xin Zhang

(57) ABSTRACT

The present invention relates to compounds represented by Structural Formula (I):

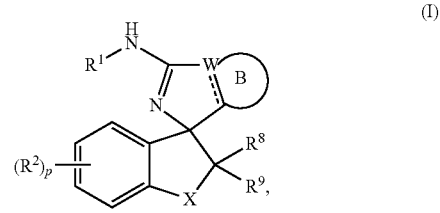

or a pharmaceutically acceptable salt thereof. Definitions for the variables are provided herein.

10 Claims, No Drawings

(56) References Cited

FOREIGN PATENT DOCUMENTS

| | | | |
|---|---|---|---|
| WO | 2006065277 A2 | 6/2006 |
| WO | 2007016012 A2 | 2/2007 |
| WO | 2007038271 A1 | 4/2007 |
| WO | 2007049532 A1 | 5/2007 |
| WO | 2007063114 A2 | 6/2007 |
| WO | 2007076284 A2 | 7/2007 |
| WO | 2007078813 A2 | 7/2007 |
| WO | 2007100536 A1 | 9/2007 |
| WO | 2008010481 A1 | 1/2008 |
| WO | 2008030412 A2 | 3/2008 |
| WO | 2008076043 A1 | 6/2008 |
| WO | 2008076044 A1 | 6/2008 |
| WO | 2008076045 A1 | 6/2008 |
| WO | 2008076046 A1 | 6/2008 |
| WO | 2008103351 A2 | 8/2008 |
| WO | 2008115552 A1 | 9/2008 |
| WO | 2008118379 A2 | 10/2008 |
| WO | 2008133273 A1 | 11/2008 |
| WO | 2008133274 A1 | 11/2008 |
| WO | 2008150217 A1 | 12/2008 |
| WO | 2009134617 A1 | 11/2009 |
| WO | 2010013302 A1 | 2/2010 |
| WO | 2010013794 A1 | 2/2010 |
| WO | 2010021680 A2 | 2/2010 |
| WO | 2010105179 A2 | 9/2010 |
| WO | 2011072064 A1 | 6/2011 |
| WO | 2012087237 A1 | 6/2012 |
| WO | 2013134085 A1 | 9/2013 |

OTHER PUBLICATIONS

Malamas et al., "Design and Synthesis of 5,5'-Disubstituted Aminohydantoins as Potent and Selective Human Beta-Secretase (BACE1) Inhibitors," J. Med. Chem., 53:1146-1158 (2010).

Malamas, "Di-substituted pyridinyl aminohydantoins as potent and highly selective human beta-secretase (BACE1) inhibitors," Bioorganic & Medicinal Chemistry, 18:630-639 (2010).

Nowak et al., "Discovery and initial optimization of 5,5'-disubstituted aminohydantoins as potent beta-secretase (BACE1) inhibitors," Bioorganic & Medicinal Chemistry Letters, 20:632-635 (2010).

Silvestri, "Boom in the Development of Non-Peptidic β-Secretase (BACE1) Inhibitors for the Treatment of Alzheimer's Disease," Medicinal Research Reviews, 29(2):295-338 (2009).

Wang et al., "Application of Fragment-Based NMR Screening, X-ray Crystallography, Structure-Based Design, and Focused Chemical Library Design to Identify Novel μM Leads for the Development of nM BACE-1 (Beta-Site APP Cleaving Enzyme 1) Inhibitors," J. Med. Chem., 53:942-950 (2010).

Written Opinion for related International Application No. PCT/US2009/004686, Feb. 12, 2010.

Written Opinion for related International Application No. PCT/US2010/027173, Sep. 6, 2010.

Zhu et al., "Discovery of Cyclic Acylguanidines as Highly Potent and Selective Beta-Site Amyloid Cleaving Enzyme (BACE) Inhibitors: Part I—Inhibitor Design and Validation," J. Med. Chem., 53:951-965 (2010).

International Search Report for related International Application No. PCT/US2010/027173, Sep. 6, 2010.

INHIBITORS OF BETA-SECRETASE

CROSS-REFERENCED TO RELATED APPLICATION

This application is a divisional of U.S. patent application Ser. No. 13/575,679, filed Nov. 14, 2012, which is a 35 U.S.C. §371 national stage filing of International Application No. PCT/US2011/025912, filed Feb. 23, 2011, which claims the benefit under 35 U.S.C. §119(e) of U.S. Provisional Application No. 61/307,625, filed on Feb. 24, 2010, entitled "Inhibitors of Beta-Secretase". The entire teachings of all of the above applications are incorporated herein by reference.

BACKGROUND OF THE INVENTION

β-Amyloid deposits and neurofibrillary tangles are two major pathologic characterizations associated with Alzheimer's disease (AD). Clinically, AD is characterized by the loss of memory, cognition, reasoning, judgment, and orientation. Also affected, as the disease progresses, are motor, sensory and linguistic abilities until global impairment of multiple cognitive functions occurs. These cognitive losses take place gradually, but typically lead to severe impairment and eventual death in 4-12 years.

β-Amyloid deposits are predominantly an aggregate of Aβ peptide, which in turn is a product of the proteolysis of amyloid precursor protein (APP). More specifically, Aβ peptide results from the cleavage of APP at the C-terminals by one or more γ-secretases, and at the N-terminus by β-secretase enzyme (BACE), also known as aspartyl protease, as part of the β-amyloidogenic pathway.

BACE activity is correlated directly to the generation of Aβ peptide from APP, and studies increasingly indicate that the inhibition of BACE inhibits the production of Aβ peptide.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders.

Recently, Amyloid-β (Aβ) has been reported to be implicated in the development of RGC apotosis in glaucoma, with evidence of caspase-3-mediated abnormal amyloid precursor protein processing, increased expression of Aβ in RGCs in experimental glaucoma and decreased vitreous Aβ levels (consistent with retinal Aβ deposition) in patients with glaucoma.

The present invention provides compounds that are BACE inhibitors and are useful as therapeutic agents in the treatment, prevention and amelioration of a disease or disorder characterized by elevated β-amyloid deposits or β-amyloid levels in a patient.

SUMMARY OF THE INVENTION

One embodiment of the invention is a compound represented by Structural Formula (I):

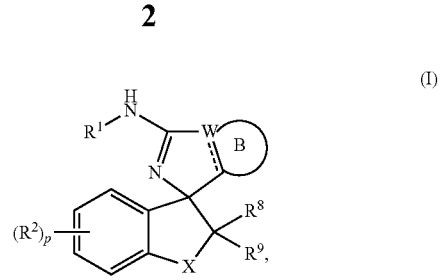

(I)

or a pharmaceutically acceptable salt thereof.

⁓⁓⁓ is a double bond or a single bond.

W is C when ⁓⁓⁓ is a double bond, or W is N or $CR^0$ when ⁓⁓⁓ is a single bond.

Ring B is a 5 or 6 membered carbocycle or a 5 or 6-membered heterocycle containing 1 to 3 heteroatoms independently selected from O, N or S, wherein the heterocycle represented by Ring B is optionally substituted with one or more groups represented by $R^0$, and provided that Ring B contains no adjacent ring oxygen atoms, no adjacent ring sulfur atoms and no ring oxygen atom adjacent to a ring sulfur atom.

X is —O— or —$C(R^3R^4)$—.

Each $R^0$ is independently selected from —H, —CN, —$NO_2$, halogen, —$OR^5$, —$NR^6R^7$, —$S(O)_iR^5$, —$NR^{11}S(O)_2R^5$, —$S(O)_2NR^{12}R^{13}$, —$C(=O)OR^5$, —$OC(=O)R^5$, —$C(=S)OR^5$, —$OC(=S)R^5$, —$C(=O)NR^{12}R^{13}$, —$NR^{11}C(=O)R^5$, —$C(=S)NR^{12}R^{13}$, —$NR^{11}C(=S)R^5$, —$NR^{11}C(=O)OR^5$, —$O(C=O)NR^{12}R^{13}$, —$NR^{11}(C=S)OR^5$, —$O(C=S)NR^{12}R^{13}$, —$NR^{11}(C=O)NR^{12}R^{13}$, —$NR^{11}(C=S)NR^{12}R^{13}$, —$C(=O)R^5$, —$C(=S)R^5$, ($C_1$-$C_6$)alkyl, ($C_3$-$C_4$)cycloalkyl and ($C_3$-$C_4$)cycloalkyl($C_1$-$C_3$)alkyl and wherein each ($C_1$-$C_6$)alkyl and ($C_1$-$C_3$)alkoxy represented by $R^0$ are optionally substituted with 1 to 5 substituents independently selected from the group consisting of halogen, —CN, ($C_1$-$C_6$)alkyl, halo($C_1$-$C_6$)alkyl, ($C_1$-$C_3$)alkoxy($C_1$-$C_6$)alkyl, ($C_1$-$C_3$)alkoxy, and —$NR^6R^7$, or two $R^0$ together with the ring carbon atom to which they are attached form a ($C_3$-$C_6$)cycloalkyl, optionally substituted with halogen, —CN, ($C_1$-$C_6$)alkyl, halo($C_1$-$C_6$)alkyl, ($C_1$-$C_3$)alkoxy($C_1$-$C_6$)alkyl, ($C_1$-$C_3$)alkoxy, and —$NR^6R^7$.

$R^1$ is —H, —OH, —($C_1$-$C_4$)alkoxy, ($C_1$-$C_6$)alkyl, aryl($C_1$-$C_6$)alkyl, or heteroaryl($C_1$-$C_6$)alkyl, wherein each alkyl, aryl and heteroaryl is optionally substituted with 1 to 5 substituents independently selected from halogen, —CN, —OH, ($C_1$-$C_4$)alkyl, halo($C_1$-$C_4$)alkyl, ($C_1$-$C_3$)alkoxy and halo($C_1$-$C_3$)alkoxy.

Each $R^2$ is independently selected from a) —H, halogen, —CN, —$NO_2$, —$OR^5$, —$NR^6R^7$, —$NR^{11}S(O)_2R^5$, —$S(O)_2NR^{12}R^{13}$, —$C(=O)OR^5$, —$OC(=O)R^5$, —$C(=S)OR^5$, —$OC(=S)R^5$, —$C(=O)NR^{12}R^{13}$, —$NR^{11}C(=O)R^5$, —$C(=S)NR^{12}R^{13}$, —$NR^{11}C(=S)R^5$, —$NR^{11}C(=O)OR^5$, —$O(C=O)NR^{12}R^{13}$, —$NR^{11}(C=S)OR^5$, —$O(C=S)NR^{12}R^{13}$, —$NR^{11}(C=O)NR^{12}R^{13}$, —$NR^{11}(C=S)NR^{12}R^{13}$, —$C(=O)R^5$, —$C(=S)R^5$; and b) ($C_1$-$C_6$)alkyl, ($C_2$-$C_6$)alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkynyl, ($C_4$-$C_8$)cycloalkenyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkynyl, aryl, aryl($C_1$-$C_6$)alkyl, aryl($C_2$-$C_6$)alkynyl, heteroaryl, heteroaryl($C_1$-$C_6$)alkyl, and heteroaryl($C_2$-$C_6$)alkynyl, wherein each ($C_1$-$C_6$)alkyl, ($C_2$-$C_6$)alkenyl, ($C_2$-$C_6$)alkynyl, ($C_3$-$C_8$)cycloalkyl, ($C_3$-$C_8$)cycloalkyl($C_1$-$C_6$)alkyl, ($C_3$-$C_8$)cycloalkyl($C_2$-$C_6$)alkynyl, ($C_4$-$C_8$)cycloalkenyl, ($C_3$-$C_9$)heterocycloalkyl, ($C_3$-$C_9$)heterocycloalkyl($C_1$-$C_6$)alkyl, ($C_3$-$C_9$)heterocycloalkyl($C_2$-$C_6$)alkynyl, aryl, aryl($C_1$-

$C_6$)alkyl, aryl($C_2$-$C_6$)alkynyl, heteroaryl, heteroaryl($C_1$-$C_6$) alkyl, and heteroaryl($C_2$-$C_6$)alkynyl is optionally substituted with 1 to 5 substituents independently selected from the group consisting of halogen, —CN, —NO$_2$, —OR$^5$, —NR$^6$R$^7$, —S(O)$_i$R$^5$, —NR$^{11}$S(O)$_2$R$^5$, —S(O)$_2$NR$^{12}$R$^{13}$, —C(=O)OR$^5$, —OC(=O)R$^5$, —C(=S)OR$^5$, —OC(=S) R$^5$, —C(=O)NR$^{12}$R$^{13}$, —NR$^{11}$C(=O)R$^5$, —C(=S) NR$^{12}$R$^{13}$, —NR$^{11}$C(=S)R$^5$, —NR$^{11}$(C=O)OR$^5$, —O(C=O)NR$^{12}$R$^{13}$, —NR$^{11}$(C=S)OR$^5$, —O(C=S) NR$^{12}$R$^{13}$, —NR$^{11}$(C=O)NR$^{12}$R$^{13}$, —NR$^{11}$(C=S) NR$^{12}$R$^{13}$, —C(=O)R$^5$, —C(=S)R$^5$, ($C_1$-$C_6$)alkyl, ($C_2$-$C_6$) alkynyl, ($C_3$-$C_8$)cycloalkyl, ($C_4$-$C_8$)cycloalkenyl, ($C_3$-$C_9$) heterocycloalkyl, ($C_2$-$C_6$)alkenyl, halo($C_1$-$C_6$)alkyl, —($C_1$-$C_6$)alkylene-NR$^{11}$—SO$_2$—($C_1$-$C_3$)alkyl, hydroxy($C_1$-$C_6$) alkyl, cyano($C_1$-$C_6$)alkyl, —($C_1$-$C_6$)alkylene-NR$^{11}$—C (=O)—($C_1$-$C_3$)alkyl, ($C_1$-$C_3$)alkoxy, halo($C_1$-$C_3$)alkoxy, ($C_1$-$C_6$)alkoxy($C_1$-$C_3$)alkyl, aryl, and heteroaryl, wherein the cycloalkyl, heterocycloalkyl, aryl and heteroaryl groups in the substituents on the groups represented by R$_2$ are each optionally substituted with 1 to 3 substituents independently selected from halogen, —CN, ($C_1$-$C_6$)alkyl, halo($C_1$-$C_6$) alkyl, ($C_1$-$C_3$)alkoxy, halo($C_1$-$C_3$)alkoxy and ($C_1$-$C_3$)alkoxy ($C_1$-$C_6$)alkyl.

R$^3$ and R$^4$ are each independently —H, halogen, ($C_1$-$C_4$) alkyl, halo($C_1$-$C_4$)alkyl, ($C_1$-$C_3$)alkoxy, halo($C_1$-$C_3$)alkoxy or ($C_1$-$C_3$)alkoxy($C_1$-$C_4$)alkyl.

R$^5$ is selected from the group consisting of —H, ($C_1$-$C_3$) alkyl, halo($C_1$-$C_4$)alkyl, ($C_1$-$C_3$)alkoxy($C_1$-$C_3$)alkyl, ($C_3$-$C_6$)cycloalkyl, ($C_3$-$C_6$)cycloalkyl($C_1$-$C_3$)alkyl and phenyl optionally substituted with halogen, —CN, —NO$_2$, ($C_1$-$C_3$) alkyl, halo($C_1$-$C_3$)alkyl or ($C_1$-$C_3$)alkoxy($C_1$-$C_3$)alkyl.

R$^6$ is —H or ($C_1$-$C_3$)alkyl.

R$^7$ is —H, ($C_1$-$C_3$)alkyl, halo($C_1$-$C_3$)alkyl, ($C_3$-$C_6$)cycloalkyl, ($C_3$-$C_6$)cycloalkyl($C_1$-$C_3$)alkyl or ($C_1$-$C_3$)alkoxy ($C_1$-$C_3$)alkyl.

R$^8$ and R$^9$, together with the carbon to which they are attached, form ring A, which is a 3-9 membered cycloalkyl optionally substituted with 1 to 4 substituents independently selected from the group consisting of halogen, —CN, —OR$^5$, —NR$^6$R$^7$, —S(O)$_i$R$^5$, —NR$^{11}$S(=O)$_2$R$^5$, —C(=O)OR$^5$, —C(=O)NR$^{12}$R$^{13}$, —NR$^{11}$C(=O)R$^5$, —C(=S)NR$^{12}$R$^{13}$, —C(=O)R$^5$, ($C_1$-$C_6$)alkyl, ($C_2$-$C_6$)alkenyl, aryl, aryl($C_1$-$C_6$)alkyl, heteroaryl and heteroaryl($C_1$-$C_6$)alkyl, wherein each of the ($C_1$-$C_6$)alkyl, ($C_2$-$C_6$)alkenyl, aryl, aryl($C_1$-$C_6$) alkyl, heteroaryl and heteroaryl($C_1$-$C_6$)alkyl substituents on Ring A is optionally substituted with 1 to 5 substituents independently selected from the group consisting of ($C_1$-$C_6$)alkyl, halogen, —CN, —OH, —NR$^{11}$SO$_2$($C_1$-$C_3$)alkyl, —NR$^{11}$C (=O)—($C_1$-$C_3$)alkyl, ($C_1$-$C_6$)alkyl, halo($C_1$-$C_6$)alkyl, ($C_1$-$C_3$)alkoxy and ($C_1$-$C_3$)alkoxy($C_1$-$C_6$)alkyl, and wherein Ring A is optionally fused to phenyl group optionally substituted with 1 to 5 substituents independently selected from the group consisting of ($C_1$-$C_6$)alkyl, halogen, —CN, —OH, —NR$^{11}$SO$_2$($C_1$-$C_3$)alkyl, —NR$^{11}$C(=O)—($C_1$-$C_3$)alkyl, ($C_1$-$C_6$)alkyl, halo($C_1$-$C_6$)alkyl, ($C_1$-$C_3$)alkoxy and ($C_1$-$C_3$) alkoxy($C_1$-$C_6$)alkyl.

R$^{11}$ is —H or ($C_1$-$C_3$)alkyl.

R$^{12}$ is —H or ($C_1$-$C_3$)alkyl.

R$^{13}$ is —H, ($C_1$-$C_3$)alkyl, halo($C_1$-$C_3$)alkyl, ($C_3$-$C_6$)cycloalkyl($C_1$-$C_3$)alkyl or ($C_1$-$C_3$)alkoxy($C_1$-$C_3$)alkyl.

i is 0, 1 or 2.

p is 1, 2, 3 or 4.

Another embodiment of the invention is a pharmaceutical composition comprising a pharmaceutically acceptable carrier or diluent and a compound represented by Structural Formula (I) or a pharmaceutically acceptable salt thereof.

Another embodiment of the invention is a method of inhibiting BACE activity in a subject in need of such treatment. The method comprises administering to the subject an effective amount of a compound represented by Structural Formula (I) or a pharmaceutically acceptable salt thereof.

Another embodiment of the invention is a method of treating a BACE mediated disorder in a subject. The method comprises administering to the subject an effective amount of a compound represented by Structural Formula (I) or a pharmaceutically acceptable salt thereof.

Another embodiment of the invention is the use of a compound represented by Structural Formula (I) or a pharmaceutically acceptable salt thereof for the manufacture of a medicament for inhibiting BACE activity in a subject.

Another embodiment of the invention is the use of a compound represented by Structural Formula (I) or a pharmaceutically acceptable salt thereof for the manufacture of a medicament for treating a BACE mediated disorder in a subject.

Another embodiment of the invention is the use of a compound represented by Structural Formula (I) or a pharmaceutically acceptable salt thereof for inhibiting BACE activity in a subject.

Another embodiment of the invention is the use of a compound represented by Structural Formula (I) or a pharmaceutically acceptable salt thereof for treating a BACE mediated disorder in a subject.

DETAILED DESCRIPTION OF THE INVENTION

The present invention is directed to compounds represented by the Structural Formula (I), or a pharmaceutically acceptable salt thereof. Values and alternative values for the variables in Structural Formula (I) and the other structural formulas described herein are provided in the following paragraphs.

R$^0$ is as described above for Structural Formula (I). Alternatively, R$^0$ is —H, ($C_1$-$C_6$)alkyl, ($C_1$-$C_3$)alkoxy, —CN, —NR$^6$R$^7$, wherein each ($C_1$-$C_6$)alkyl and ($C_1$-$C_3$)alkoxy are optionally substituted with 1 to 5 substituents independently selected from the group consisting of halogen, —CN, ($C_1$-$C_6$)alkyl, halo($C_1$-$C_6$)alkyl, ($C_1$-$C_3$)alkoxy($C_1$-$C_6$)alkyl, ($C_1$-$C_3$)alkoxy, and —NR$^6$R$^7$, or two R$^0$ together with the ring carbon atom to which they are attached form a ($C_3$-$C_6$) cycloalkyl, optionally substituted with halogen, —CN, ($C_1$-$C_6$)alkyl, halo($C_1$-$C_3$)alkyl, ($C_1$-$C_3$)alkoxy($C_1$-$C_6$)alkyl, ($C_1$-$C_3$)alkoxy, and —NR$^6$R$^7$. In another alternative, each R$^0$, when present, is independently selected from the group consisting of —H, —F, —CN, -Me, -Et, —OMe, —CF$_3$ and —NH$_2$, or two R$^0$ together with the carbon atom to which they are attached form a cyclopropyl ring.

R$^1$ is as described above for Structural Formula (I). Alternatively, R$^1$ is a —H or a ($C_1$-$C_3$)alkyl. In another alternative, R$^1$ is —H.

R$^2$ is as described above for Structural Formula (I). In one alternative, each R$^2$ is independently selected from the group consisting of —H, halogen, —CN, —NO$_2$, —OR$^5$, —C(=O)NR$^{12}$R$^{13}$, ($C_1$-$C_6$)alkyl, ($C_2$-$C_6$)alkenyl, ($C_2$-$C_6$) alkynyl, phenyl($C_2$-$C_6$)alkynyl, ($C_3$-$C_8$)cycloalkyl, ($C_4$-$C_8$) cyclohexenyl, phenyl, pyridyl, thiazolyl, pyridazinyl, pyridazinone, pyridinone, thiophenyl, pyrrolyl, pyrimidinyl, pyrazinyl, indolyl, pyrrolidinyl, piperazinyl and morpholinyl, each of the ($C_1$-$C_6$)alkyl, ($C_2$-$C_6$)alkenyl, ($C_2$-$C_6$)alkynyl, phenyl($C_2$-$C_6$)alkynyl, ($C_3$-$C_8$)cycloalkyl, ($C_4$-$C_8$)cyclohexenyl, phenyl, pyridinyl, thiazolyl, pyridazinyl, pyridazinone, pyridinone, thiophenyl, pyrrolyl, pyrimidinyl, pyrazinyl, indolyl, pyrrolidinyl, piperazinyl and morpholinyl is optionally substituted with 1 to 3 substituents independently selected from the group consisting of halogen, —OH, —CN, —NO$_2$, (C$_1$-C$_6$)alkyl, (C$_2$-C$_6$)alkynyl, halo(C$_1$-C$_6$)alkyl, (C$_3$-C$_8$)cycloalkyl, (C$_1$-C$_3$)alkoxy, halo(C$_1$-C$_3$)alkoxy, (C$_1$-C$_3$)alkoxy(C$_1$-C$_6$)alkyl, —NR$^6$R$^7$ and —SO$_2$R$^c$.

Alternatively, R$^2$ is —Br, —Cl, —CN, —OR$^5$, (C$_1$-C$_6$) alkyl, (C$_2$-C$_6$)alkynyl, phenyl or pyridinyl, wherein each of the (C$_1$-C$_6$)alkyl, (C$_2$-C$_6$)alkynyl, phenyl and pyridinyl is optionally substituted with 1 to 3 substituents independently selected from —F, —Cl, —Br, —CN, (C$_3$-C$_6$)cycloalkyl, (C$_1$-C$_3$)alkyl, halo(C$_1$-C$_3$)alkyl, (C$_1$-C$_3$)alkoxy and halo(C$_1$-C$_3$)alkoxy.

In another alternative embodiment, each R$^2$ is independently selected from the group consisting of —Br, —Cl, —CN, cyclopropylethyl, cyclopropylethynyl, cyclopropylmethoxy, 5-trifluoromethyl-2-pyridyl, 2-pyridyl, 3-chloro-5-fluorophenyl, 3-cyanophenyl, 3-trifluoromethoxyphenyl and methoxy.

R$^3$ and R$^4$ are as described above for Structural Formula (I). Alternatively, R$^3$ and R$^4$ are —H.

R$^5$ is as described above for Structural Formula (I). In another embodiment, R$^5$ is selected from the group consisting of —H, (C$_1$-C$_3$)alkyl, halo(C$_1$-C$_3$)alkyl, (C$_1$-C$_3$)alkoxy(C$_1$-C$_3$)alkyl, (C$_3$-C$_6$)cycloalkyl, (C$_3$-C$_6$)cycloalkyl(C$_1$-C$_3$)alkyl and phenyl optionally substituted with halogen, —CN, —NO$_2$, (C$_1$-C$_3$)alkyl, halo(C$_1$-C$_3$)alkyl or (C$_1$-C$_3$)alkoxy (C$_1$-C$_3$)alkyl. Alternatively, R$^5$ is selected from the group consisting of —H, -Me, —CF$_3$ and cyclopropylmethyl.

R$^6$ and R$^7$ are as described above for Structural Formula (I). Alternatively, R$^6$ and R$^7$ are both —H.

R$^8$ and R$^9$ and Ring A are as described above for Structural Formula (I).

Alternatively, ring A is represented by the following structural formula:

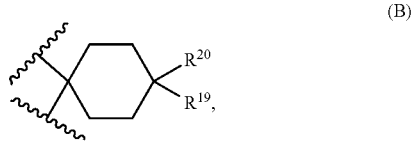

(B)

wherein R$^{19}$ and R$^{20}$ are each independently selected from —H, halogen, —CN, —OR$^5$, —NR$^6$R$^7$, —S(O)$_i$R$^5$, —NR$^{11}$S(=O)$_2$R$^5$, —C(=O)OR$^5$, —C(=O)NR$^{12}$R$^{13}$, —NR$^{11}$C(=O)R$^5$, —C(=S)NR$^{12}$R$^{13}$, —C(=O)R$^5$, (C$_1$-C$_6$)alkyl, (C$_2$-C$_6$)alkenyl, aryl, aryl(C$_1$-C$_6$)alkyl, heteroaryl and heteroaryl(C$_1$-C$_6$)alkyl, wherein each of the (C$_1$-C$_6$) alkyl, (C$_2$-C$_6$)alkenyl, aryl, aryl(C$_1$-C$_6$)alkyl, heteroaryl and heteroaryl(C$_1$-C$_6$)alkyl groups represented by R$_{19}$ and R$_{20}$ is optionally substituted with 1 to 5 substituents independently selected from the group consisting of halogen, —CN, —OH, —NR$^{11}$SO$_2$(C$_1$-C$_3$)alkyl, —NR$^{11}$C(=O)—(C$_1$-C$_3$)alkyl, (C$_1$-C$_6$)alkyl, halo(C$_1$-C$_6$)alkyl, (C$_1$-C$_3$)alkoxy and (C$_1$-C$_3$) alkoxy(C$_1$-C$_6$)alkyl. In another alternative, R$^{19}$ and R$^{20}$ are each independently selected from —H, halogen, —CN, —OR$^5$, —NR$^6$R$^7$, —S(O)$_i$R$^5$, —NR$^{11}$S(=O)$_2$R$^5$, —C(=O)OR$^5$, —C(=O)NR$^{12}$R$^{13}$, —NR$^{11}$C(=O)R$^5$, —C(=S)NR$^{12}$R$^{13}$, —C(=O)R$^5$ and (C$_1$-C$_6$)alkyl, wherein the (C$_1$-C$_6$)alkyl group represented by R$_{19}$ and R$_{20}$ is optionally substituted with 1 to 5 substituents independently selected from the group consisting of halogen, —CN, —OH, —NR$^{11}$SO$_2$(C$_1$-C$_3$)alkyl, —NR$^{11}$C(=O)—(C$_1$-C$_3$)alkyl, (C$_1$-C$_6$)alkyl, halo(C$_1$-C$_6$)alkyl, (C$_1$-C$_3$)alkoxy and (C$_1$-C$_3$) alkoxy(C$_1$-C$_6$)alkyl. Alternatively, R$^{20}$ is —H and R$^{19}$ is —OH, (C$_1$-C$_3$)alkoxy, halo(C$_1$-C$_3$)alkoxy or (C$_1$-C$_3$)alkoxy (C$_1$-C$_3$)alkoxy.

In another alternative, Ring A is represented by:

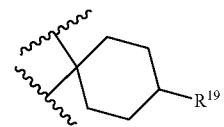

and R$^{19}$ is —H, —OH, (C$_1$-C$_3$)alkoxy, halo(C$_1$-C$_3$)alkoxy or (C$_1$-C$_3$)alkoxy(C$_1$-C$_3$)alkoxy.

R$^{11}$ is as described above for Structural Formula (I). Alternatively, R$^{11}$ is —H or (C$_1$-C$_3$)alkyl. In another alternative, R$^{11}$ is —H.

R$^{12}$ and R$^{13}$ are as described above for Structural Formula (I). Alternatively, R$^{12}$ and R$^{13}$ are both —H.

R$^{15}$ is as described above for Structural Formula (I). Alternatively, R$^{15}$ is —H or (C$_1$-C$_6$)alkyl. In another alternative, R$_{15}$ is —H.

In one embodiment, X is as described above for Structural Formula (I). Alternatively, X is —O— or —CH$_2$—. In another alternative, X is —O—. In yet another alternative embodiment, X is —CH$_2$—.

In one embodiment, i is as described above for Structural Formula (I). Alternatively, i is 0. In another alternative embodiment, i is 2.

In one embodiment, p is as described above for Structural Formula (I). In another embodiment, p is 2. Alternatively, p is 1.

Ring B is a monocyclic carbocycle or a monocyclic heterocycle, wherein the carbocycle or the heterocycle is optionally substituted with one or more R$^0$ provided that Ring B contains no adjacent ring oxygen atoms, no adjacent ring sulfur atoms and no ring oxygen atom adjacent to a ring sulfur atom. In another embodiment, ring B is a 5 or 6-membered heterocycle containing 1 to 3 heteroatoms independently selected from the group consisting of N, O and S, wherein the heterocycle is optionally substituted with one or more R$^0$, provided that Ring B contains no adjacent ring oxygen atoms, no adjacent ring sulfur atoms and no ring oxygen atom adjacent to a ring sulfur atom. Alternatively, ring B is a phenyl ring optionally substituted with one or more R$^0$.

W is C when ----- is a double bond, or W is N or CR$^0$ when ----- is a single bond.

In a 1$^{st}$ embodiment, the compound of the present invention is represented by s structural formula selected from:

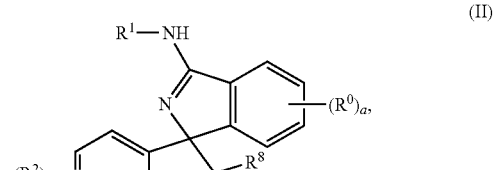

(II)

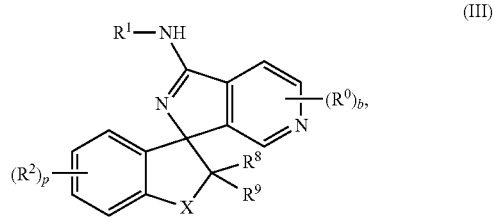

(III)

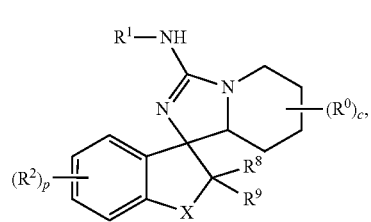
(IV)

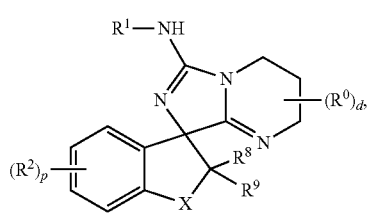
(V)

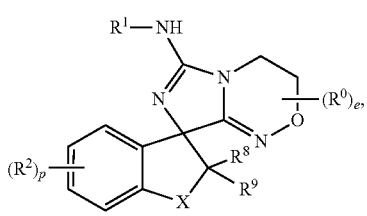
(VI)

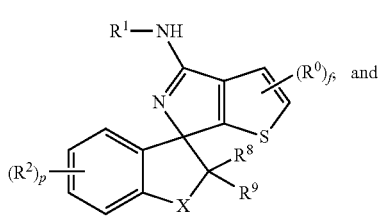
(VII)

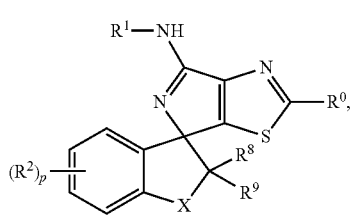
(VIII)

or a pharmaceutically acceptable salt thereof, wherein:
a is 1, 2, 3 or 4;
b is 1, 2 or 3;
c is an integer from 1 to 8;
d is an integer from 1 to 6;
e is 1, 2, 3 or 4; and
f is 1 or 2.

The remainder of the variables are as described above for Structural Formula (I). Alternatively for Structural Formulas (II)-(VIII), X is —CH$_2$—. In another alternative for Structural Formulas (II)-(VIII), X is —O—.

In a 2$^{nd}$ embodiment, the compound of the present invention is represented by a structural formula selected from:

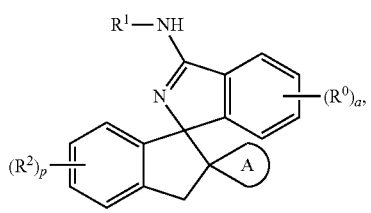
(IIa)

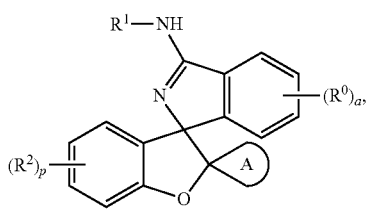
(IIb)

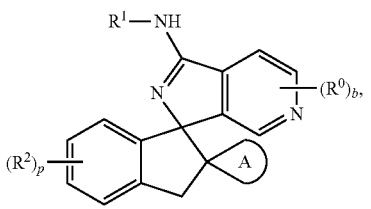
(IIIa)

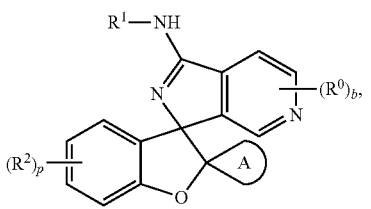
(IIIb)

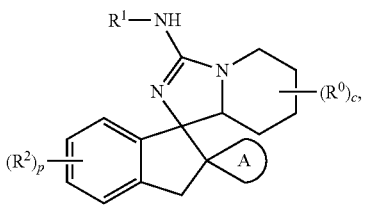
(IVa)

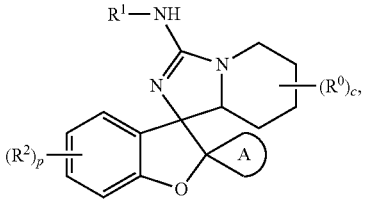
(IVb)

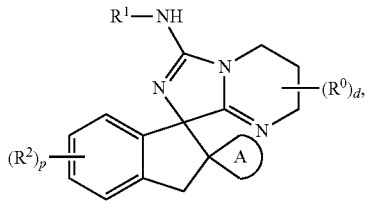
(Va)

-continued

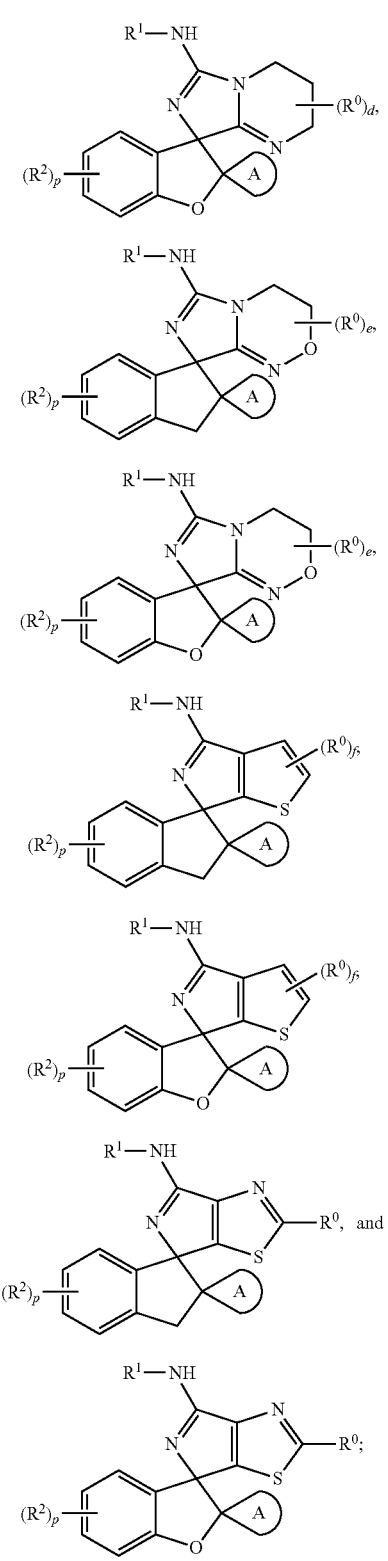

(Vb)

(VIa)

(VIb)

(VIIa)

(VIIb)

(VIIIa)

(VIIIb)

or a pharmaceutically acceptable salt thereof, wherein the variables are as described above for Structural Formulas (II)-(VIII) in the 1st embodiment.

In a 3rd embodiment, the compound of the invention is represented by a structural formula selected from Structural Formulas (I), (II)-(VIII), (IIa)-(VIIIa) and (IIb)-(VIIIb), wherein: ring A (or $R^8$ and $R^9$ taken together with the carbon atom to which they are bonded) is represented by Structural Formula (B):

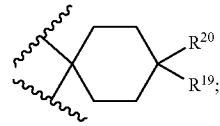

wherein $R^{19}$ and $R^{20}$ are each independently selected from —H, halogen, —CN, —$OR^5$, —$NR^6R^7$, —$S(O)_rR^5$, —$NR^{11}S(=O)_2R^5$, —C(=O)$OR^5$, —C(=O)$NR^{12}R^{13}$, —$NR^{11}C(=O)R^5$, —C(=S)$NR^{12}R^{13}$, —C(=O)$R^5$, ($C_1$-$C_6$)alkyl, ($C_2$-$C_6$)alkenyl, aryl, aryl($C_1$-$C_6$)alkyl, heteroaryl and heteroaryl($C_1$-$C_6$)alkyl, wherein each of the ($C_1$-$C_6$) alkyl, ($C_2$-$C_6$)alkenyl, aryl, aryl($C_1$-$C_6$)alkyl, heteroaryl and heteroaryl($C_1$-$C_6$)alkyl groups represented by $R_{19}$ and $R_{20}$ is optionally substituted with 1 to 5 substituents independently selected from the group consisting of halogen, —CN, —OH, —$NR^{11}SO_2$($C_1$-$C_3$)alkyl, —$NR^{11}C(=O)$—($C_1$-$C_3$)alkyl, ($C_1$-$C_6$)alkyl, halo($C_1$-$C_6$)alkyl, ($C_1$-$C_3$)alkoxy and ($C_1$-$C_3$) alkoxy($C_1$-$C_6$)alkyl. The remainder of the variables are as described above in the $1^{st}$ or $2^{nd}$ embodiment. Alternatively, $R^{20}$ is —H and $R^{19}$ is —OH, ($C_1$-$C_3$)alkoxy, halo($C_1$-$C_3$) alkoxy or ($C_1$-$C_3$)alkoxy($C_1$-$C_3$)alkoxy; and the remainder of the variables are as described above in the $1^{st}$ or $2^{nd}$ embodiment.

In a 4th embodiment, the compound of the present invention is represented by a structural formula selected from:

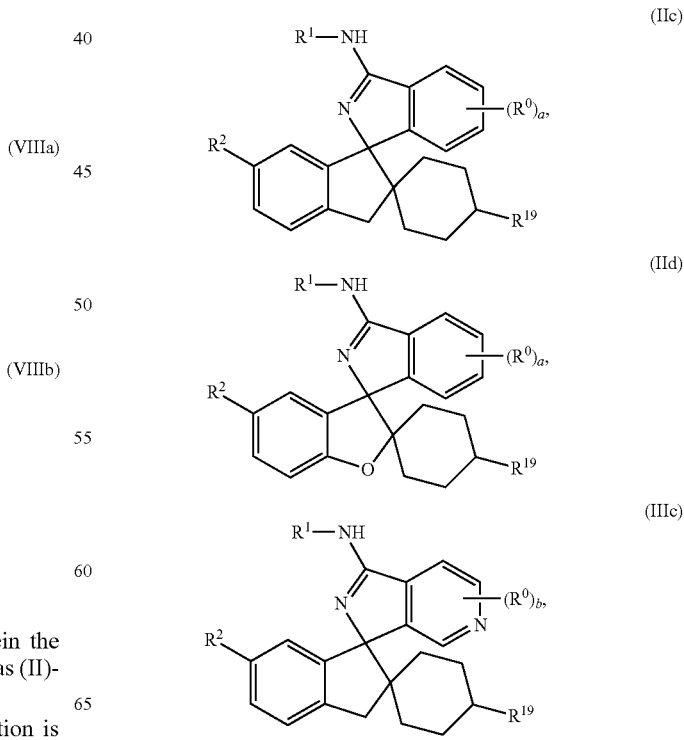

(IIc)

(IId)

(IIIc)

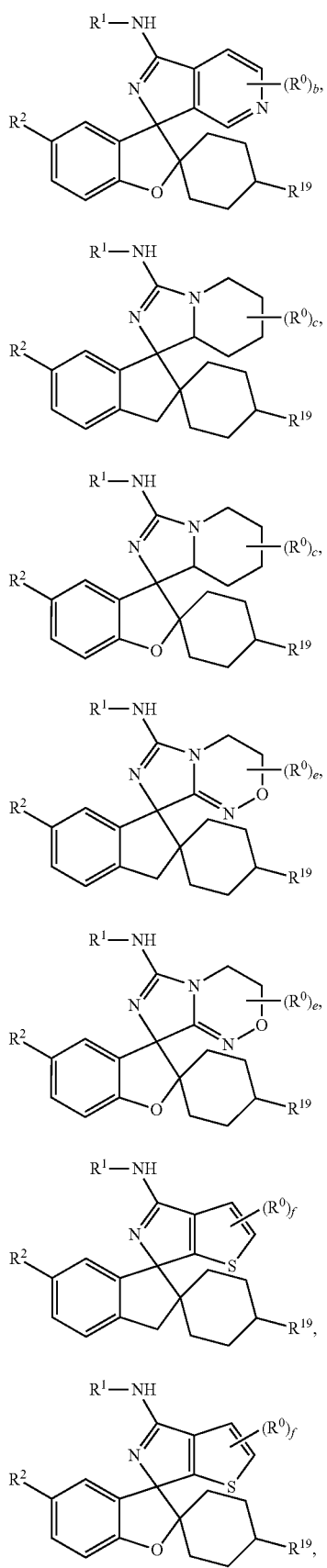
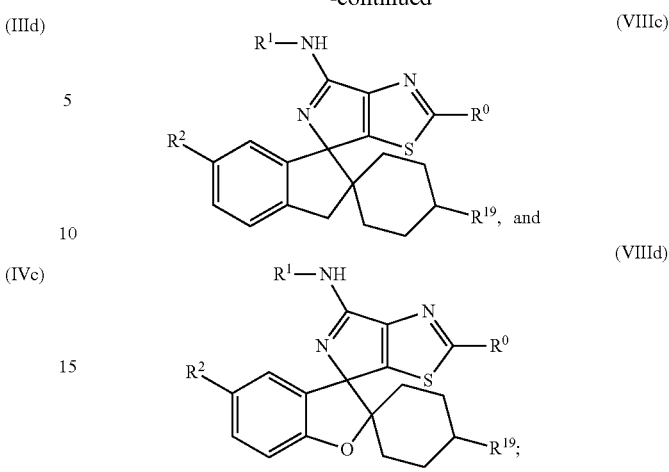

or a pharmaceutically acceptable salt thereof, wherein:

$R^0$ is —H, $(C_1-C_6)$alkyl, $(C_1-C_3)$alkoxy, —CN, —NR$^6$R$^7$, wherein each $(C_1-C_6)$alkyl and $(C_1-C_3)$alkoxy are optionally substituted with 1 to 5 substituents independently selected from the group consisting of halogen, —CN, $(C_1-C_6)$alkyl, halo$(C_1-C_6)$alkyl, $(C_1-C_3)$alkoxy$(C_1-C_6)$alkyl, $(C_1-C_3)$alkoxy, and —NR$^6$R$^7$, or two R$^0$ together with the ring carbon atom to which they are attached form a $(C_3-C_6)$cycloalkyl, optionally substituted with halogen, —CN, $(C_1-C_6)$alkyl, halo$(C_1-C_6)$alkyl, $(C_1-C_3)$alkoxy$(C_1-C_6)$alkyl, $(C_1-C_3)$alkoxy, and —NR$^6$R$^7$;

$R^{19}$ is —OH, $(C_1-C_3)$alkoxy, halo$(C_1-C_3)$alkoxy or $(C_1-C_3)$alkoxy$(C_1-C_3)$alkoxy;

a is 1;
b is 1;
c is 1;
d is 1 or 2;
e is 1; and
f is 1; and the remainder of the variables are as described above for Structural Formulas (II)-(VIII) in the 1$^{st}$ embodiment.

In a 5$^{th}$ embodiment, the compound of the invention is represented by a structural formula selected from Structural Formulas (I), (II)-(VIII), (IIa)-(VIIIa), (IIb)-(VIIIb), (IIc)-(VIIIc) and (IId)-(VIIId):

$R^1$ is a —H or a $(C_1-C_3)$alkyl;

each $R^2$ is independently selected from the group consisting of —H, halogen, —CN, —NO$_2$, —OR$^5$, —C(=O)NR$^{12}$R$^{13}$, $(C_1-C_6)$alkyl, $(C_2-C_6)$alkenyl, $(C_2-C_6)$alkynyl, phenyl$(C_2-C_6)$alkynyl, $(C_3-C_8)$cycloalkyl, $(C_4-C_8)$cycloalkenyl, phenyl, pyridyl, thiazolyl, pyridazinyl, pyridazinone, pyridinone, thiophenyl, pyrrolyl, pyrimidinyl, pyrazinyl, indolyl, pyrrolidinyl, piperazinyl and morpholinyl, each of the $(C_1-C_6)$alkyl, $(C_2-C_6)$alkenyl, $(C_2-C_6)$alkynyl, phenyl $(C_2-C_6)$alkynyl, $(C_3-C_8)$cycloalkyl, $(C_4-C_8)$cyclohexenyl, phenyl, pyridinyl, thiazolyl, pyridazinyl, pyridazinone, pyridinone, thiophenyl, pyrrolyl, pyrimidinyl, pyrazinyl, indolyl, pyrrolidinyl, piperazinyl and morpholinyl is optionally substituted with 1 to 3 substituents independently selected from the group consisting of halogen, —OH, —CN, —NO$_2$, $(C_1-C_6)$alkyl, $(C_2-C_6)$alkynyl, halo$(C_1-C_6)$alkyl, $(C_3-C_8)$cycloalkyl, $(C_1-C_3)$alkoxy, halo$(C_1-C_3)$alkoxy, $(C_1-C_3)$alkoxy$(C_1-C_6)$alkyl, —NR$^6$R$^7$ and —SO$_2$R$^c$. Each R$^2$ is independently selected from —Br, —Cl, —CN, —OR$^5$, $(C_1-C_6)$alkyl, $(C_2-C_6)$alkynyl, phenyl and pyridinyl, wherein each of the $(C_1-C_6)$alkyl, $(C_2-C_6)$alkynyl, phenyl and pyridinyl is optionally substituted with 1 to 3 substituents independently selected from —F, —Cl, —Br, —CN, $(C_3-C_6)$cycloalkyl, $(C_1-C_3)$alkyl, halo$(C_1-C_3)$alkyl, $(C_1-C_3)$alkoxy and halo$(C_1-C_3)$alkoxy;

each $R^0$, when present, is independently selected from the group consisting of —H, halogen, —CN, $(C_1-C_6)$alkyl, halo$(C_1-C_6)$alkyl, $(C_1-C_3)$alkoxy and —$NR^6R^7$, or two $R^0$ together with the carbon atom to which they are attached form a $(C_3-C_6)$cycloalkyl optionally substituted with 1 to 3 substituents independently selected from halogen, —CN, $(C_1-C_6)$alkyl, halo$(C_1-C_6)$alkyl, $(C_1-C_3)$alkoxy, halo$(C_1-C_3)$alkoxy and $(C_1-C_3)$alkoxy$(C_1-C_6)$alkyl; and the remainder of the variables are as described above in the $1^{st}$, $2^{nd}$, $3^{rd}$ or $4^{th}$ embodiment.

In a $6^{th}$ embodiment, the compound of the invention is represented by a structural formula selected from Structural Formulas (I), (II)-(VIII), (IIa)-(VIIIa), (IIb)-(VIIIb), (IIc)-(VIIIc) and (IId)-(VIIId):

$R^5$ is selected from the group consisting of —H, $(C_1-C_3)$alkyl, halo$(C_1-C_3)$alkyl, $(C_1-C_3)$alkoxy$(C_1-C_3)$alkyl, $(C_3-C_6)$cycloalkyl, $(C_3-C_6)$cycloalkyl$(C_1-C_3)$alkyl and phenyl optionally substituted with halogen, —CN, —$NO_2$, $(C_1-C_3)$alkyl, halo$(C_1-C_3)$alkyl or $(C_1-C_3)$alkoxy$(C_1-C_3)$alkyl;

$R^6$ is —H or $(C_1-C_3)$alkyl;

$R^7$ is —H, $(C_1-C_3)$alkyl, halo$(C_1-C_3)$alkyl, $(C_3-C_6)$cycloalkyl, $(C_3-C_6)$cycloalkyl$(C_1-C_3)$alkyl or $(C_1-C_3)$alkoxy$(C_1-C_3)$alkyl;

$R^{11}$ is —H or $(C_1-C_3)$alkyl;

$R^{12}$ is —H or $(C_1-C_3)$alkyl; and $R^{13}$ is $(C_1-C_3)$alkyl, halo$(C_1-C_3)$alkyl, $(C_3-C_6)$cycloalkyl$(C_1-C_3)$alkyl or $(C_1-C_3)$alkoxy$(C_1-C_3)$alkyl; and the remainder of the variables are as described above in the $1^{st}$, $2^{nd}$, $3^{rd}$, $4^{th}$ or $5^{th}$ embodiment.

In a $7^{th}$ embodiment, the compound of the invention is represented by a structural formula selected from Structural Formulas (I), (II)-(VIII), (IIa)-(VIIIa), (IIb)-(VIIIb), (IIc)-(VIIIc) and (IId)-(VIIId):

$R^1$ is —H;

each $R^2$ is independently selected from the group consisting of —Br, —Cl, —CN, cyclopropylethyl, cyclopropylethynyl, cyclopropylmethoxy, 5-trifluoromethyl-2-pyridyl, 2-pyridyl, 3-chloro-5-fluorophenyl, 3-cyanophenyl, 3-trifluoromethoxyphenyl and methoxy; and each $R^0$, when present, is independently selected from the group consisting of —F, —CN, -Me, -Et, —OMe, —$CF_3$ and —$NH_2$, or two $R^0$ together with the carbon atom to which they are attached form a cyclopropyl ring; and the remainder of the variables are as described above in the in the $1^{st}$, $2^{nd}$, $3^{th}$, $4^{th}$, $5^{th}$ or $6^{th}$ embodiment.

In an $8^{th}$ embodiment, the compound of the invention is represented by a structural formulas selected from Structural Formulas (I), (II)-(VIII), (IIa)-(VIIIa), (IIb)-(VIIIb), (IIc)-(VIIIc) and (IId)-(VIIId):

$R^5$ is selected from the group consisting of -Me, —$CF_3$ and cyclopropylmethyl; and $R^6$, $R^7$, $R^{11}$, $R^{12}$ and $R^{13}$ are all —H; and the remainder of the variables are as described above in the $1^{st}$, $2^{nd}$, $3^{th}$, $4^{th}$, $5^{th}$ $6^{th}$ or $7^{th}$ embodiment.

Another embodiment of the present invention is directed to the compounds described in Examples 1-37, an enatiomer, a diastereomer, a tautomer or a pharmaceutically acceptable salt thereof.

GENERAL DEFINITIONS

Terms not specifically defined herein should be understood to have the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $(C_1-C_6)$alkyl means an alkyl group or radical having 1 to 6 carbon atoms. In general, for groups comprising two or more subgroups, the last named subgroup is the radical attachment point, for example, the substituent "aryl$(C_1-C_3)$ alkyl" means an aryl group which is bound to a $(C_1-C_3)$alkyl group, the latter of which is bound to the core or to the group to which the substituent is attached.

In case a compound of the present invention is depicted in form of a chemical name and as a formula, the formula shall prevail in case of any discrepancy.

When any variable (e.g. aryl, heterocyclyl, $R^1$, $R^2$ etc.) occurs more than once in a compound, its definition on each occurrence is independent of any other occurrence.

"Alkyl" means a saturated aliphatic branched or straight-chain monovalent hydrocarbon radical having the specified number of carbon atoms. For example, "$(C_1-C_6)$alkyl" means a radical having from 1-6 carbon atoms in a linear or branched arrangement. "$(C_1-C_6)$alkyl" includes methyl (—$CH_3$), ethyl (—$CH_2CH_3$), propyl (—$CH_2CH_2CH_3$ and —$CH(CH_3)CH_3$), butyl (—$CH_2CH_2CH_2CH_3$, —$CH(CH_3)CH_2CH_3$, $CH_2CH(CH_3)CH_3$ and —$C(CH_3)_2CH_3$,), pentyl (—$CH_2CH_2CH_2CH_2CH_3$, —$CH(CH_3)CH_2CH_2CH_3$, —$CH_2CH(CH_3)CH_2CH_3$, —$CH_2CH_2CH(CH_3)CH_3$, —$C(CH_3)_2CH_2CH_3$, —$CH_2C(CH_3)_2CH_3$, —$CH(CH_3)CH(CH_3)CH_3$ and —$CH(CH_2CH_3)CH_2CH_3$), and hexyl (—$CH_2(CH_2)_4CH_3$, —$CH(CH_3)CH_2CH_2CH_2CH_3$, —$CH_2CH(CH_3)CH_2CH_2CH_3$, —$CH_2CH_2CH(CH_3)CH_2CH_3$, —$CH_2CH_2CH_2CH(CH_3)CH_3$, —$C(CH_3)_2CH_2CH_2CH_3$, —$CH_2C(CH_3)_2CH_2CH_3$, —$CH_2CH_2C(CH_3)_2CH_3$, —$CH(CH_3)CH(CH_3)CH_2CH_3$, —$CH_2CH(CH_3)CH(CH_3)CH_3$, —$CH(CH_3)CH_2CH(CH_3)CH_3$, —$CH_2CH(CH_2CH_3)CH_2CH_3$, and —$CH_2CH(CH(CH_3)_2)CH_3$).

"Alkenyl" means branched or straight-chain monovalent hydrocarbon radical containing at least one double bond and having specified number of carbon atoms. Alkenyl may be mono or polyunsaturated, and may exist in the E or Z configuration. For example, "$(C_2-C_6)$alkenyl" means a radical having from 2-6 carbon atoms in a linear or branched arrangement.

"Alkynyl" means branched or straight-chain monovalent hydrocarbon radical containing at least one triple bond and having specified number of carbon atoms. For example, "$(C_2-C_6)$alkynyl" means a radical having from 2-6 carbon atoms in a linear or branched arrangement.

"Alkoxy" means an alkyl radical attached through an oxygen linking atom. "$(C_1-C_4)$-alkoxy" includes methoxy, ethoxy, propoxy, and butoxy.

"Aryl", "aryl group", "aryl ring", "aromatic", "aromatic group" and "aromatic ring" are used interchangeably and mean an aromatic monocyclic, or polycyclic hydrocarbon ring system. "Aryl" includes, but is not limited to, phenyl, naphthalenyl, fluorenyl, indenyl, azulenyl, and anthracenyl.

The term "carbocyclyl" as used either alone or in combination with another radical, means a monocyclic or polycyclic ring structure consisting only of carbon containing between one and four rings. The term "carbocycle" refers to fully saturated and aromatic ring systems and partially saturated ring systems and encompasses fused, spiro systems, and bridged systems.

"Cycloalkene" is an unsaturated and non-aromatic aliphatic cyclic hydrocarbon radical having the specified number of carbon atoms. It can be monocyclic, bicyclic, tricyclic, fused, bridged, or spiro. Thus, monocyclic ($C_3$-$C_8$)cycloalkene means a radical having from 3-8 carbon atoms arranged in a ring. A ($C_3$-$C_8$)cycloalkene includes cyclobutene, cyclopentene, cyclohexene, cycloheptene and cyclooctene.

"Cycloalkyl" means a saturated aliphatic cyclic hydrocarbon radical having the specified number of carbon atoms. It can be monocyclic, bicyclic, polycyclic (e.g., tricyclic), fused, bridged, or spiro. For example, monocyclic ($C_3$-$C_8$) cycloalkyl means a radical having from 3-8 carbon atoms arranged in a monocyclic ring. A ($C_3$-$C_8$)cycloalkyl includes, but is not limited to, cyclopropyl, cyclobutyl, cyclopentyl, cyclohexyl, cycloheptyl and cyclooctane.

Monocyclic ring systems have a single ring. They include saturated, partially saturated or unsaturated carbocyclic rings or heterocycles having the specified number of ring atoms.

Bicyclic ring systems have two rings that have at least one ring atom in common. Bicyclic ring systems include fused, bridged and spiro ring systems. The two rings can both be aliphatic (e.g., cycloalkyl or cycloheteroalkyl), both be aromatic (e.g., aryl or heteroaryl), or a combination thereof. The bicyclic ring systems can optionally contain 1 to 3 heteroatoms in the ring structure and each heteroatom is independently selected from the group consisting O, N and S.

A fused bicyclic ring system has two rings which have two adjacent ring atoms in common. The two rings can both be aliphatic (e.g., cycloalkyl or cycloheteroalkyl), both be aromatic (e.g., aryl or heteroaryl), or a combination thereof. For example, the first ring can be monocyclic cycloalkyl or monocyclic cycloheteroalkyl, and the second ring can a cycloalkyl, partially unsaturated carbocycle, aryl, heteroaryl or a monocyclic cycloheteroalkyl. For example, the second ring can be a ($C_3$-$C_6$)cycloalkyl, such as cyclopropyl, cyclobutyl, cyclopentyl and cyclohexyl. Alternatively, the second ring can be an aryl ring, e.g., phenyl.

A spiro bicyclic ring system has two rings which have only one ring atom in common. The rings are cycloalkyl, cycloheteroalkyl or partially saturated counterparts thereof. Examples of spiral bicyclic ring system include, but are not limited to, spiro[2.2]pentane, spiro[2.3]hexane, spiro[13.3]heptane, spiro[2.4]heptane, spiro[13.4]octane, spiro[12.5]octane, azaspiro[4.4]nonane, 7-azaspiro[4.4]nonane, azasprio[4.5]decane, 8-azaspiro[4.5]decane, azaspiro[5.5]undecane, 3-azaspiro[5.5]undecane and 3,9-diazaspiro[5.5]undecane.

A bridged ring system has two rings which have three or more adjacent ring atoms in common. The two rings are cycloalkyl, cycloheteroalkyl or partially saturated counterparts thereof.

Polycyclic ring systems have more than two rings (e.g., three rings resulting in a tricyclic ring system) and adjacent rings have at least one ring atom in common. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Heterocycle" means a saturated, unsaturated, or aromatic mono- or polycyclic-ring system containing one or more heteroatoms independently selected from N, O or S. A heterocycle can be heteroaryl ring or heterocycloalkyl.

"Heterocycloalkyl" means a saturated 4-12 membered ring radical having specified number of carbon atoms in the ring. The heterocycloalkyl contains 1 to 4 heteroatoms, which may be the same or different, selected from N, O or S. The heterocycloalkyl ring optionally contains one or more double bonds and is optionally fused to one or more aromatic rings or heteroaromatic rings. It can be monocyclic, bicyclic, tricyclic, fused, bridged, or spiro. For example, ($C_3$-$C_9$)heterocycloalkyl mean a saturated ring radical containing 3-9 ring atoms.

Exemplary "heterocycloalkyl" includes, but is not limited to, the following exemplary structures which are not depicted as radicals as each form may be attached through a covalent bond to any atom so long as appropriate valences are maintained:

Monocyclic

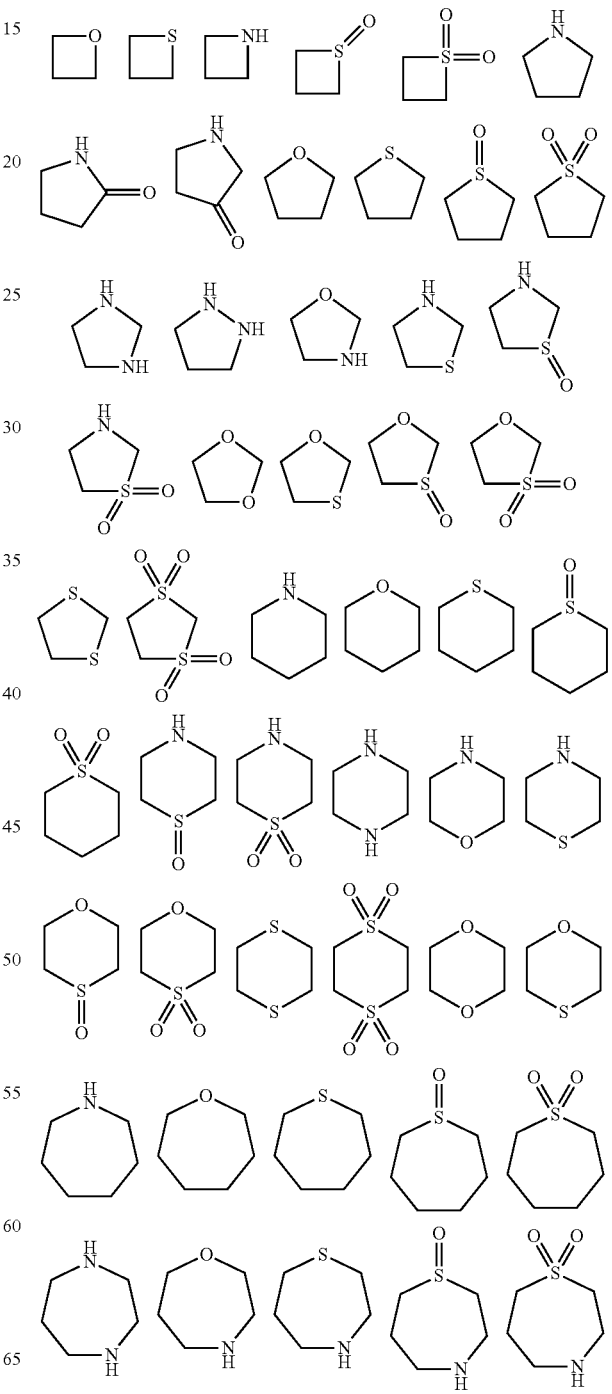

-continued
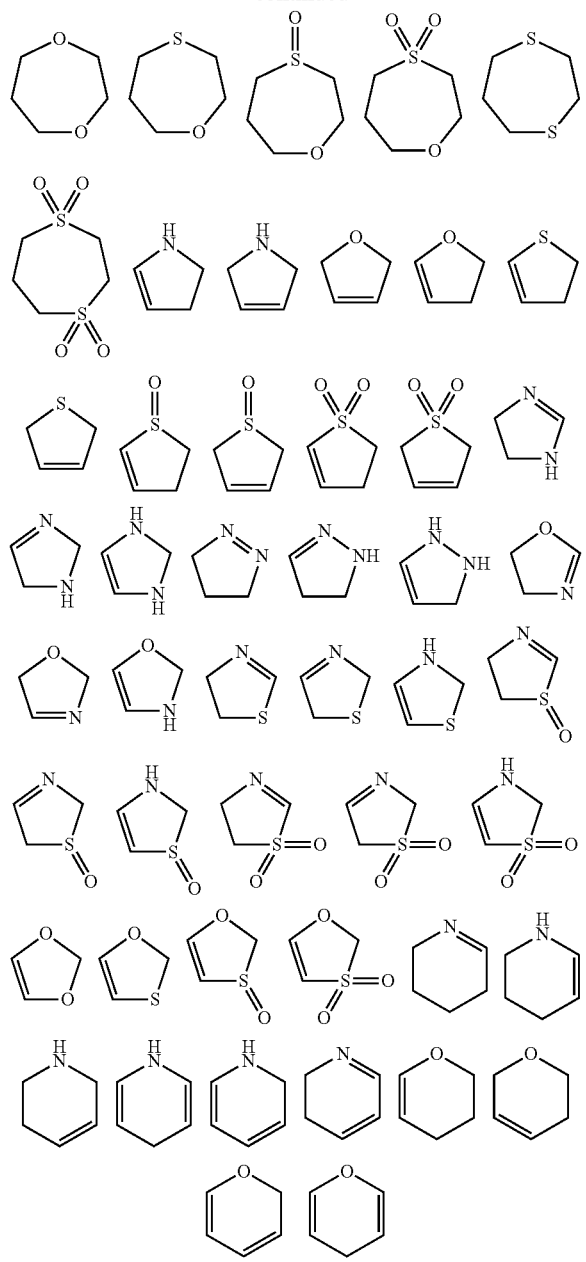
Bridged Bicyclic
-continued
Fused Bicyclic
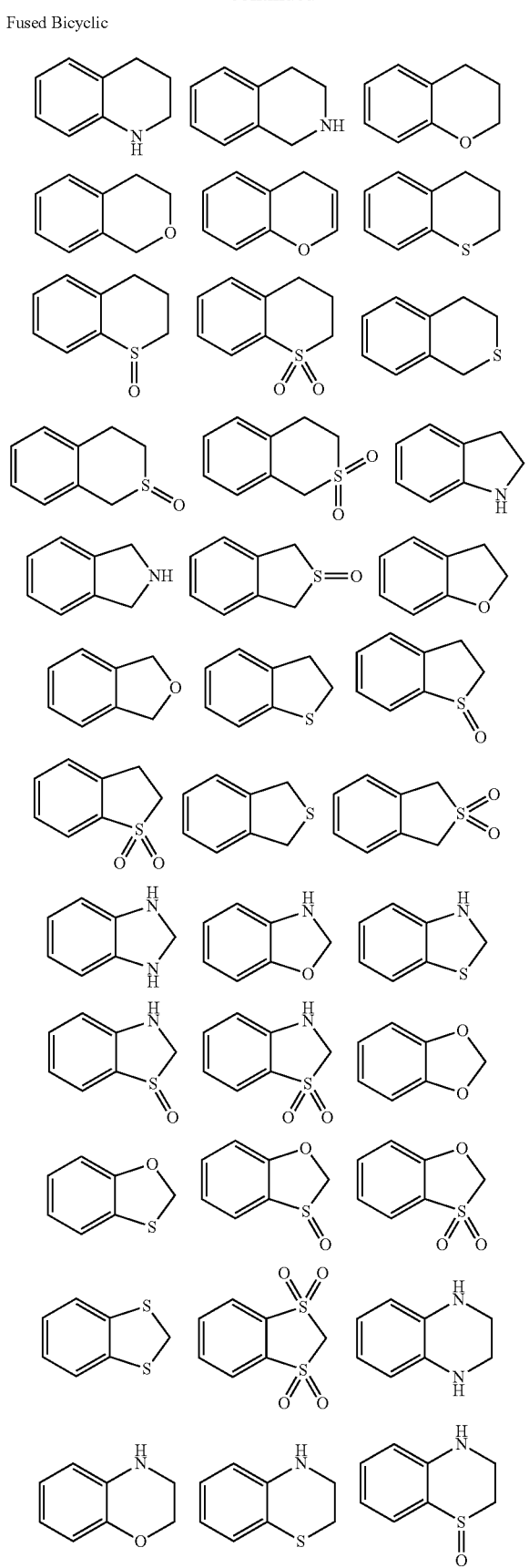

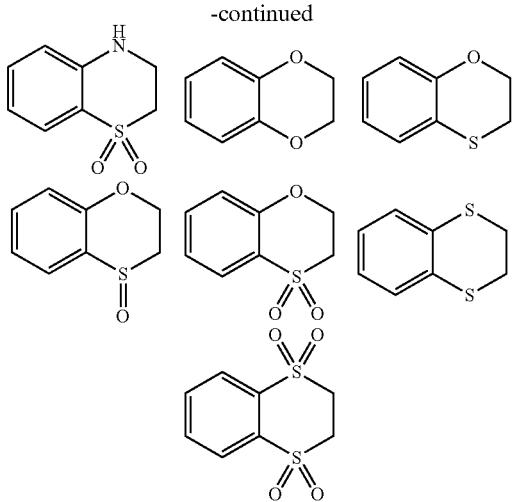

A ring nitrogen atom in a heterocycloalkyl can be substituted, provided that it is bonded to each of its adjacent ring atoms with a single bond. Unless otherwise indicated, exemplary substituents include alkyl, cycloalkyl, aryl, arylalkyl, heteraryl, heteroarylalkyl, $(C_1-C_6)$alkyl, halo$(C_1-C_6)$alkyl or $(C_1-C_3)$alkylcarbonyl, each of which is optionally substituted with halogen, hydroxy, alkoxy, haloalkyl or alkyl (preferably $(C_1-C_6)$alkyl, halo$(C_1-C_6)$alkyl or $(C_1-C_3)$alkylcarbonyl, each of which is optionally substituted with halogen, hydroxy, alkoxy, haloalkyl or alkyl). Ring sulfur atoms can optionally be mono or di-oxygenated (i.e., —S(O) or —S(O)$_2$).

Haloalkyl and halocycloalkyl include mono, poly, and perhaloalkyl groups where the halogens are independently selected from fluorine, chlorine, and bromine. For example, a halo$(C_1-C_3)$alkyl includes, but is not limited to, —CF$_3$, —CH$_2$CH$_2$F, —CH$_2$CHF$_2$, —CH$_2$CF$_3$ and —CH$_2$CF$_2$CHF$_2$.

"Heteroaryl" is used interchangeably with "heteroaryl group", "heteroaryl ring", "heteroaromatic", "heteroaromatic group" and "heteroaromatic ring". "Heteroaryl" means a monovalent heteroaromatic monocyclic or polycylic ring radical. Monocyclic heteroaryl rings are 5- and 6-membered aromatic heterocyclic rings containing 1 to 4 heteroatoms independently selected from N, O, and S. Bicyclic heteroaryl rings include bicyclo[4.4.0] and bicyclo[4.3.0] fused ring systems containing 1 to 4 heteroatoms independently selected from N, O, and S.

For example, "heteroaryl" includes, but is not limited to, the following exemplary structures which are not depicted as radicals as each from may be attached through a covalent bond to any atom so long as appropriate valences are maintained:

Monocyclic

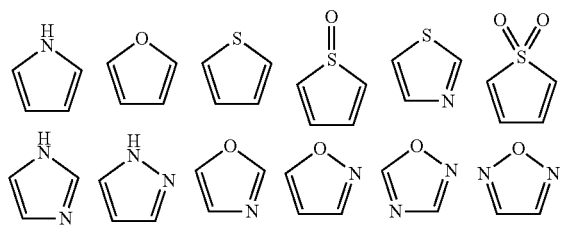

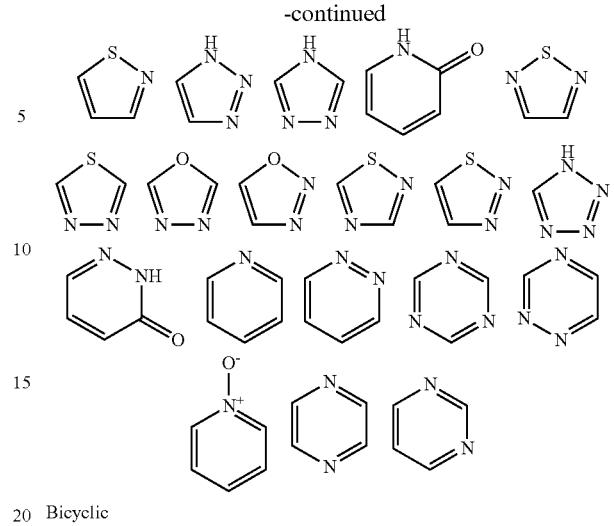

Bicyclic

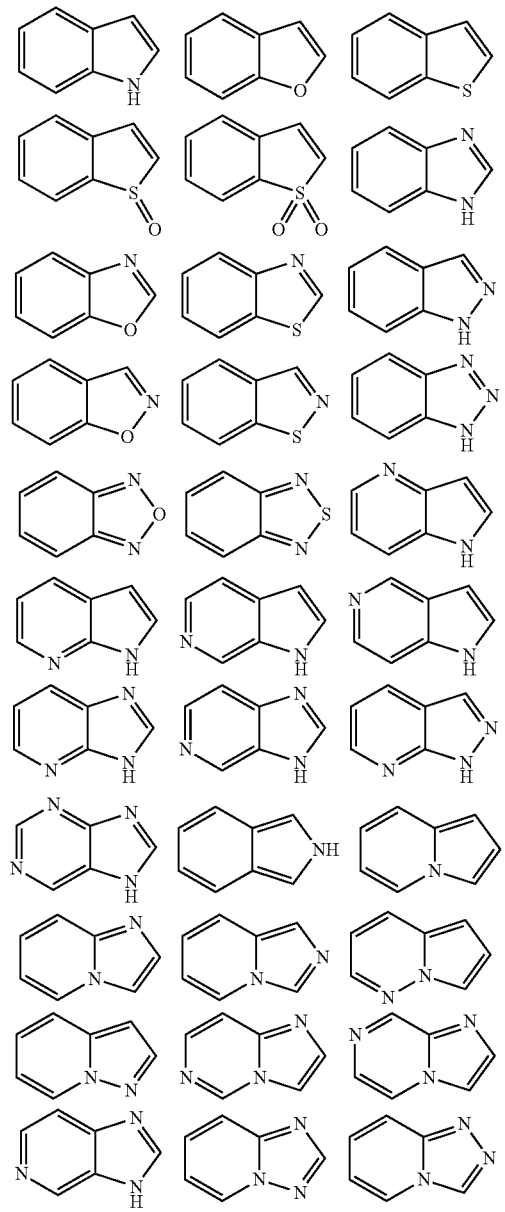

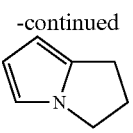

"Halo($C_1$-$C_n$)alkoxy" means a ($C_1$-$C_n$)alkyl radical attached through an oxygen linking atom, wherein the ($C_1$-$C_n$)alkyl is substituted with one or more halogens independently selected from fluorine, chlorine, bromine and iodine. For example, a halo($C_1$-$C_3$)alkoxy includes, but is not limited to, —$OCF_3$, —$OCH_2CF_3$, —$OCHFCHF_2$ and —$OCH_2CF_2CHF_2$.

"Hetero" refers to the replacement of at least one carbon atom member in a ring system with at least one heteroatom selected from N, S, and O. A hetero ring may have 1, 2, 3, or 4 carbon atom members replaced by a heteroatom.

"Halogen" used herein refers to fluorine, chlorine, bromine, or iodine.

When substituted, unless otherwise indicated, suitable substituents for alkyl, alkenyl, alkkynyl, cycloalkyl, cycloalkenyl, carbocycle, heterocycle, heterocycloalkyl, aryl and heteroaryl, include halogen, ($C_1$-$C_4$)alkyl, halo($C_1$-$C_4$)alkyl, ($C_1$-$C_3$)alkoxy, halo($C_1$-$C_3$)alkoxy or ($C_1$-$C_3$)alkoxy($C_1$-$C_4$) alkyl, cyano, nitro, ($C_1$-$C_3$)alkylcarbonyl, ($C_1$-$C_3$)alkoxycarbonyl, phenyl, thienyl, furanyl and pyridyl. The phenyl, thienyl, furanyl and pryidyl are optionally further substituted with halogen, ($C_1$-$C_4$)alkyl, halo($C_1$-$C_4$)alkyl, ($C_1$-$C_3$) alkoxy, halo($C_1$-$C_3$)alkoxy or ($C_1$-$C_3$)alkoxy($C_1$-$C_4$)alkyl, cyano, nitro, ($C_1$-$C_3$)alkylcarbonyl and ($C_1$-$C_3$)alkoxycarbonyl.

The compounds of the invention may be present in the form of pharmaceutically acceptable salts. For use in medicines, the salts of the compounds of the invention refer to non-toxic "pharmaceutically acceptable salts." The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Pharmaceutically acceptable salt forms include pharmaceutically acceptable acidic/anionic or basic/cationic salts. Examples of pharmaceutically acceptable salts include, but are not limited to, mineral or organic acid salts of basic residues such as amines; alkali or organic salts of acidic residues such as carboxylic acids; and the like.

For example, such salts include, the acetate, ascorbate, benzenesulfonate, benzoate, bezylate, bicarbonate, bitartrate, bromide, calcium edetate, camsylate, carbonate, chloride, citrate, dihydrochloride, edetate, edisylate, ethane disulfonate, estolate, esylate, fumarate, glyceptate, gluconate, glutamate, glycolate, glycollylarsanilate, hexylresorcinate, hydrabamine, hydrobromide, hydrochloride, hydroxymaleate, hydroxynaphthoate, iodide, isethionate, lactate, lactobionate, malate, maleate, mandelate, methanesulfonate, mesylate, methylbromide, methylnitrate, methylsulfate, mucate, napsylate, nitrate, oxalate, pamoate, pantothenate, phenylacetate, phosphate/diphospate, polygalacturonate, propionate, salicylate, stearate, subacetate, succinate, sulfamide, sulfate, tannate, tartrate, teoclate, tosylate, triethiodide, ammonium, benzathine, chloroprocaine, colline, diethanolamine, ethylenediamine, meglumine and procaine salts. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

The disclosed compounds of the invention are BACE inhibitors for treating, preventing or ameliorating disorders or diseases characterized by elevated β-amyloid deposits or β-amyloid levels in a subject. The present invention also provides a method for the treatment of a disorder related to or associated with excessive BACE activity in a patient in need thereof which comprises administering to said patient an effective amount of a disclosed compound or a pharmaceutically acceptable salt thereof. The present invention also provides methods for inhibiting the activity of BACE in a subject in need thereof, comprising administering to a subject and/or contacting a receptor thereof with an effective amount of at least one disclosed compound or a pharmaceutically acceptable salt thereof. The present invention also provides methods of ameliorating β-amyloid deposits in a subject in need thereof, comprising administering to said subject an effective amount of at least one disclosed compound or a pharmaceutically acceptable salt thereof.

As such, the disclosed BACE inhibitors can be used to treat neurodegenerative disorders, disorders characterized by cognitive decline, cognitive impairment, dementia and diseases characterized by production of β-amyloid deposits or neurofibrillary tangles.

Exemplary diseases or disorders that can be treated by the disclosed BACE inhibitors include Alzheimer's disease, Trisomy 21 (Down's Syndrome), Hereditary Cerebral Hemorrhage with Amyloidosis of the Dutch-typle (HCHWA-D), senile dementia, cerebral amyloid angiopathy, degenerative dementia, dementias of mixed vascular and degenerative origin, dementia associated with Parkinson's disease, dementia associated with progressive supranuclear palsy and dementia associated with cortical basal degeneration, diffuse Lewy body type of Alzheimer's disease and glaucoma.

Accordingly, the present invention relates to a disclosed compound or a pharmaceutically acceptable salt thereof as a medicament.

In a further embodiment, the present invention relates to methods for the treatment or prevention of above-mentioned diseases and conditions, which method comprises the administration of an effective amount of a disclosed compound or a pharmaceutically acceptable salt thereof.

The invention includes a therapeutic method for treating or ameliorating an BACE mediated disorder in a subject in need thereof comprising administering to a subject in need thereof an effective amount of a disclosed compound or a pharmaceutically acceptable salt thereof or composition thereof.

Administration methods include administering an effective amount (i.e., an effective amount) of a compound or composition of the invention at different times during the course of therapy or concurrently in a combination form. The methods of the invention include all known therapeutic treatment regimens.

As used herein, the term "subject" and "patient" may be used interchangeably, and means a human in need of treatment.

As used herein, the term "treating" or "treatment" refers to obtaining desired pharmacological and/or physiological effect. The effect can be prophylactic or therapeutic, which includes achieving, partially or substantially, one or more of the following results: partially or totally reducing the extent of the disease, disorder or syndrome; ameliorating or improving a clinical symptom or indicator associated with the disorder; delaying, inhibiting or decreasing the likelihood of the progression of the disease, disorder or syndrome; or partially or totally delaying, inhibiting or reducing the likelihood of the onset or development of disease, disorder or syndrome.

"Effective amount" means that amount of active compound agent that elicits the desired biological response in a subject. Such response includes alleviation of the symptoms of the disease or disorder being treated. The effective amount of a compound of the invention in such a therapeutic method is from about 0.01 mg/kg/day to about 1000 mg/kg/day or from about 0.1 mg/kg/day to about 100 mg/kg/day.

"Pharmaceutically acceptable carrier" means compounds and compositions that are of sufficient purity and quality for use in the formulation of a composition of the invention and that, when appropriately administered to an animal or human, do not produce an adverse reaction.

In one embodiment, the present invention includes combination therapy for treating or ameliorating a disease or a disorder described herein. The combination therapy comprises administering a combination of at least one compound represented by structural formula (A), (I) or (I') with another compound selected from the group of, for example, gamma-secretase inhibitors; amyloid aggregation inhibitors (e.g. ELND-005); directly or indirectly acting neuroprotective and/or disease-modifying substances; anti-oxidants (e.g. vitamin E or ginkolide); anti-inflammatory substances (e.g. Cox inhibitors, NSAIDs additionally or exclusively having Abeta lowering properties); HMG-CoA reductase inhibitors (statins); acetylcholinesterase inhibitors (e.g., donepezil, rivastigmine, tacrine, galantamine, memantine; tacrine); NMDA receptor antagonists (e.g. memantine); AMPA receptor agonists; AMPA receptor positive modulators, AMPkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunisation with Abeta or parts thereof or passive immunisation with humanised anti-Abeta antibodies or nanobodies) for the treatment of the above-mentioned diseases and conditions.

Combination therapy includes co-administration of the compound of the invention and said other agent, sequential administration of the compound and the other agent, administration of a composition containing the compound and the other agent, or simultaneous administration of separate compositions containing of the compound and the other agent.

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 0.005 to 10% wt.-% of the composition as a whole.

The dosage form containing the composition of the invention contains an effective amount of the active ingredient necessary to provide a therapeutic effect. The composition may contain from about 5,000 mg to about 0.5 mg (preferably, from about 1,000 mg to about 0.5 mg) of a compound of the invention or salt form thereof and may be constituted into any form suitable for the selected mode of administration.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

Methods of Preparation

In cases where the synthetic intermediates and final products of Formula I described below contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not usually described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

| Abbreviation | Meaning |
|---|---|
| AcCl | acetyl chloride |
| AlCl$_3$ | aluminum chloride |
| Ar | argon |
| B$_2$H$_6$ | diborane |
| Boc | tert-butoxy carbonyl or t-butoxy carbonyl |
| Borax | sodium borate |
| brine | saturated aqueous NaCl |
| CH$_2$N$_2$ | carbodiimide |
| CH$_3$CN | acetonitrile |
| Cs$_2$CO$_3$ | cesium carbonate |
| CuBr-SMe$_2$ | cuprous bromide methylsulfide complex |
| CuI | cuprous iodide |
| DCM or CH$_2$Cl$_2$ | methylene chloride |
| DEA | diethylamine |
| DIBAL-H | diisobutylaluminum hydride |
| DMAP | 4-(dimethylamino)pyridine |
| EtI | ethyl iodide |
| Et | ethyl |
| Et$_2$O | ethyl ether |
| EtOAc, EA | ethyl acetate |
| EtOH | ethanol |
| Et$_3$O$^+$BF$_4^-$ | triethyloxonium tetrafluoroborate |
| h, hr | hour |
| HCl | hydrochloric acid |
| H$_2$O | water |
| H$_2$O$_2$ | hydrogen peroxide |
| HCONH$_2$ | formamide |
| HMPA | hexamethylphosphoric triamide |
| HMPT | hexamethylphosphorous triamide |
| HOAc or AcOH | acetic acid |
| HPLC | high performance liquid chromatography |
| K$_2$CO$_3$ | potassium carbonate |
| KCN | potassium cyanide |
| LAH | LiAlH$_4$ |
| Lawesson's reagent | 2,4-bis(4-methoxyphenyl)-1,3,2,4-dithiadiphosphetane 2,4-disulfide |
| LDA | lithium diisopropylamide |
| Min | minute |
| MeOH | methanol |
| MeI | methyl iodide |
| Me | methyl |
| MeNHOH | methylhydroxylamine |
| MTBA | 4-(methylthio)benzoic acid |
| Me$_2$S | methyl sulfide |
| NaOH | sodium hydroxid |
| NaOMe | sodium methoxide |
| Na$_2$S$_2$O$_3$ | sodium thiosulfate |
| Na$_2$SO$_4$ | sodium sulfate |
| NHMDS | Sodium bis(trimethylsilyl)amide |
| NH$_4$OH | ammonium hydroxide |
| (NH$_4$)$_2$CO$_3$ | ammonium carbonate |
| NH$_4$I | ammonium iodide |
| Na$_2$CO$_3$ | sodium carbonate |
| NaHCO$_3$ | sodium bicarbonate |
| NaH | sodium hydride |
| PdCl$_2$dppf | [1,1-bis(diphenylphosphino)ferrocene]dichloropalladium(II) |
| Pd(OH)$_2$ | palladium hydroxide |
| Pd(PPh$_3$)$_2$Cl$_2$ | bis(triphenylphosphine)palladium (II) dichloride |
| Pd(PPh$_3$)$_4$ | tetrakis(triphenylphosphine)palladium(0) |
| PrBr | propyl bromide |
| PBr$_3$ | phosphorous tribromide |
| PCC | pyridinium chlorochromate |
| PE | petroleum ether |
| PPA | polyphosphoric acid |
| PPh$_3$ | triphenyl phosphine |
| Selectfluor™ | 1-chloromethyl-4-fluoro-1,4-diazoniabicyclo[2.2.2]octane bis(tetrafluoroborate) |
| SOCl$_2$ | thionyl chloride |
| TEA | triethylamine |
| TFA | trifluoroacetic acid |
| THF | tetrahydrofuran |
| TLC | thin layer chromatography |
| TiCl$_4$ | titanium chloride |
| TMSCl | trimethylsilyl chloride |

Compounds of the invention can be prepared employing conventional methods that utilize readily available reagents and starting materials. The reagents used in the preparation of the compounds of this invention can be either commercially obtained or can be prepared by standard procedures described in the literature. Representative compounds of the present invention can be prepared using the following synthetic schemes.

EXEMPLIFICATION

Example I-1

Synthesis of Intermediate A—Method 1

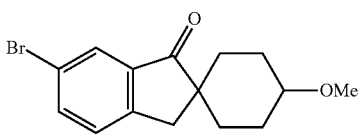

Step 1. synthesis of 1,5-dibromo-3-methoxypentane

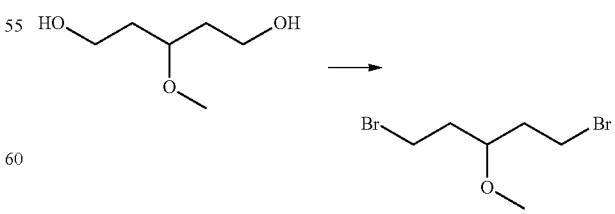

To a solution of 3-methoxypentane-1,5-diol (1 g, 7.46 mmol) in DCM (10 mL) was added PPh$_3$ (5.77 g, 22.05 mmol) and CBr$_4$ (4.87 g, 14.7 mmol) at 0° C. The mixture was stirred at 0° C. for 2 h. The mixture was filtrated and the filtrate was concentrated to give the residue, which was purified by column chromatography to give 1,5-dibromo-3-methoxypentane (1.2 g, 62%). $^1$H-NMR (CDCl$_3$): 2.0 (m, 4H), 3.3 (m, 3H), 3.37 (m, 4H), 3.5 (m, 1H), 3.7 (m, 4H).

Step 2. Synthesis of 6'-bromo-4-methoxyspiro[cyclohexane-1,2'-inden]-1'(3'H)-one

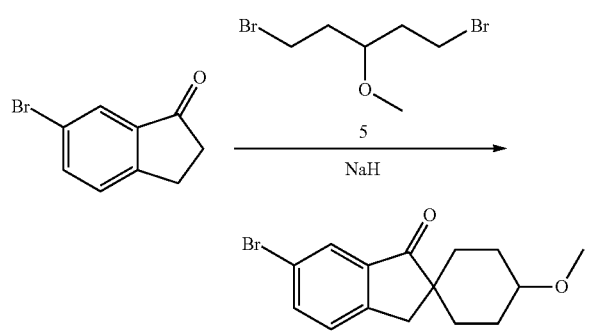

A mixture of 6-bromo-2,3-dihydro-1H-inden-1-one (1.037 g, 4.94 mmol) and 1,5-dibromo-3-methoxypentane (1.2 g, 4.94 mmol) in THF (16 mL) was added NaH (237.12 mg, 60%, 9.88 mmol) at room temperature. The mixture was refluxes for 3 h. The mixture was quenched with water and extracted with EtOAc. The organic layer was dried and concentrated to give the residue, which was purified by column chromatography to give 6'-bromo-4-methoxyspiro[cyclohexane-1,2'-inden]-1'(3'H)-one (60 mg, 4%).

Example I-2

Synthesis of Intermediate A—Method 2

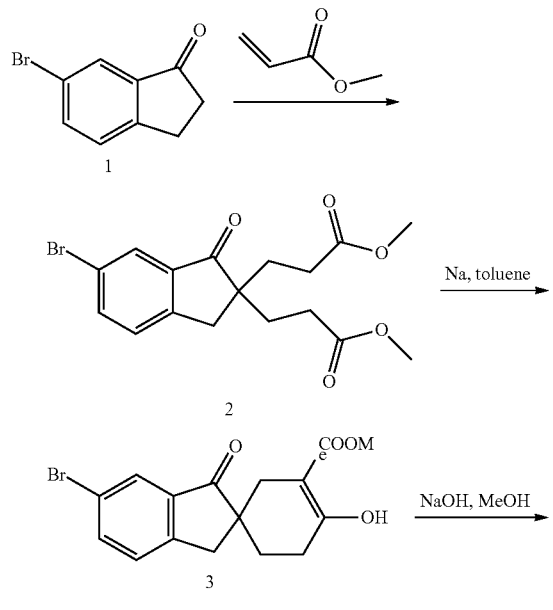

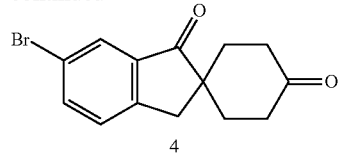

Step 1. Synthesis of dimethyl 3,3'-(6-bromo-1-oxo-2,3-dihydro-1H-indene-2,2-diyl)dipropanoate Under N$_2$, triton B (benzyl(tri-methyl)-ammonium hydroxide, 40% in MeOH, 2.48 mL) was added to a solution of 6-bromo-indan-1-one (26.1 g, 0.124 mol) in toluene (200 mL), and the mixture was stirred at 50° C. for 10 minutes. Acrylic methyl ester (31 mL, 0.286 mol) was added at 50° C., and the mixture was stirred at 50° C. overnight. After being cooled to room temperature, the mixture was poured into water (150 mL), and extracted with DCM (100 mL×4). The combined organic phases were dried over Na$_2$SO$_4$, and evaporated, and purified by column chromatography on silica gel (PE/EA=10:1) to give the compound 2 (39 g, 83%) as a yellow oil. $^1$H NMR (G000044883 692-154-1A CDCl$_3$ 400 MHz): δ 7.75-7.81 (s, 1H), 7.55-7.58 (d, 1H), 7.22-7.28 (d, 1H), 3.51-3.55 (s, 3H), 2.85-2.99 (s, 2H), 2.10-2.25 (m, 4H), 1.80-1.95 (m, 4H).

Step 2. Synthesis of methyl 6'-bromo-4-hydroxy-1'-oxo-1,3'-dihydrospiro[cyclohex[3]ene-1,2'-indene]-3-carboxylate A solution of compound 2 (34 g, 88.7 mmol) in toluene (400 mL) was added dropwise to a flask containing Na (2.24 g, 97.6 mmol) and dry toluene (100 mL) at refluxing at 120° C. The reaction mixture was heated at 120° C. for 28 hours, cooled to room temperature, and poured into a mixture H$_2$O (370 mL) and 4N HCl solution (37 mL) to afford a white suspension. This mixture was extracted with AcOEt (100 mL×4), evaporated, and purified by column chromatography on silica gel (PE/EA=10:1) to give the compound 3 (22.11 g, 71%) as white solid. $^1$H NMR: (CDCl$_3$ 400 MHZ): δ12.1 (s, 1H), 7.82-7.85 (s, 1H), 7.61-7.65 (d, 1H), 7.22-7.25 (d, 1H), 3.60-3.65 (s, 3H), 2.91-2.85 (d, 2H), 2.35-2.50 (m, 3H), 2.10-2.15 (d, 1H), 1.90-2.01 (m, 1H), 1.50-1.52 (m, 1H).

Step 3. Synthesis of 6'-bromospiro[cyclohexane-1,2'-indene]-1',4(3'H)-dione

To a suspension of compound 3 (22.1 g, 63.0 mmol) in MeOH (221 mL) was added a solution of NaOH (10.20 g, 0.255 mol) in H$_2$O (331 mL) at room temperature. The reaction mixture was heated at 60° C. overnight. The solvent was removed in vacuo, and extracted with DCM (250 mL×3). The combined organic layer was dried over Na$_2$SO$_4$ and concentrated in vacuo to afford compound 4 (15.33 g, 83%) as a white solid, which was used for the next step directly without purification. $^1$H NMR: (CDCl$_3$ 400 MHz): δ7.84 (s, 1H), 7.65-7.60 (d, 1H), 7.31-7.35 (d, 1H), 3.09 (s, 2H), 2.61-2.65 (m, 2H), 2.80-2.90 (m, 2H), 2.10-2.15 (m, 2H), 1.75-1.84 (m, 2H).

Alternative method for synthesis of 6'-bromospiro[cyclohexane-1,2'-indene]-1',4(3'H)-dione

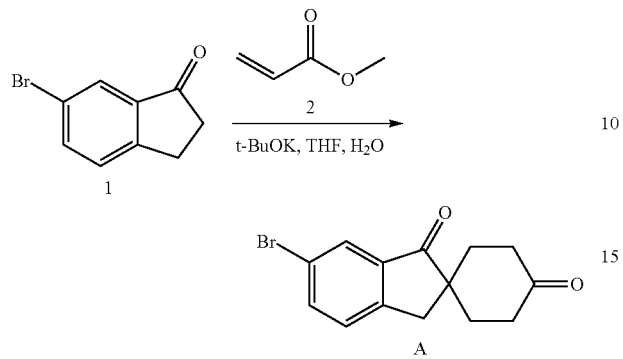

A

To a solution of compound 1 (20 g, 95 mmol) and methyl acrylate (18 g, 201 mmol) in anhydrous THF (200 mL) was added t-BuOK (16 g, 114 mmol) portionwise at room temperature. The reaction mixture was stirred at room temperature for 1 hour. Water (400 mL) and KOH (5.32 g, 95 mmol) were added. The resulting mixture was heated to reflux overnight. 3 N HCl (150 mL) was added and extracted with $CH_2Cl_2$ (500 mL×2). The organic layers were washed with $NaHCO_3$ (150 mL), brine (150 mL) and dried over $Na_2SO_4$, concentrated in vacuo to give compound A as a grey solid (23 g, 83% yield), which was used for next step without purification. $^1$H NMR (300 MHz, $CDCl_3$) δ 7.84 (s, 1H), 7.60-7.71 (d, 1H), 7.25-7.36 (d, 1H), 3.11 (s, 2H), 2.60-2.71 (m, 2H), 2.35-2.46 (m, 2H), 2.10-2.23 (m, 2H), 1.75-1.87 (m, 2H)

Alternative method for synthesis of 6'-bromospiro[cyclohexane-1,2'-indene]-1',4(3'H)-dione

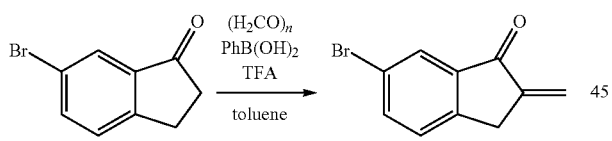

Step 1.
6-bromo-2-methylene-2,3-dihydro-1H-inden-1-one

A solution of 6-bromo-2,3-dihydro-1H-inden-1-one (0.3 g, 1.36 mmol), paraformaldehyde (0.4 g, 13.6 mmol), phenylboronic acid (0.2 g, 1.64 mmol) and trifluoroacetic acid (0.1 mL, 0.15 g, 1.36 mmol) in dry toluene (10 mL) was refluxed for 5 hours. When starting material was totally consumed, the crude mixture was cooled to room temperature, neutralized with saturated aqueous $Na_2CO_3$, extracted with ethyl acetate, dried and concentrated under reduced pressure. The residue was purified by flash column chromatography (silica gel, petroleum ether-ethyl acetate, 95:5) to give compound 6-bromo-2-methylene-2,3-dihydro-1H-inden-1-one (89 mg, 30%) as a white solid. $^1$H NMR ($CDCl_3$, 400 MHz): 3.71 (s, 2H), 5.68 (s, 1H), 6.39 (s, 1H), 7.38-7.40 (d, 1H), 7.70-7.72 (d, 1H), 7.99 (s, 1H).

Step 2. Preparation of 6'-bromospiro[cyclohexane-1,2'-indene]-1',4(3'H)-dione

In a flame dried 20 mL vial was placed 6-bromo-2-methylene-2,3-dihydro-1H-inden-1-one (98 mg, 0.441 mmol) and it was dissolved in dichloromethane (4.5 mL). To this solution was added 2-trimethylsilyloxy-1,3-butadiene (98 μL, 0.565 mmol) and the solution was cooled down to −78° C. After stirring for 5 minutes, $BF_3.OEt_2$ (27 mL, 0.219 mmol) was slowly added. After 5 minutes of the $BF_3.OEt_2$ addition, TLC indicated consumption of the dienophile. The reaction was quenched with MeOH (300 μL), allowed to stir for 5 minutes at −78° C. and then warmed up to room temperature. Once at room temperature, 2M HCl (7 mL) was added. The phases were separated and the aqueous phase was back-extracted with dichloromethane twice (5 mL/each). The combined organic phases were dried over $MgSO_4$, filtered and concentrated under reduce pressure. The crude material was purified by flash chromatography (ISCO, 12 g $SiO_2$ cartridge, ethyl acetate/hexanes as the eluents). The corresponding fractions were combined and concentrated under reduce pressure yielding 6'-bromospiro[cyclohexane-1,2'-indene]-1',4(3'H)-dione (62 mg, 0.212 mmol, 48% yield). $^1$H NMR=($CDCl_3$, 400 MHz) δ 7.68 (d, J=2.0 Hz, 1H), 7.51 (dd, J=8.0, 2.0 Hz, 1H), 7.16 (d, J=8.0 Hz, 1H), 2.94 (s, 2H), 2.48 (dt, J=15.2, 5.6 Hz, 2H), 2.22 (ddd, J=15.2, 10.8, 5.6 Hz, 2H), 1.98 (ddd, J=13.6, 11.2, 5.2 Hz, 2H), 1.65 (m, 2H) ppm.

Step 4. Synthesis of (trans-6'-bromo-4-hydroxyspiro[cyclohexane-1,2'-inden]-1'(3'H)-one

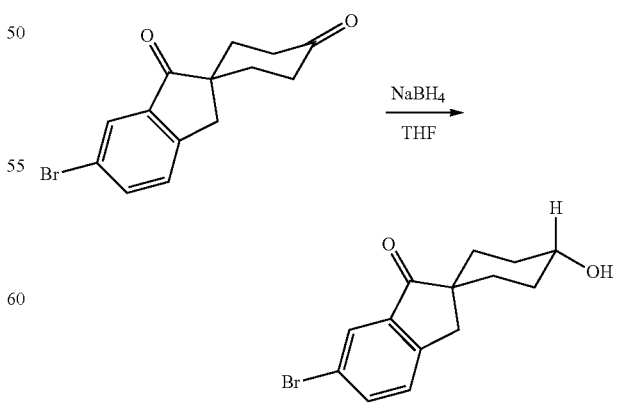

To a 20 mL vial was added 6'-bromospiro[cyclohexane-1,2'-indene]-1',4(3'H)-dione (102 mg, 0.349 mmol) and it was dissolved in THF (3.49 mL). This solution was cooled down to −78° C. and stirred for 5 minutes at that temperature. Then, NaBH$_4$ (7 mg, 0.184 mmol) were added at −78° C. After 10 minutes more NaBH$_4$ (7 mg, 0.184 mmol) was added. After 5 minutes, LC/MS showed ~70% conversion. Finally, a final portion of NaBH$_4$ (10 mg, 0.263 mmol) was added. After 5 minutes, TLC showed total consumption of the diketone. The excess NaBH$_4$ was quenched immediately with acetone (300 μL). After stirring for 15 minutes at −78° C., the reaction was warmed to room temperature and ethyl acetate (7 mL) and water (7 mL) were added. The phases were separated and the aqueous phase was back-extracted with ethyl acetate twice (5 mL/each). The combined organic phases were washed with brine, dried over MgSO$_4$, filtered and concentrated under reduce pressure. The crude material was purified by flash chromatography (ISCO, 12 g SiO$_2$ cartridge, ethyl acetate/hexanes as the eluents). The fractions corresponding to the isomer shown in the scheme were combined and concentrated under reduce pressure yielding trans-6'-bromo-4-hydroxyspho[cyclohexane-1,2'-inden]-1'(3'H)-one (71 mg, 0.241 mmol, 69% yield) as a colorless oil. M+H=294.9, 296.9; $^1$H NMR=(CDCl$_3$, 400 MHz) δ 7.84 (bs, 1H), 7.67 (dd, J=8.0, 2.0 Hz, 1H), 7.32 (d, J=8.0 Hz, 1H), 3.73 (m, 1H), 2.96 (s, 2H), 2.04 (m, 2H), 1.94 (s, 1H), 1.77 (m, 2H), 1.47-1.40 (m, 4H) ppm.

Step 5. Synthesis of Intermediate A: trans-6'-bromo-4-methoxyspiro[cyclohexane-1,2'-inden]-1'(3'H)-one

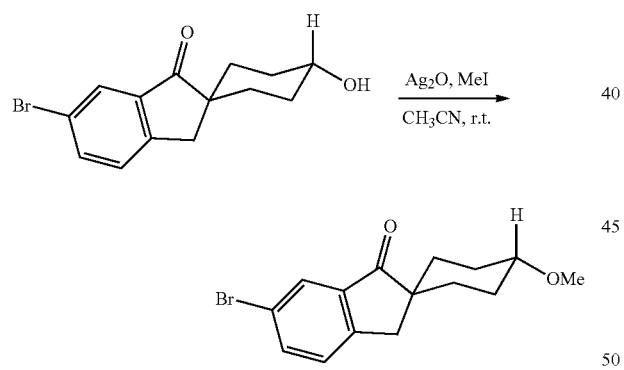

In a 4 mL vial was placed 6'-bromo-4-hydroxyspiro[cyclohexane-1,2'-inden]-1'(3'H)-one (5 mg, 0.017 mmol) and acetonitrile (150 μL) was added. To this solution were added silver oxide (27 mgs, 0.117 mmol), freshly grinded Drierite (~100 mgs of fine white powder) and methyl iodide (48 μL, 0.769 mmol), in that particular order. The vial was capped and the reaction allowed stir at room temperature overnight (~14 hours). The next morning, LC/MS indicated total consumption of the alcohol. The reaction was filtered thru a pad of celite, and the pad was washed with ethyl acetate (4 mL). The filtrate was concentrated under reduced pressure yielding 3 mgs of the desired product. $^1$H NMR confirms the structure as well as LC/MS.

Example 1

Synthesis of Compound 1

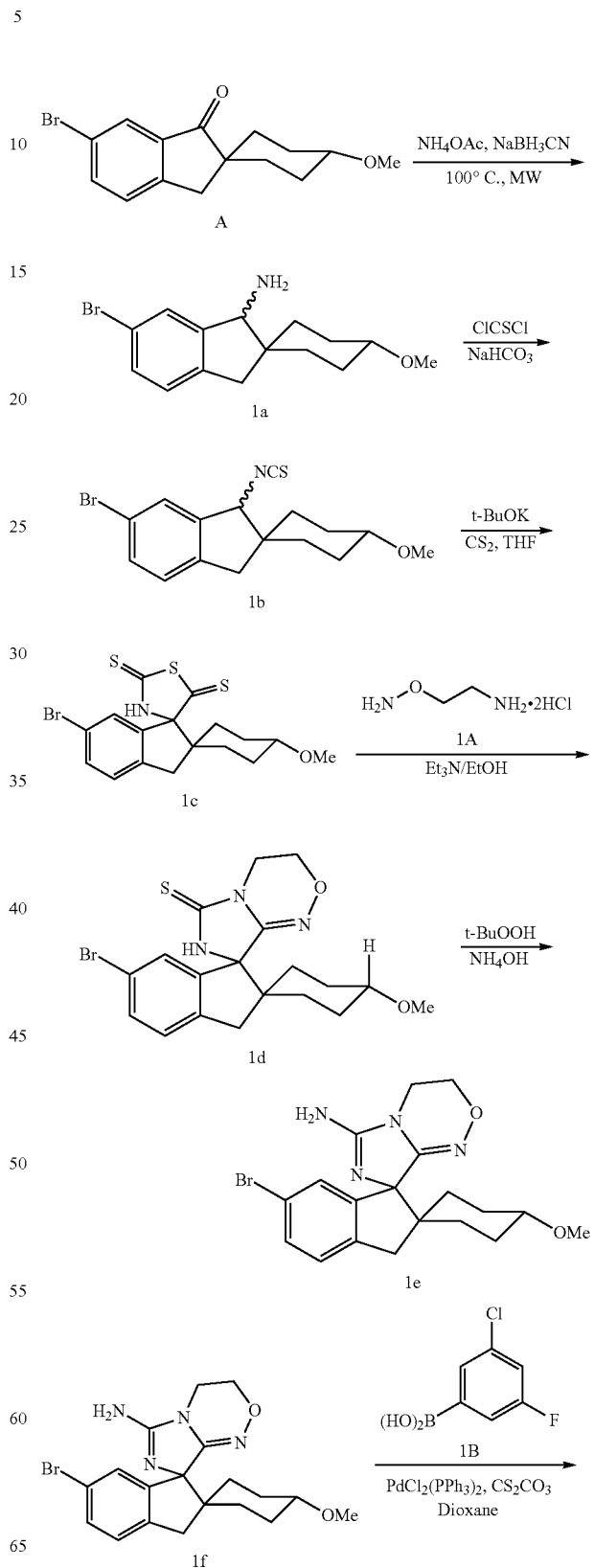

-continued

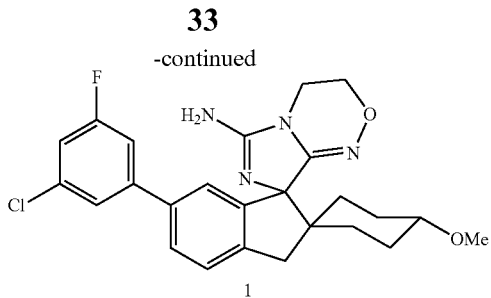

1

Step 1: Synthesis of 6'-bromo-4-methoxy-1',3'-dihydrospiro[cyclohexane-1,2'-inden]-1'-amine (1b)

To a solution of compound A (0.51 g, 1.73 mmol) in MeOH (5 mL) was added $NH_4OAc$ (1.33 g, 17.3 mmol) and $NaBH_3CN$ (0.13 g, 2.1 mmol) at room temperature. After addition, the mixture was stirred in microwave at 110° C. for 90 min. TLC showed that the reaction was completed. The reaction mixture was concentrated in vacuo to give the residue, which was dissolved in ethyl acetate (25 mL) and washed with 2 N HCl (10 mL), aqueous was added 2 N NaOH (12 mL) and was extracted with ethyl acetate (25 mL×2) to give compound 1a (0.28 g, 52%) as a white solid.

$^1$H NMR (CDCl$_3$ 400 MHz): δ 7.35 (s, 1H), 7.21-7.27 (m, 1H), 6.96-6.98 (d, J=7.6 Hz, 1H), 3.83 (s, 1H), 3.29 (s, 3H), 3.04-3.11 (m, 1H), 2.81-2.85 (m, 1H), 2.44-2.48 (m, 1H), 1.86-1.98 (m, 2H), 1.53-1.56 (m, 2H), 1.23-1.32 (m, 2H), 1.16-1.21 (m, 2H).

Step 2: Synthesis of 6'-bromo-1'-isothiocyanato-4-methoxy-1',3'-dihydrospiro[cyclohexane-1,2'-indene] (1b)

A mixture of compound 1a (0.28 g, 0.9 mmol) in methylene chloride (10 mL) and saturated aqueous sodium bicarbonate (10 mL) was cooled with an ice bath, treated with thiophosgene (0.12 g, 1.0 mmol), stirred vigorously for 30 min, TLC showed that the reaction was completed, diluted with methylene chloride (30 mL). The phases were separated. The organic phase was washed with brine (30 mL), dried over sodium sulfate and concentrated to dryness to give compound 1b (0.25 g, 79%) as a white oil, which was used directly for the next step without purification.

Step 3: Synthesis of (E)-N-(5'-bromo-5,6,8,9-tetrahydrospiro[benzo[7]annulene-7,2'-inden]-3'(1'H)-ylidene)-2-methylpropane-2-sulfinamide (1c)

A mixture of potassium t-butoxide (84.5 mg, 0.78 mmol) in THF (5 mL) at −78° C. was slowly added over a period of 2 min to a solution of compound 1b (0.25 g, 0.71 mmol) and carbon disulfide (81 mg, 1.065 mmol) in THF (5 mL). After addition, the reaction mixture was stirred at −78° C. for 0.5 h, then slowly warmed to room temperature and stirred for 1 h. The reaction mixture was partitioned between with methylene chloride (20 mL) and water (20 mL). The phases were separated. The organic phase was washed with brine (15 mL), dried over sodium sulfate and concentrated to dryness to give compound 1c (0.25 g, 82%) as a white solid, which was used directly for the next step without purification.

Step 4: Synthesis of (E)-N-(5'-bromo-5,6,8,9-tetrahydrospiro[benzo[7]annulene-7,2'-inden]-3'(1'H)-ylidene)-2-methylpropane-2-sulfinamide (1d)

A mixture of compound 1c (140 mg, 0.33 mmol), compound 1A (146 mg, 0.98 mmol) and triethylamine (217 mg, 2.15 mmol) in ethanol (10 mL) was stirred at ice bath temperature for 2 h, warmed to room temperature, stirred at room temperature for 24 h and heated to 70° C. for 2 h. After cooling to room temperature, the solution was concentrated under reduced pressure. The residue was partitioned between EtOAc and water, the organic phase was washed sequentially with 1 N aq. HCl and brine (10 mL), dried over $Na_2SO_4$ and concentrated under reduced pressure to give compound 1d (80 mg, 56%) as a white solid, which was purified by preparative TLC (hexanes:EtOAc=5:1).

Step 5: synthesis of (E)-N-(5'-bromo-5,6,8,9-tetrahydrospiro[benzo[7]annulene-7,2'-inden]-3'(1'H)-ylidene)-2-methylpropane-2-sulfinamide (1e)

A mixture of compound 1d (80 mg, 0.18 mmol) and t-butyl hydroperoxide (508 mg of a 65% solution in water, 3.6 mmol) in methanol (10 mL) and concentrated aqueous ammonium hydroxide (2 mL) was stirred at room temperature overnight. The reaction mixture was treated with 10% aqueous sodium thiosulfate (8 mL) and concentrated under reduced pressure to remove most of the methanol. The resulting aqueous mixture was extracted with methylene chloride (20 mL×2). The combined organic layers were washed with brine (20 mL), dried over $Na_2SO_4$ and concentrated to dryness. Purification of this residue by pre-TLC afforded compound 1e (40 mg, 52%) as a white solid.

Step 6: Synthesis of Compound 1

Compound 1e (20 mg, 0.048 mmol) under a nitrogen atmosphere was treated sequentially with compound 1B (16.6 mg, 0.096 mmol) in 1,4-dioxane (2 mL), $Cs_2CO_3$ (2 M, 0.072 mL) and $Pd(PPh_3)_2Cl_2$ (5 mg). The mixture was heated to reflux for 15 min. TLC showed that the reaction was completed. The reaction mixture was concentrated in vacuo to give the residue, which was purified by pre-TLC and pre-HPLC to give compound 1 (1.9 mg, yield 8.6%) as a white solid.

$^1$H NMR (CD$_3$OD 400 MHz): δ 7.40-7.43 (dd, J=1.2, 4.0 Hz, 1H), 7.34 (s, 1H), 7.25-7.27 (d, J=7.6 Hz, 1H), 7.17-7.21 (m, 2H), 7.03-7.05 (m, 1H), 3.63-3.82 (m, 4H), 3.38 (s, 3H), 2.90-3.07 (m, 3H), 1.83-1.93 (m, 3H), 1.53-1.59 (m, 1H), 1.15-1.30 (m, 4H).

LC-MS $t_R$=1.015 min in 2 min chromatography, MS (ESI) m/z 469 [M+H]$^+$

Example 2

Synthesis of Compound 2

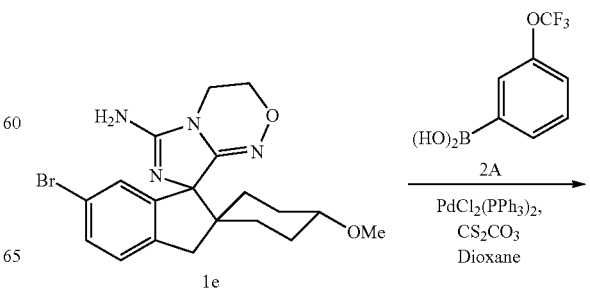

-continued

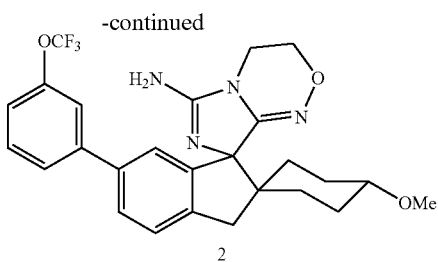

2

Starting with intermediate 1e (10 mg, 0.048 mmol) from Example 1, compound 1e was reacted with 3-triluoromthoxy phenylboronate as described in step 6 of example 1. The crude product was purified by preparative TLC (CH$_2$Cl$_2$: MeOH=10:1) and HPLC to give compound 2 (1.6 mg, 6.7%) as a white solid.

$^1$H NMR (CD$_3$OD 400 MHz): δ 7.47-7.49 (d, J=7.6 Hz, 1H), 7.35-7.42 (m, 3H), 7.26-7.27 (d, J=7.6 Hz, 1H), 7.12-7.18 (m, 2H), 3.65-3.82 (m, 4H), 3.25 (s, 3H), 2.90-3.07 (m, 3H), 1.85-1.95 (m, 3H), 1.52-1.59 (m, 1H), 1.20-1.32 (m, 4H).

LC-MS t$_R$=1.035 min in 2 min chromatography, MS (ESI) m/z 501 [M+H]$^+$

Example 3

Synthesis of Compound 3

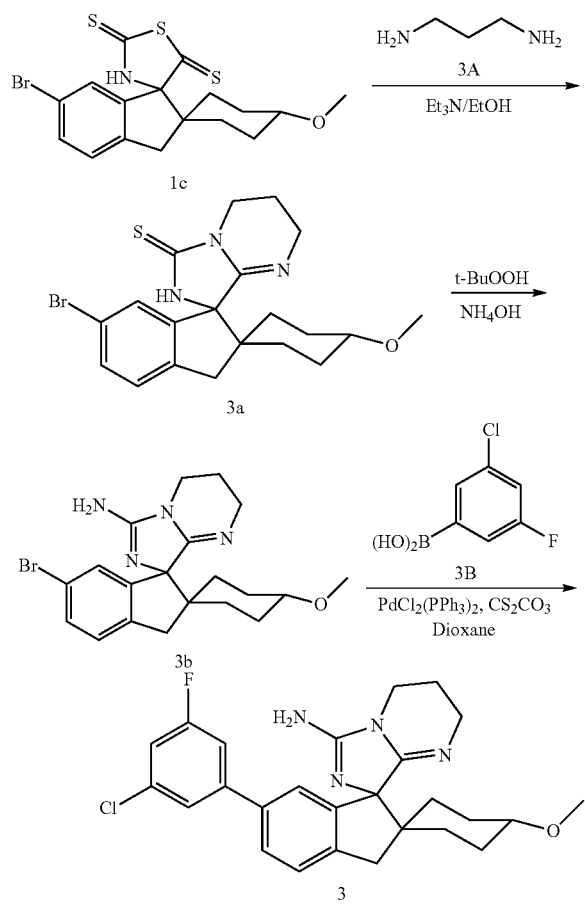

This was synthesized as described in Example 1, step 4. 1,3-propylenediamine was utilized instead of O-(2-aminoethyl)hydroxylamine and was further elaborated as in Example 1 to give final compound that was purified by pre-TLC (CH$_2$Cl$_2$:MeOH=5:1) and pre-HPLC to give compound 3 (97.3 mg) as a white solid.

LC-MS t$_R$=1.102 min in 2 min chromatography, MS (ESI) m/z 467.2 [M+H]$^+$.

$^1$H NMR (CD$_3$OD 400 MHz): δ 7.45-7.48 (d, J=8.0 Hz, 1H), 7.38 (s, 1H), 7.31-7.33 (d, J=7.6 Hz, 1H), 7.22-7.26 (d, J=8.0 Hz, 1H), 7.20 (s, 1H), 7.07-7.11 (d, J=8.4 Hz, 1H), 3.55-3.58 (m, 2H), 3.27 (s, 3H), 3.19-3.23 (m, 1H), 3.00-3.09 (m, 4H), 1.91-2.00 (m, 3H), 1.74-1.76 (m, 2H), 1.58-1.59 (m, 1H), 1.24-1.35 (m, 4H).

Example 4

Synthesis of Compound 4

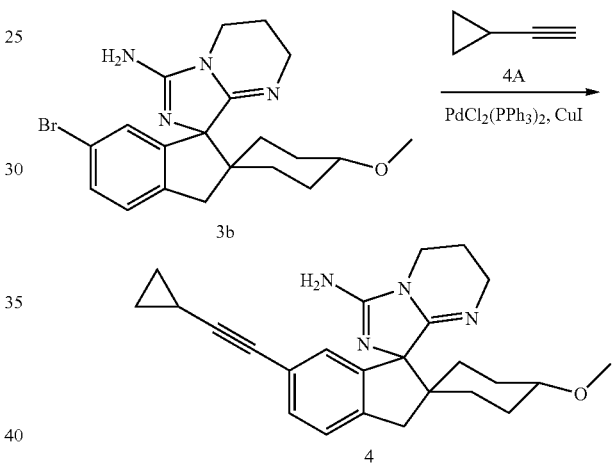

The intermediate 3b from Example 3 (50 mg, 0.12 mmol) was dissolved in Et$_3$N (5 mL) and Et$_2$NH (1 mL), the resulting mixture was degassed and purged with N$_2$ for three times. PdCl$_2$(PPh$_3$)$_2$ (5 mg) and CuI (4 mg) were added under nitrogen and the system was degassed again. Ethynylcyclopropane (0.5 mL, excess) was added by syringe. The system was degassed one more time. The reaction was heated to 50~60° C. for 12 h. LCMS showed that the reaction was completed; the solvent was removed under reduced pressure. The residue was partitioned by CH$_2$Cl$_2$ (10 mL) and water (10 mL). The aqueous layer was extracted with CH$_2$Cl$_2$ (2×10 mL), the combined organic layers were washed with brine (2×10 mL), dried over anhydrous Na$_2$SO$_4$ and concentrated to dryness. Purification of this residue by preparative TLC (CH$_2$Cl$_2$: MeOH=5:1) and pre-HPLC to afforded compound 4 (3.5 mg, 7%) as a white solid.

LC-MS t$_R$=1.041 min in 2 min chromatography, MS (ESI) m/z 403.2 [M+H]$^+$.

$^1$H NMR (CD$_3$OD 400 MHz): δ 7.19-7.24 (q, 2H), 7.00 (s, 1H), 3.61-3.66 (m, 2H), 3.35 (s, 3H), 3.23-3.28 (m, 2H), 3.14-3.15 (m, 1H), 2.97-3.02 (m, 2H), 1.96-2.04 (m, 3H), 1.80-1.83 (m, 2H), 1.57-1.58 (m, 1H), 1.19-1.45 (m, 5H), 0.84-0.88 (m, 2H), 0.68-0.71 (m, 2H).

Example 5

Synthesis of Compound 5

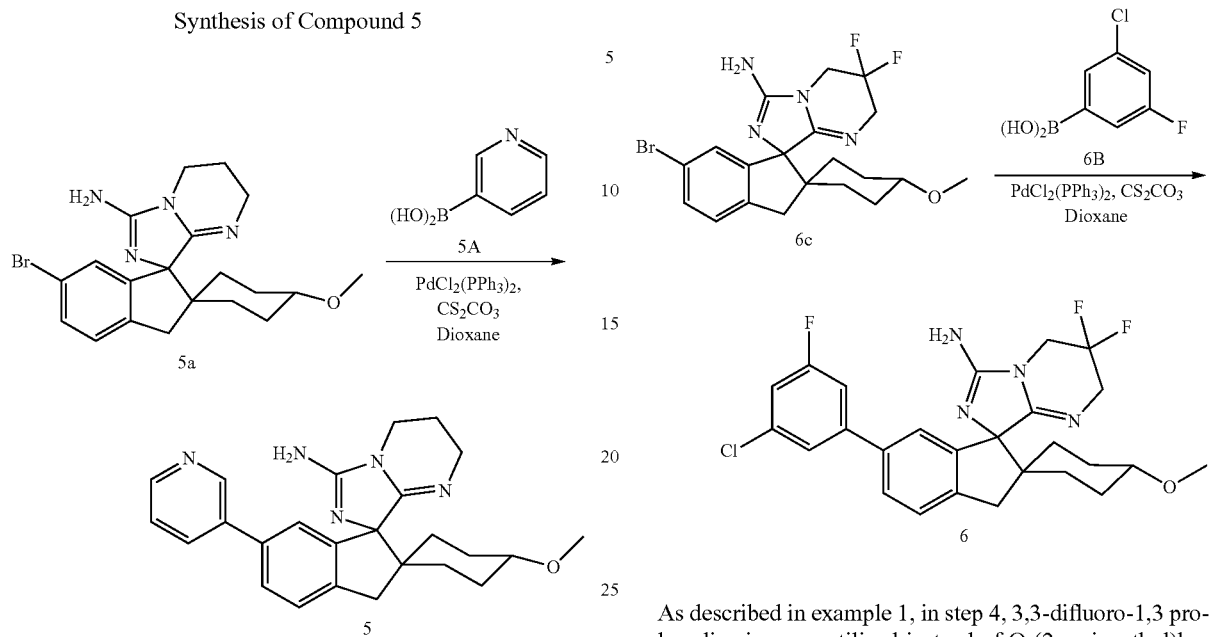

This was synthesized by method described in Example 2. 3-pyridylboronate was utilized instead of trifluromethoxy phenylboroante. The crude product was purified by preparative TLC (CH$_2$Cl$_2$:MeOH=5:1) and preparative HPLC to afford product compound 5 (3.2 mg, 8%) as a white solid.

LC-MS t$_R$=1.178 min in 2 min chromatography, MS (ESI) m/z 416.2 [M+H]$^+$.

$^1$H NMR (CD$_3$OD 400 MHz): δ 8.76 (s, 1H), 8.49-8.51 (d, J=4.8 Hz, 1H), 8.06-8.09 (dd, J=8.0 Hz, 1H), 7.57-7.59 (d, J=8.0 Hz, 1H), 7.49-7.53 (t$_R$ J=8.0 Hz, 1H), 7.42-7.44 (d, J=7.6 Hz, 1H), 7.33 (s, 1H), 3.63-3.68 (m, 2H), 3.38 (s, 3H), 3.05-3.29 (m, 5H), 1.99-2.07 (m, 3H), 1.81-1.85 (m, 2H), 1.63-1.66 (t, J=12.0 Hz, 1H), 1.30-1.43 (m, 4H).

Example 6

Synthesis of Compound 6

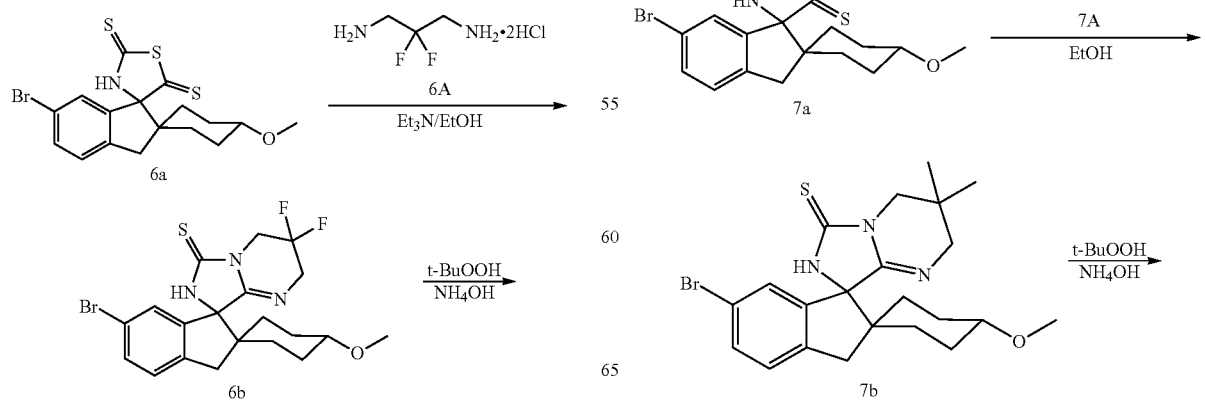

As described in example 1, in step 4, 3,3-difluoro-1,3 propylenediamine was utilized instead of O-(2-aminoethyl)hydroxylamine and was further elaborated as in example 1 to yield product (0.35 g) as a white solid.

LC-MS t$_R$=1.188 min in 2 min chromatography, MS (ESI) m/z 503.2 [M+H]$^+$.

$^1$H NMR (CD$_3$OD 400 MHz): δ 7.42-7.44 (d, J=7.6 Hz, 1H), 7.33 (s, 1H), 7.27-7.29 (d, J=8.0 Hz, 1H), 7.18-7.21 (d, J=8.4 Hz, 2H), 7.04-7.07 (d, J=10.8 Hz, 1H), 3.79-3.86 (m, 2H), 3.29-3.57 (m, 2H), 3.25 (s, 3H), 2.93-3.07 (m, 3H), 1.87-1.94 (m, 3H), 1.50-1.54 (t, J=15.2 Hz, 1H), 1.17-1.34 (m, 4H).

Example 7

Synthesis of Compound 7

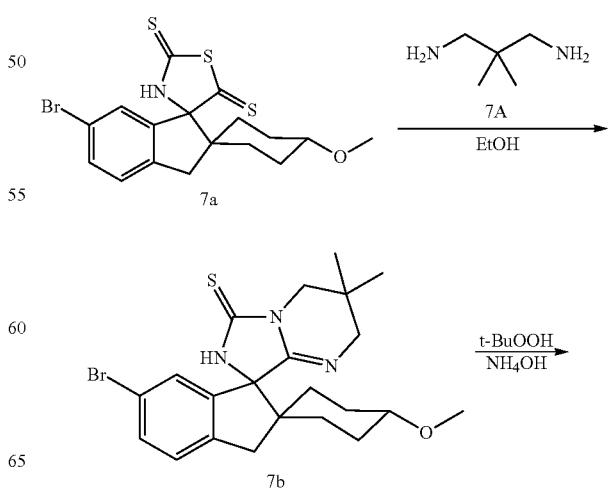

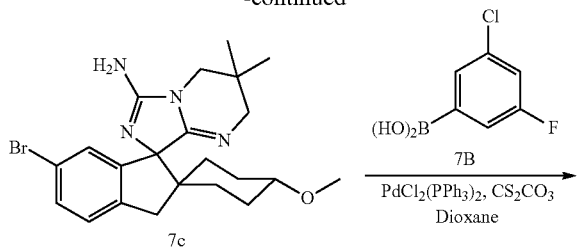

As described in example 1, step 4,2,2-dimethylpropane-1,3-diamine was utilized instead of O-(2-aminoethyl)hydroxylamine and was further elaborated to yield example 5 as a white solid.

LC-MS $t_R$=1.156 min in 2 min chromatography, MS (ESI) m/z 495.2 [M+H]$^+$.

$^1$H NMR (CD$_3$OD 400 MHz): δ 7.45-7.47 (d, J=7.6 Hz, 1H), 7.33-7.38 (t, J=10.0 Hz, 2H), 7.16-7.24 (m, 2H), 7.05-7.07 (d, J=8.4 Hz, 1H), 3.26 (s, 3H), 3.07-3.15 (m, 3H), 2.95-3.04 (m, 4H), 1.84-1.94 (m, 2H), 1.74-1.79 (m, 1H), 1.54-1.60 (t, J=11.6 Hz, 1H), 1.14-1.33 (m, 4H), 0.94 (s, 6H).

Example 8

Synthesis of Compound 8

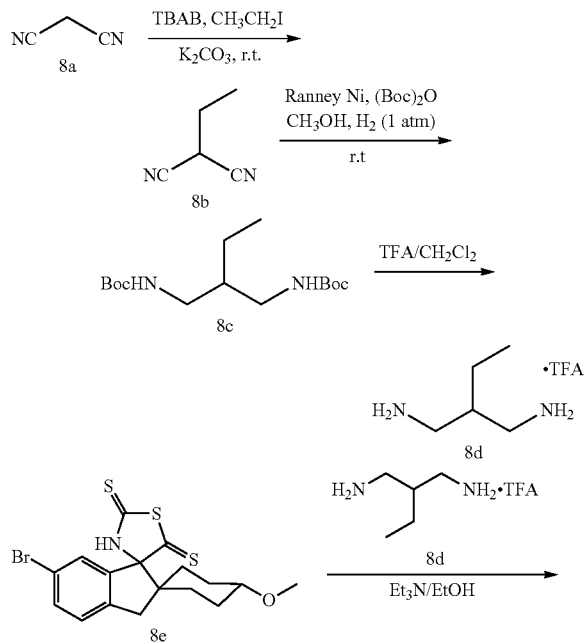

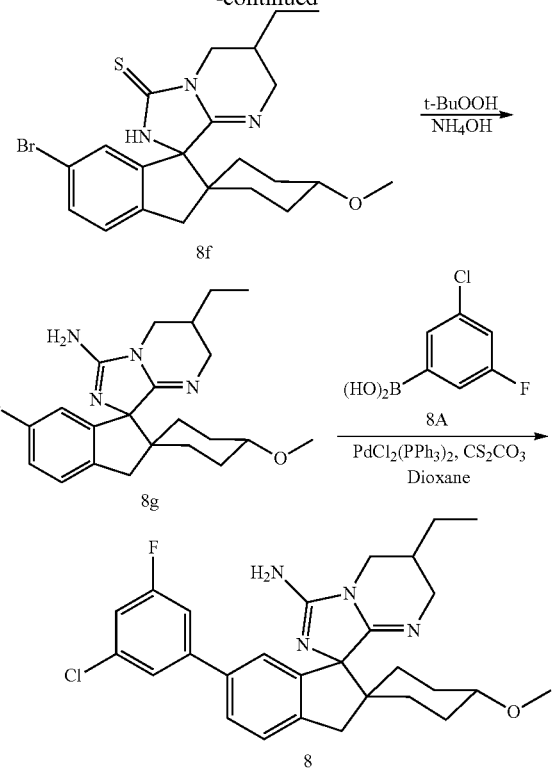

Step 1 Synthesis of 2-Ethylmalononitrile

To a round bottle flask was added compound 8a (15 g, 227 mmmol), tetrabutylammonium bromide (2.9 g, 9 mmol) and ethyl idodide (17.7 g, 113 mmol). The reaction mixture was stirred at 20° C. for 30 min and then cooled to 0° C. K$_2$CO$_3$ (15.6 g, 113 mmol) was added slowly to the mixture. The reaction mixture was then warmed up to 20° C. and kept stirring for 30 min. The mixture was partitioned between water (300 mL) and CH$_2$Cl$_2$ (400 mL). The organic fractions were collected, dried over MgSO$_4$ and concentrated under reduced pressure and the residue was purified by column chromatography on silica gel eluting with 10% EtOAc in hexane to afford compound 8b (5.9 g, 28%) as a yellow oil.

$^1$HNMR (DMSO-d$_6$, 400 MHz) δ 4.72-4.77 (m, 1H), 1.94-1.98 (m, 2H), 1.04-1.09 (m, 3H).

Step 2 Synthesis of tert-butyl 2-ethylpropane-1,3-diyldicarbamate

A round bottom flask was charged with compound 8b (5.0 g, 53 mmol), (Boc)$_2$O (35 g, 160 mmol), Ranney Ni (5 g) and CH$_3$OH (80 mL). The reaction mixture was stirred at room temperature under H$_2$ atmosphere (1 atm) overnight. The mixture was filtrated and the filtrate was concentrated under vacuum. The residue was purified by column (petroleum ether:ethyl acetate=2:1) to give compound 8c (3.4 g, 22%) as a yellow oil, which was used directly for the next step without further purification.

Step 3: Synthesis of 2-ethylpropane-1,3-diamine as bis TFA salt

To a round bottle was dissolved compound 8c (0.5 g, 1.65 mmol) in a mixture of CH$_2$Cl$_2$ and TFA (10 mL, CH$_2$Cl$_2$:

TFA=4:1). The reaction mixture was stirred at 20° C. for 30 min. The reaction solvent was removed under vacuum to afford crude compound 8d (0.34 g, crude) as a yellow oil, which was used for the next step directly without further purification.

$^1$HNMR (CD$_3$OD, 300 MHz) δ 3.00-3.06 (m, 3H), 2.04 (m, 1H), 1.54-1.58 (m, 2H), 1.00-1.04 (m, 3H).

This was further elaborated as described in example 1. As described in example 1, in step 4,2-ethylpropane-1,3-diamine was utilized instead of O-(2-aminoethyl)hydroxylamine and was further elaborated to yield compound 8 (89 mg) as a white solid.

LC-MS t$_R$=1.198 min in 2 min chromatography, MS (ESI) m/z 495.2 [M+H]$^+$.

$^1$H NMR (CD$_3$OD 400 MHz): δ 7.53-7.55 (d, J=8.0 Hz, 1H), 7.41-7.43 (d, J=7.6 Hz, 2H), 7.34-7.36 (d, J=8.0 Hz, 1H), 7.25-7.27 (d, J=7.6 Hz, 1H), 7.04-7.08 (d, J=8.0 Hz, 1H), 3.86-3.92 (m, 0.7H), 3.37-3.44 (m, 0.3H), 3.26-3.92 (s, 2H), 3.01-3.09 (m, 5H), 2.56 (s, 2H), 1.90-2.02 (m, 3H), 1.61-1.68 (m, 1H), 1.17-1.40 (m, 7H), 0.89-0.93 (t, J=7.2 Hz, 3H).

Example 9

Synthesis of Compound 9

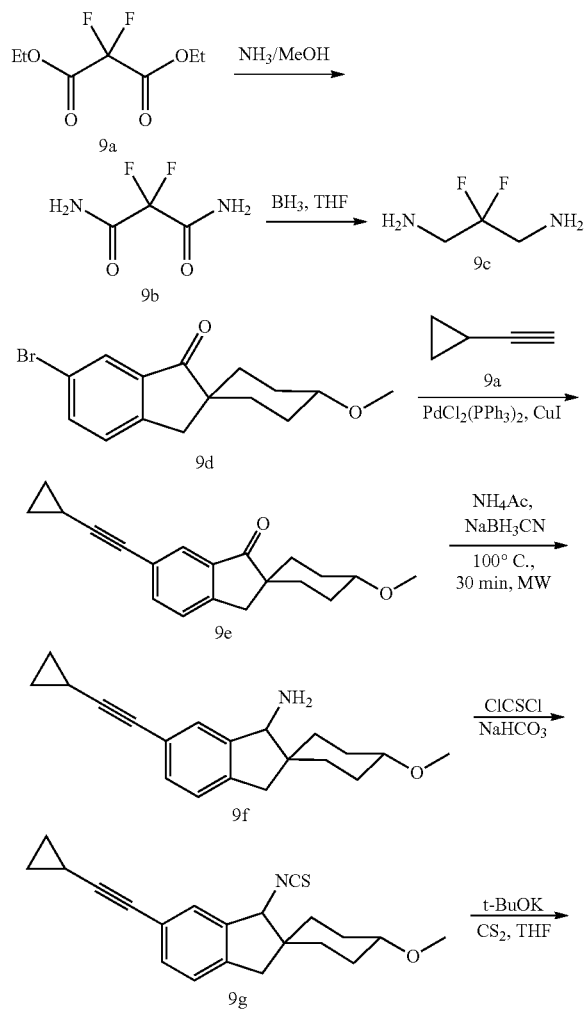

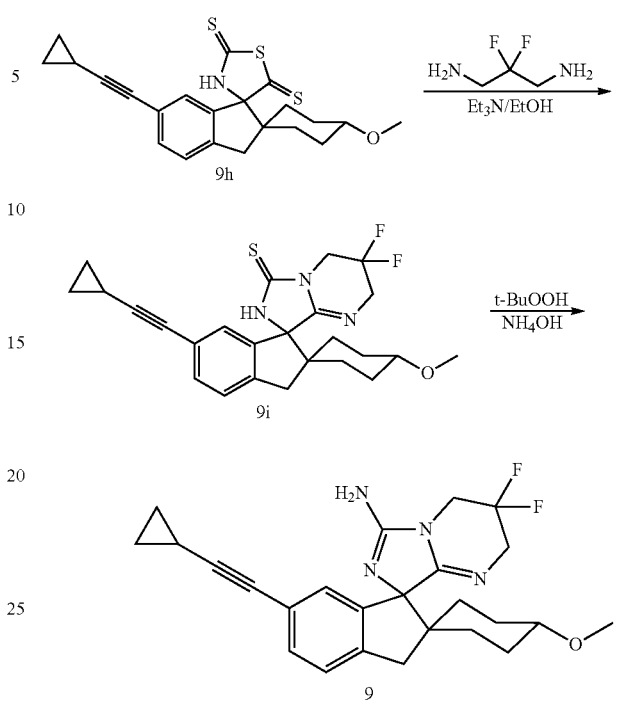

Step 1: Procedure for Preparation of Compound 9b

To a solution of NH$_3$/MeOH (sat., 50 mL) was added compound 9a (5 g, 25.5 mmol) at −78° C. and stirred at this temperature for 2 h. Then the reaction mixture was allowed to warm to room temperature slowly and stirred overnight. The reaction mixture was concentrated under reduced pressure to dryness to give compound 9b (3.3 g, 94%) as a white solid.

$^1$H NMR (DMSO-d$_6$ 400 MHz): δ 8.24 (br, 2H), 8.09 (br, 2H).

Step 2: Procedure for Preparation of Compound 9c

To a solution of BH$_3$-THF (1 M in THF, 101.5 mL, 101.5 mmol) was added slowly compound 9b (2.8 g, 20.3 mmol) at ~0° C. cooled under an ice bath. The resulting mixture was stirred at this temperature till the reaction mixture turned clear. Then the solution was heated at reflux overnight. The mixture was cooled under an ice bath and MeOH (100 mL) was added dropwise. The resulting solution was concentrated to dryness and another 30 mL of MeOH was added. The solvent was removed again. This process was repeated for 3 times. Then to the residue was added a solution of HCl/MeOH (4 N, 30 mL) slowly and a lot of white solid was precipitated. The solid was collected by filtration and washed with EtOH (5 mL), dried under reduced pressure to give compound 9c (1.59 g, 43%) as a white HCl salt.

$^1$H NMR (DMSO-d$_6$, 400 MHz): δ 8.83 (br, 6H), 3.61 (t, J=31.2 Hz, 4H).

Step 3: Procedure for Preparation of Compound 9e

Compound 9d (3.6 g, 11.6 mmol) was dissolved in Et$_3$N (50 mL) and Et$_2$NH (10 mL), the resulting mixture was degassed and purged with N$_2$ for three times. Pd(PPh$_3$)$_2$Cl$_2$ (400 mg) and CuI (120 mg) were added under a nitrogen atmosphere atmosphere and the system was degassed again. Ethynylcyclopropane (6 mL, excess) was added by syringe. The system was degassed one more time. The reaction was heated at 50-60° C. for 12 h. LCMS showed that the reaction was completed; solvent was removed under reduced pressure. The residue was partitioned by CH$_2$Cl$_2$ (100 mL) and water (100 mL). The aqueous layer was extracted by CH$_2$Cl$_2$ (2×100 mL), the combined organic layers were washed with brine (2×100 mL), dried over Na$_2$SO$_4$ and concentrated to dryness. Purification of this residue by column chromatography (petroleum ether:ethyl acetate=50:1 to 5:1) afforded compound 9e (3.45 mg, 100%) as a white solid.

Compound 9e was further elaborated as described in example 1 from step 1-5 to yield Compound 9 as a white solid.

LC-MS t$_R$=1.120 min in 2 min chromatography, MS (ESI) m/z 439.2 [M+H]$^+$.

$^1$H NMR (CD$_3$OD 400 MHz): δ 7.22-7.29 (q, J=8.4 Hz, 2H), 7.11 (s, 1H), 3.96-4.05 (m, 2H), 3.62-3.76 (m, 2H), 3.36 (s, 3H), 3.19-3.25 (m, 1H), 3.06 (s, 2H), 1.96-2.06 (m, 3H), 1.39-1.53 (m, 6H), 0.85-0.90 (m, 1H), 0.68-0.72 (m, 2H).

The crude product was purified by preparative TLC (CH$_2$Cl$_2$:MeOH=5:1) and preparative HPLC to afford product compound 9 (1.5 mg, 8%) as a white solid.

LC-MS t$_R$=0.876 min in 2 min chromatography, MS (ESI) m/z 452.2 [M+H]$^+$.

$^1$H NMR (CD$_3$OD 400 MHz): δ 8.76 (s, 1H), 8.51 (s, 1H), 8.06-8.08 (d, J=7.6 Hz, 1H), 7.59-7.61 (d, J=9.2 Hz, 1H), 7.50-7.53 (t, J=8.0 Hz, 1H), 7.43-7.45 (d, J=7.6 Hz, 1H), 7.36 (s, 1H), 3.92-4.00 (m, 2H), 3.50-3.70 (m, 2H), 3.37 (s, 3H), 3.07-3.27 (m, 3H), 1.96-2.07 (m, 3H), 1.62-1.65 (t, 1H), 1.29-1.48 (m, 4H).

Example 10

Synthesis of Compound 10

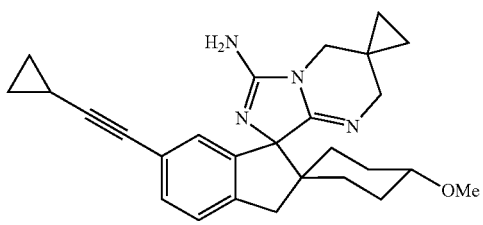 [SMILES: COC1CCC2(CC1)Cc1ccc(C#CC3CC3)cc1C21N=C(N)N2CC3(CC3)CN=C21]

This was synthesized by procedure described in example 9. Starting with Intermediate 9h from example 9, it was further elaborated as described in example 6 utilizing 1,1-bis(aminomethyl)cyclopropane.

The crude product was purified by preparative HPLC (acid) to give product compound 10 (0.6 mg, 1%) as a white solid (trifluroacetic salt).

LC-MS t$_R$=0.948 min in 2 min chromatography, MS (ESI) m/z 428.3 [M+H]$^+$.

$^1$H NMR (CD$_3$OD 400 MHz): δ 7.24 (m, 2H), 7.13 (s, 1H), 3.9 (s, 3H), 3.57-3.38 (m, 3H), 3.03 (m, 3H), 2.0-1.7 (m, 2H), 1.48-1.19 (m, 8H), 0.7-0.6 (m, 13H).

Example 11

Synthesis of Compound 11

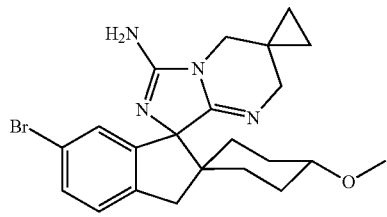 [SMILES: COC1CCC2(CC1)Cc1ccc(Br)cc1C21N=C(N)N2CC3(CC3)CN=C21]

This was synthesized by procedure described in example 3 for intermediate 3b. Starting with intermediate 1, it was further elaborated as described in example 7 utilizing 1,1-bis(aminomethyl)cyclopropane.

The crude product was purified by preparative TLC (CH$_2$Cl$_2$:MeOH=5:1) and preparative HPLC (basic) gave compound 11 (15 mg, 31%) as a white solid.

LC-MS t$_R$=1.028 min in 2 min chromatography, MS (ESI) m/z 443.1, 445.1 [M+H]$^+$.

$^1$H NMR (CD$_3$OD 400 MHz): δ 7.42-7.45 (d, J=8.0 Hz, 1H), 7.29 (s, 1H), 7.23-7.29 (d, J=8.0 Hz, 1H), 3.63-3.66 (d, J=11.6 Hz, 1H), 3.39 (s, 3H), 3.10-3.19 (m, 1H), 2.98-3.03 (m, 3H), 1.96-2.07 (m, 3H), 1.55-1.62 (m, 1H), 1.25-1.45 (m, 6H), 0.53-0.72 (m, 4H).

Example 12

Synthesis of Compound 12

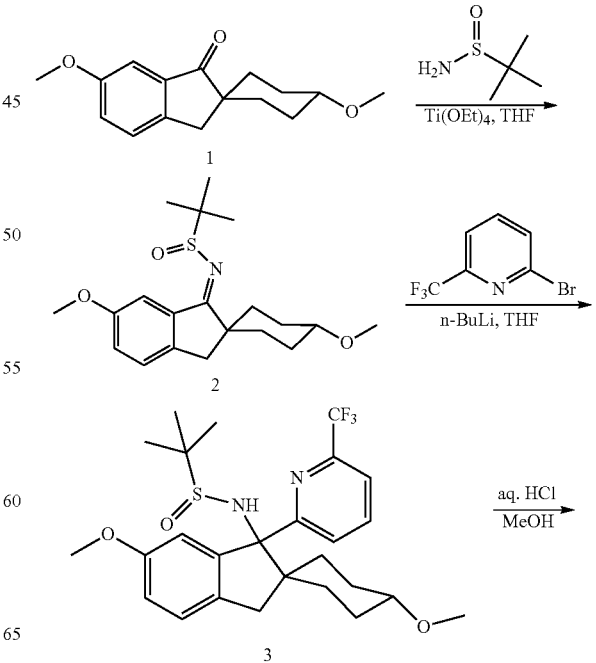

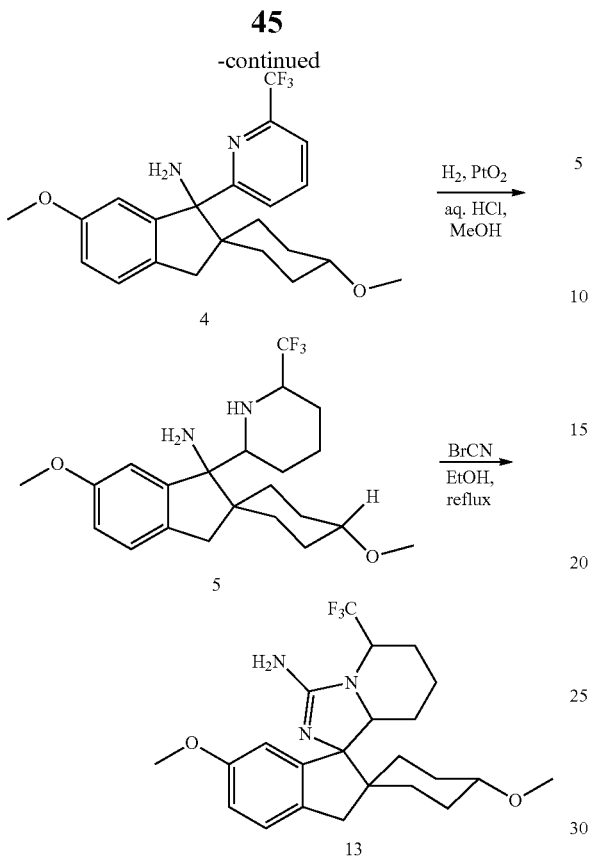

Procedure for Preparation of Compound 5

To a solution of compound 4 (20 mg, 0.057 mmol) in MeOH (10 mL) was added PtO$_2$ (5 mg) (the mixture was added drops of HCl/MeOH). The mixture was stirred at room temperature under a H$_2$ (30 Psi) atmosphere overnight. The reaction mixture was adjust to pH=8 with NH$_3$.H$_2$O, and evaporated under vacuum. The residue was dissolved in EtOAc (10 mL), and the solid was filtered off. The filtrate was evaporated to give crude compound 5 (20 mg, crude). The crude was used in the next step without further purification.

Procedure for Preparation of Compound 12

To a solution of compound 5 (20 mg, 0.049 mmol) in ethanol (3 mL) was added BrCN (10 mg). The solution was heated at 80° C. for 30 min in a microwave reactor. Then the solvent was evaporated under vacuum and the residue was purified by preparative HPLC to afford compound 12 (1.1 mg, 5%) as a white solid.

LC-MS t$_R$=1.494 min in 2 min chromatography, MS (ESI) m/z 438 [M+H]$^+$.

$^1$H NMR (CD$_3$OD 400 MHz): δ 7.21 (m, 1H), 6.94 (m, 1H), 6.64 (s, 1H), 4.29 (d, J=7.6 Hz, 1H), 3.80 (m, 3H), 3.38 (s, 3H), 3.01-3.11 (m, 2H), 2.62-2.76 (m, 2H), 2.00-2.19 (m, 4H), 1.65-1.74 (m, 4H), 1.33-1.49 (m, 5H).

Example 13

Synthesis of Compound 13

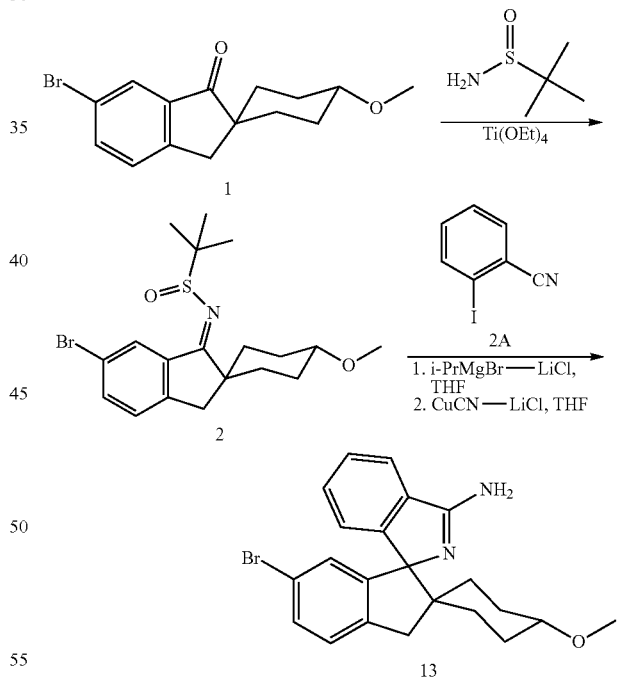

Procedure for Preparation of Compound 2

To a solution of compound 1 (5.0 g, 19 mol) in anhydrous THF (50 mL) was added tert-butylsulfanilamide (4.6 g, 38 mol) and Ti(OEt)$_4$ (22 g, 76.9 mol). The solution was heated at reflux for 48 h under a N$_2$ atmosphere. Water (10 mL) was added to quench the reaction and the mixture was extracted with EtOAc (2×50 mL). The combined organic layers were dried over Na$_2$SO$_4$ and evaporated under vacuum to give the crude. The crude was purified by chromatographic on silica gel (hexane:EtOAc=20:1) to afford compound 2 (3.0 g, 43%) as a yellow solid.

Procedure for Preparation of Compound 3

To a mixture of compound 2 (200 mg, 0.55 mmol) in anhydrous THF (3 mL) was added dropwise n-BuLi (0.44 mL, 1.10 mmol) at −78° C. under a N$_2$ atmosphere. After stirring for 10 min, a solution of 3-Bromo-5-trifluoromethyl-pyridine (246 mg, 1.10 mmol) in anhydrous THF (2 mL) was added. The solution was stirred at −78° C. for 30 min, and then warmed to room temperature. Sat. NH$_4$Cl (2 mL) solution was added to quench the reaction and then extracted with EtOAc (3×5 mL). The combined organic layers were dried over Na$_2$SO$_4$ and evaporated under vacuum to afford the crude product. The crude was purified by preparative TLC (EtOAc) to give compound 3 (70 mg, 25%) as a white solid.

Procedure for Preparation of Compound 4

A solution of compound 3 (50 mg, 0.137 mmol) in sat. HCl:MeOH (5 mL) was stirred at room temperature overnight. The reaction solution was evaporated under vacuum at room temperature. The residue was dissolved in MeOH and NH$_3$.H$_2$O was added to adjust pH=8-9, then was evaporated. The residue was washed with CH$_2$Cl$_2$ (5 mL) and the solid was filtered off. The filtrate was evaporated to give compound 4 (20 mg, 36%) as a white solid.

Procedure for Preparation of Compound 2

To a solution of compound 1 (200 mg, 0.67 mmol) in THF (4 mL) was added Ti(OEt)$_4$ (2 mL, 6.7 mmol). After being stirred at room temperature for 1 h, tert-butylsulfinamide (300 mg, 2.68 mmol) was added. The reaction mixture was stirred at reflux overnight. Then the mixture was partitioned between H$_2$O (10 mL) and EtOAc (20 mL). The mixture was filtered and the filtrate was extracted with EtOAc (3×100 mL). The combined organic layers were washed with brine (20 mL), dried over Na$_2$SO$_4$ and concentrated to dryness. The residue was purified by chromatography (petroleum ether:ethyl acetate=10:1) to give compound 3 (250 mg, 87%) as a yellow solid.

Procedure for Preparation of Compound 13

To a solution of i-PrMgCl—LiCl (4.83 mL, 6.28 mmol) was added compound 2A (1.44 g, 6.28 mmol) in THF (2 mL) at −20° C. in one portion, and the mixture was stirred at −20° C. for 20 min. Then to the above mixture was added the solution of compound 2 (250 mg, 0.628 mmol) in THF (1 mL) slowly at −20° C., followed by CuCN—LiCl solution (0.002 mL, 1 M in THF) and the mixture was stirred for 3 h at same temperature. The reaction was quenched by addition of saturated aqueous $NH_4Cl$ (3 mL). The aqueous layer was extracted with EtOAc (3×20 mL), the combined organic layers were washed with brine (10 mL), dried over $Na_2SO_4$ and concentrated to give the residue, which was purified by preparative TLC ($CH_2Cl_2$:MeOH=10:1) and HPLC (basic) to give compound 13 (2.0 mg, 11%).

LC-MS $t_R$=1.087 min in 2 min chromatography, MS (ESI) m/z 411/413 [M+H]$^+$.

$^1$H NMR (CD$_3$OD 400 MHz): δ 8.16 (d, J=8.0 Hz, 1H), 7.65-7.76 (m, 2H), 7.04-7.53 (m, 3H), 7.03 (s, 1H), 3.21 (s, 3H), 3.08 (m, 1H), 1.92-2.05 (m, 2H), 1.69-1.74 (m, 1H), 1.40-1.52 (m, 3H), 1.27-1.32 (m, 2H), 0.90-1.05 (m, 2H)

Example 14

Synthesis of Compound 14

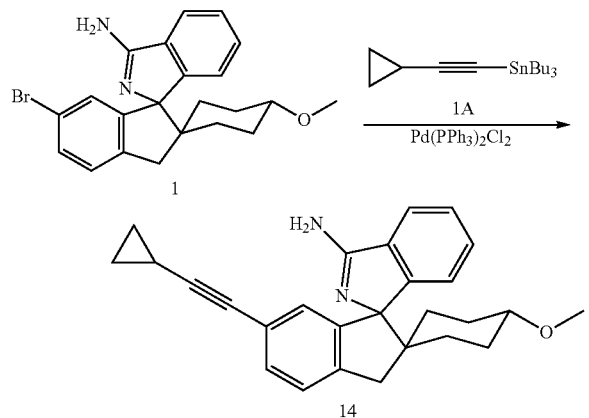

A solution containing compound 1A (0.2 mL, excess) and compound 1 (20 mg, 0.046 mol) in toluene (2 mL) was deoxygenated by bubbling a stream of nitrogen through the reaction mixture for 5 min. Then, PdCl$_2$(PPh$_3$)$_2$ (5 mg) was added. The reaction vial was sealed and placed into CEM microwave reactor and irradiated at 150° C. for 35 min. After being cooled to room temperature, the mixture was partitioned between EtOAc (20 mL) and aqueous CsF (4 M, 20 mL), and the aqueous layer was extracted with EtOAc (3×20 mL). The combined organic layers were washed with brine (15 mL), dried over anhydrous Na$_2$SO$_4$, filtered, and concentrated in vacuo. The residue was purified by preparative TLC (CH$_2$Cl$_2$:MeOH=10:1) and HPLC (basic) to yield compound 14 (3.3 mg, 18%) as a white solid.

LC-MS $t_R$=1.076 min in 2 min chromatography, MS (ESI) m/z 397 [M+H]$^+$.

$^1$H NMR (CD$_3$OD 400 MHz): δ 8.04 (d, J=7.6 Hz, 1H), 7.64 (t, J=7.6 Hz, 1H), 7.57 (t, J=7.6 Hz, 1H), 7.21-7.30 (m, 3H), 6.67 (s, 1H), 3.33 (s, 3H), 2.97 (m, 1H), 1.82-1.93 (m, 2H), 1.60-1.63 (m, 1H), 1.19-1.37 (m, 5H), 0.92-0.93 (m, 1H), 0.70-0.74 (m, 2H), 0.54-0.56 (m, 2H)

Example 15

Synthesis of Compound 15

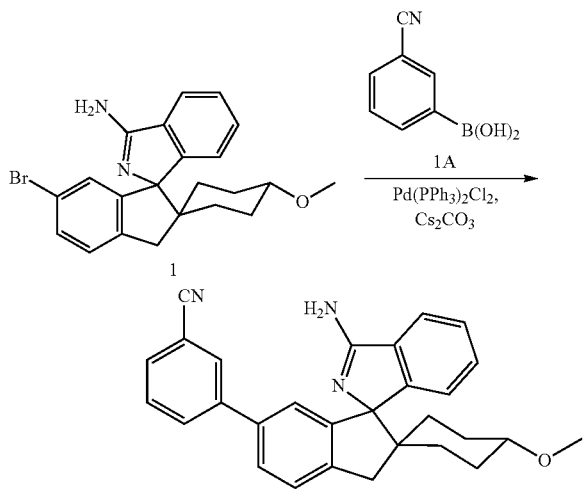

Pd(PPh$_3$)$_2$Cl$_2$ (5 mg) in a 10 mL of flask was treated with compound 1 (40 mg, 0.078 mmol), 1,4-dioxane (3 mL), compound 1A (17 mg, 0.118 mmol) and Cs$_2$CO$_3$ (2 N, 0.52 mL) sequentially under N$_2$. The mixture was heated under 120° C. under N$_2$ in a CEM microwave reactor for 15 min. The reaction mixture was concentrated in vacuo to give the residue, which was purified by preparative TLC on silica gel (CH$_2$Cl$_2$: MeOH=10:1) and by HPLC (0.1% TFA as buffer) to give compound 15 (1.0 mg, 5%) as a white solid.

LC-MS (698-146-1A): $t_R$=1.005 min in 2 min chromatography, MS (ESI) m/z 434 [M+H]$^+$.

$^1$H NMR (CD$_3$OD 400 MHz): δ 8.17 (d, J=7.6 Hz, 1H), 7.89 (m, 1H), 7.82 (m, 1H), 7.68 (m, 5H), 7.40 (d, J=7.6 Hz, 1H), 7.18 (s, 1H), 3.41 (m, 2H), 3.39 (s, 3H), 3.15 (m, 1H), 2.07 (m, 1H), 1.96 (m, 1H), 1.78 (m, 1H), 1.51 (m, 3H), 1.34 (m, 2H), 1.05 (m, 1H).

Example 16

Synthesis of Compound 16

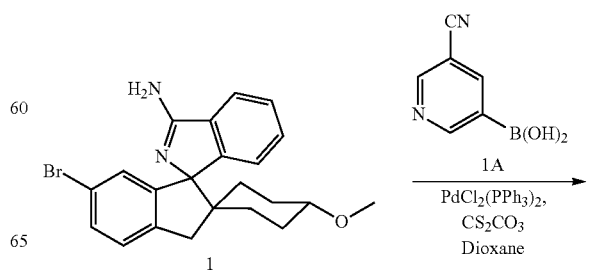

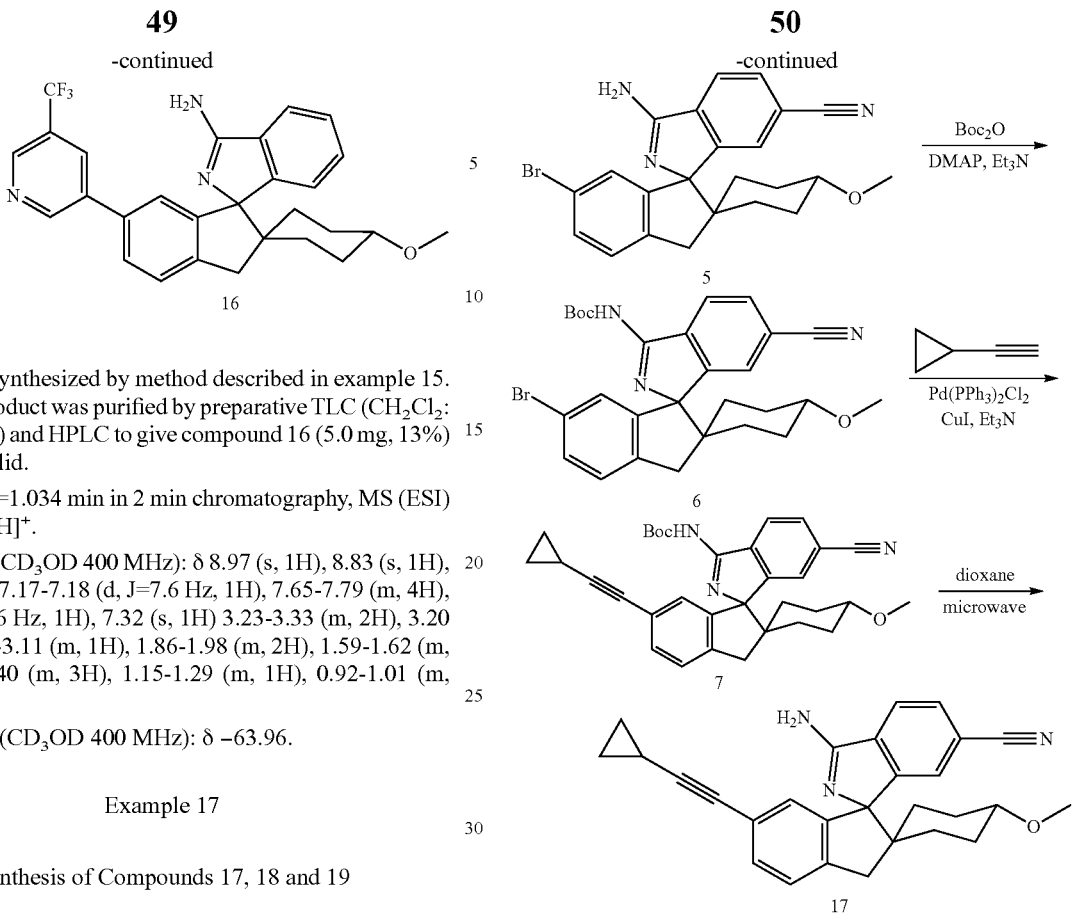

This was synthesized by method described in example 15. The crude product was purified by preparative TLC (CH$_2$Cl$_2$: MeOH=10:1) and HPLC to give compound 16 (5.0 mg, 13%) as a white solid.

LC-MS $t_R$=1.034 min in 2 min chromatography, MS (ESI) ink 478 [M+H]$^+$.

$^1$H-NMR (CD$_3$OD 400 MHz): δ 8.97 (s, 1H), 8.83 (s, 1H), 8.28 (s, 1H), 7.17-7.18 (d, J=7.6 Hz, 1H), 7.65-7.79 (m, 4H), 7.40 (d, J=7.6 Hz, 1H), 7.32 (s, 1H) 3.23-3.33 (m, 2H), 3.20 (s, 3H), 3.00-3.11 (m, 1H), 1.86-1.98 (m, 2H), 1.59-1.62 (m, 1H), 1.30-1.40 (m, 3H), 1.15-1.29 (m, 1H), 0.92-1.01 (m, 1H).

$^{19}$F-NMR (CD$_3$OD 400 MHz): δ −63.96.

Example 17

Synthesis of Compounds 17, 18 and 19

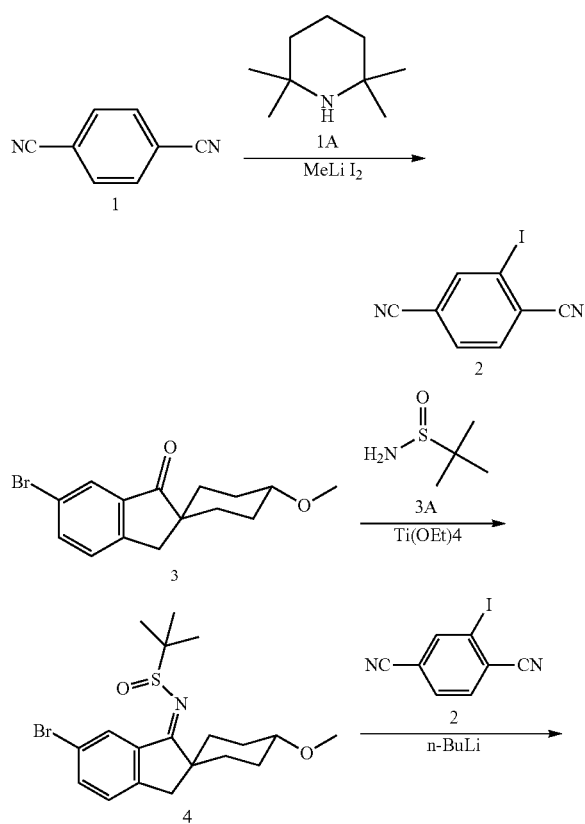

Procedure for Preparation of Compound 2

To a solution of compound 1A (5.31 g, 37.5 mmol) in THF (120 mL) was added MeLi (12.5 mL, 37.5 mmol) at 0° C. under a nitrogen atmosphere and the resulting mixture was stirred at 0° C. for 1 h. After being cooled to −78° C., a solution of compound 1(4 g, 31.2 mmol) in THF (200 mL) was added dropwise slowly. The dark solution was stirred at −78° C. for 40 min, and a solution of I$_2$(9.56 g, 37.5 mmol) in THF (50 mL) was added to above solution. After being stirred at −78° C. for 2 h, the mixture was allowed to warm to room temperature and stirred overnight. Then the mixture was quenched by addition of saturated aqueous NH$_4$Cl (10 mL). The aqueous layer was extracted with EtOAc (3×200 mL), and the combined organic layers were dried over Na$_2$SO$_4$ and concentrated in vacuo to give the crude product, which was purified by column chromatography on silica gel (petroleum ether:ethyl acetate=10:1) and HPLC to give compound 2 (1.5 g, 19%) as a yellow solid.

$^1$H NMR (CD$_3$OD 400 MHz): δ 8.43 (s, 1H), 7.87-7.94 (m, 2H).

Procedure for Preparation of Compound 5

To a solution of compound 2 (500 mg, 0.198 mmol) in THF (2 mL) was added n-BuLi (0.08 mL, 0.198 mmol) at −78° C., and the mixture was stirred at −78° C. for 30 min. Then to the above mixture was added the solution of compound 4 (81 mg, 0.198 mmol) in THF (1 mL) at −78° C. slowly, and the mixture was stirred at −78° C. for additional 2 h. The reaction mixture was allowed to warm to the room temperature and stirred overnight. Then the mixture was quenched by addition of saturated aqueous NH$_4$Cl (3 mL). The aqueous layer was extracted with EtOAc (3×20 mL), and the combined organic layers were dried over Na$_2$SO$_4$ and concentrated in vacuo to give the residue, which was purified by preparative TLC (CH$_2$Cl$_2$:MeOH=15:1) and HPLC to give compound 5 (14 mg, 16%) as a yellow solid.

Procedure for Preparation of Compound 6

To a solution of compound 5 (14 mg, 0.032 mmol) in THF (1 mL) was added DMAP (6 mg, 0.048 mmol), (Boc)$_2$O (11 mg, 0.048 mmol) and Et$_3$N (6.4 mg, 0.064 mmol) at room temperature and the resulting mixture was stirred overnight. The solvent was removed in vacuo to yield the crude compound, which was purified by preparative TLC (petroleum ether:ethyl acetate=3:1) to give compound 6 (9 mg, 52%) as a white solid.

Procedure for Preparation of Compound 7

An oven dried three-necked round bottom flask equipped with condenser was charged with compound 6 (24 mg, 0.046 mmol), Et$_3$N (2.5 mL) and Et$_2$NH (0.5 mL) under a nitrogen atmosphere. To this solution was added CuI (0.44 mg, 0.0023 mmol) and PdCl$_2$(PPh$_3$)$_2$ (2 mg, 0.0023 mmol). The system was degassed once again, then cyclopropyl acetylene (0.5 mL, excess) was added and the mixture was stirred at 60° C. (oil bath) overnight. The solvent was evaporated in vacuo and the residue was partitioned between ethyl acetate (20 mL) and water (10 mL). The aqueous layer was extracted with ethyl acetate (2×30 mL), the combined organic layers were washed with brine (30 mL), dried over Na$_2$SO$_4$, and concentrated under reduced pressure to dryness. The crude product was purified by preparative TLC (petroleum ether:ethyl acetate=3:1) to give compound 7 (7 mg, 30%) as a white solid.

Procedure for Preparation of Compound 17

A solution of compound 7 (7 mg, 0.0134 mmol) in dioxane (2 mL) was placed into CEM microwave reactor and irradiated at 120° C. for 15 min. The solvent was removed by evaporation in vacuo to yield the crude compound, which was purified by HPLC (basic) to give compound 17 (4.4 mg, 52%) as a white solid.

LC-MS t$_R$=1.158 min in 2 min chromatography, MS (ESI) m/z 422 [M+H]$^+$.

$^1$H NMR (CD$_3$OD 400 MHz): δ 7.87 (d, J=8.0 Hz, 1H), 7.73 (dd, J=0.8, 7.6 Hz, 1H), 7.42 (s, 1H), 7.25 (d, J=8.0 Hz, 1H), 7.13 (dd, J=1.6, 8.0 Hz, 1H), 6.50 (s, 1H), 3.33 (s, 3H), 3.23-3.33 (m, 2H), 2.88-3.00 (m, 1H), 1.79-1.95 (m, 2H), 1.51-1.62 (m, 1H), 1.32-1.48 (m, 1H), 1.10-1.38 (m, 4H), 0.75-0.88 (m, 1H), 0.65-0.75 (m, 2H), 0.50-0.55 (m, 2H).

Chiral Separation of Compound 17: Preparation of Compounds 18 and 19

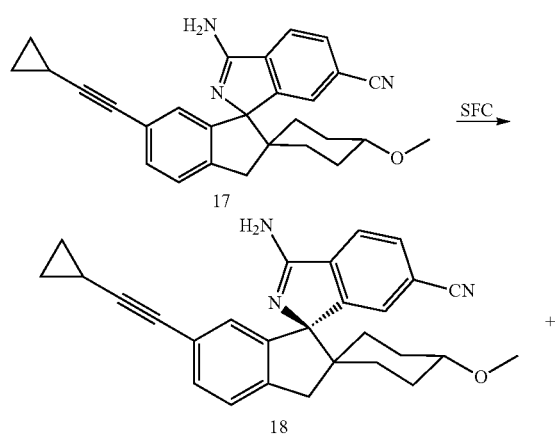

Compound 17 (50 mg, 0.12 mmol) was re-purified by preparative SFC to give compound 19 (18.30 mg, 37%) and compound 18 (6.70 mg, 13%). Spectra for compound 19:

LC-MS t$_R$=0.930 min in 2 min chromatography, m/z 422 [M+H]$^+$.

$^1$H NMR (CD$_3$OD 400 MHz): δ 8.32 (d, J=8.4 Hz, 1H), 8.03 (d, J=7.2 Hz, 1H), 7.77 (s, 1H), 7.40 (dd, J=1.2, 6.8 Hz, 2H), 6.88 (s, 1H), 3.33 (s, 3H), 3.25-3.28 (s, 2H), 3.10 (m, 1H), 1.95-2.07 (m, 2H), 1.74-1.76 (m, 1H), 1.33-1.49 (m, 5H), 1.05-1.06 (m, 1H), 0.81-0.86 (m, 2H), 0.66-0.67 (m, 2H).

SFC: t$_R$=7.67 min in 15 min chromatography, ee=98%.

Spectra for Compound 18:

LC-MS t$_R$=0.930 min in 2 min chromatography, m/z 422 [M+H]$^+$.

$^1$H NMR (CD$_3$OD 400 MHz): δ 8.32 (d, J=8.4 Hz, 1H), 8.03 (d, J=7.2 Hz, 1H), 7.77 (s, 1H), 7.40 (dd, J=1.2 Hz, 6.8, 2H), 6.88 (s, 1H), 3.33 (s, 3H), 3.25-3.28 (s, 2H), 3.10 (m, 1H), 1.95-2.07 (m, 2H), 1.74-1.76 (m, 1H), 1.33-1.49 (m, 5H), 1.05-1.06 (m, 1H), 0.81-0.86 (m, 2H), 0.66-0.67 (m, 2H).

SFC: t$_R$=8.29 min in 15 min chromatography, ee=90%.

Example 18

Synthesis of Compound 20

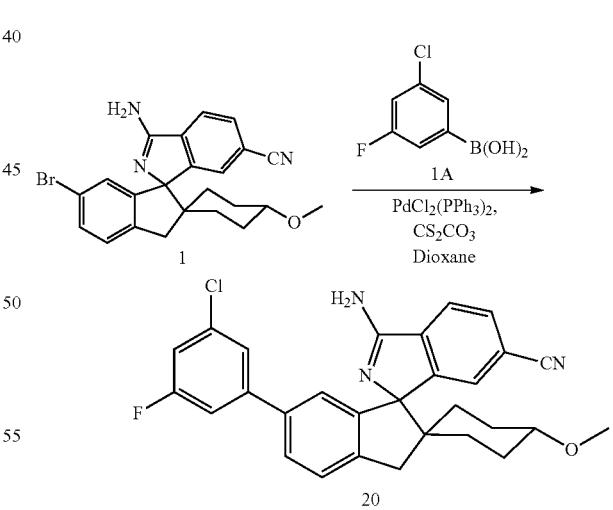

This was synthesized by method described in example 15. The solution was concentrated in vacuo and the residue was purified by preparative TLC (CH$_2$Cl$_2$:MeOH=10:1) and HPLC to give compound 20 (1.6 mg, 4%) as a white solid.

LC-MS t$_R$=0.994 min in 2 min chromatography, MS (ESI) m/z 486 [M+H]$^+$.

$^1$H-NMR (CD$_3$OD 400 MHz): δ 8.34 (d, J=8.4 Hz, 1H), 8.05 (d, J=8.0 Hz, 1H), 7.81 (s, 1H), 7.72 (d, J=9.6 Hz, 1H), 7.63 (d, J=8.0 Hz, 1H), 7.42 (s, 1H), 7.26-7.29 (m, 1H), 7.17 (d, J=8.4 Hz, 1H), 3.23-3.33 (m, 2H), 3.20 (s, 3H), 3.00-3.11 (m, 1H), 1.86-1.98 (m, 2H), 1.59-1.62 (m, 1H), 1.30-1.40 (m, 3H), 1.15-1.29 (m, 1H), 0.92-1.01 (m, 1H).

Example 19

Synthesis of Compound 21

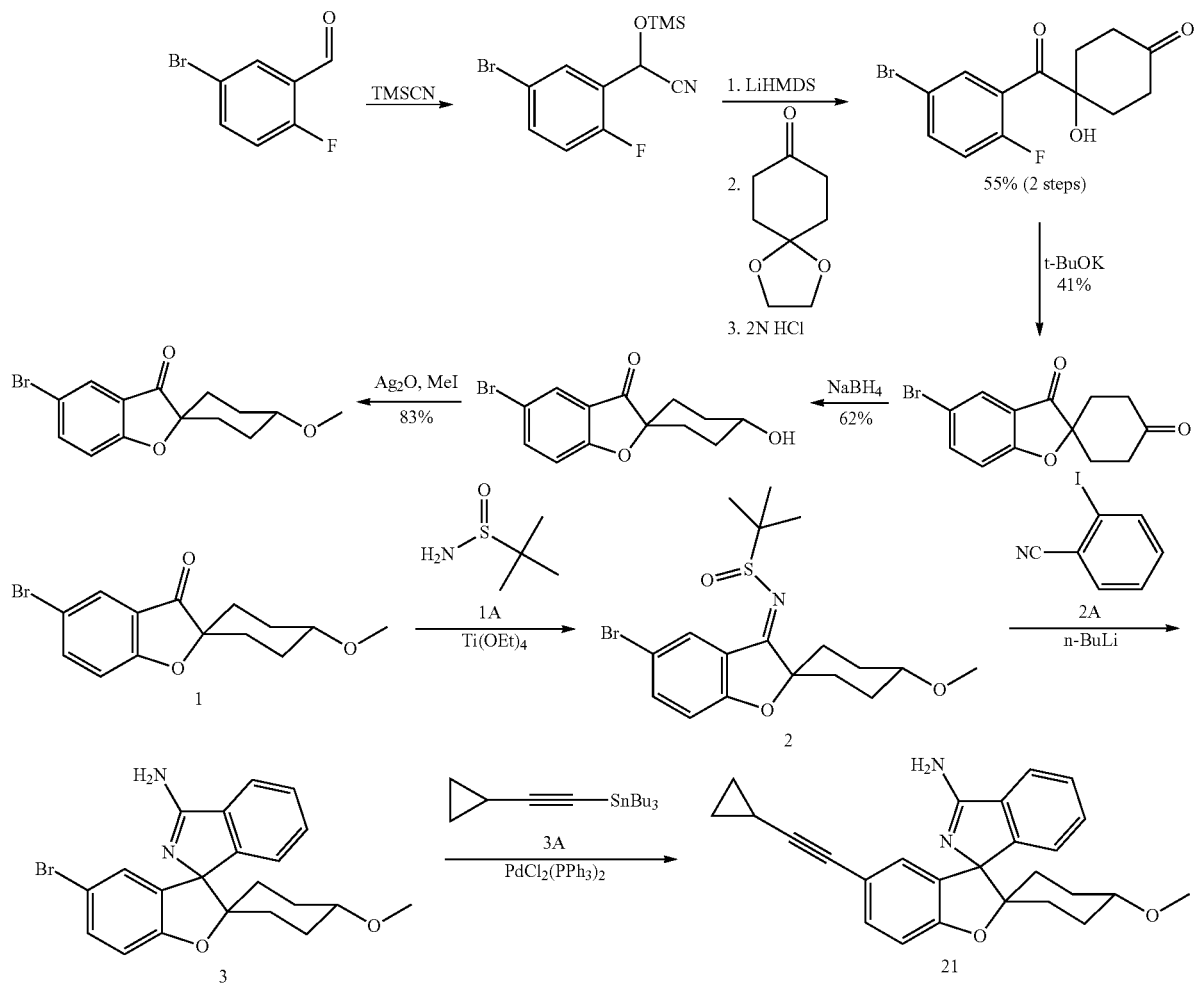

Step 1. Synthesis of 2-(5-bromo-2-fluorophenyl)-2-(trimethylsilyloxy)acetonitrile To a solution of 5-bromo-2-fluorobenzaldehyde (3.4160 g, 16.8 mmol) and DMAP (0.0256 g, 0.21 mmol, 0.012 equiv) in CH$_3$CN (35 mL) was added TMSCN (1.8885 g, 19.0 mmol, 1.13 equiv) dropwise via a syringe under nitrogen at room temperature. After 3.75 h, the solvent was removed under reduced pressure. The crude product was directly used in the next step without further purification.

Step 2. Synthesis of 4-(5-bromo-2-fluorobenzoyl)-4-hydroxycyclohexanone

To a solution of 2-(5-bromo-2-fluorophenyl)-2-(trimethylsilyloxy)acetonitrile (16.8 mmol), obtained as described above, in THF (10 mL) was added LiHMDS (1.0 M in THF, 18 mL, 18 mmol, 1.07 equiv) via a syringe under nitrogen at −78° C. After 1.25 h, a solution of 1,4-cyclohexanedione mono-ethylene ketal (2.6310 g, 16.8 mmol, 1.0 equiv) in THF (20 mL) was added dropwise via a cannula. The resulting mixture was allowed to slowly warm to 10° C. over 16 h. The mixture was then quenched with saturated NH$_4$Cl (10 mL) and H$_2$O (10 mL), extracted twice with ethyl acetate, and dried over Na$_2$SO$_4$. After the solvent was evaporated under reduced pressure, the residue was treated with MeOH (120 mL) and 2 N HCl (40 mL). The resulting solution was vigorously stirred at room temperature for 24 h and the solvents were removed under reduced pressure. The residue was extracted twice with CH$_2$Cl$_2$, dried over Na$_2$SO$_4$. After the solvent was evaporated under reduced pressure, the residue was purified by chromatography on silica gel eluted with hexanes/ethyl acetate to afford 2.9319 g (55% in two steps) of 4-(5-bromo-2-fluorobenzoyl)-4-hydroxycyclohexanone.

LC-MS t$_R$=1.39 min in 3 min chromatography, m/z 315, 317 (MH$^+$); $^1$H NMR (400 MHz, CDCl$_3$) δ 7.62-7.57 (m, 1H), 7.50-7.47 (m, 1H), 7.08-7.03 (m, 1H), 3.41 (s, 1H), 2.83-2.74 (m, 2H), 2.42-2.36 (m, 2H), 2.31-2.23 (m, 2H), 2.14-2.09 (m, 2H); $^{13}$C NMR (100 MHz, CDCl$_3$) δ 209.51, 204.88 (d, J=2.30 Hz), 157.68 (d, J=248.44 Hz), 135.66 (d, J=8.44 Hz), 131.55 (d, J=3.83 Hz), 127.54 (d, J=19.17 Hz), 118.07 (d, J=24.53 Hz), 117.19 (d, J=3.84 Hz), 78.07, 36.37, 33.89, 33.87; $^{19}$F NMR (376 MHz, CDCl$_3$) δ −112.90.

Step 3. 5-bromo-3H-spiro[benzofuran-2,1'-cyclohexane]-3,4'-dione

To a solution of 4-(5-bromo-2-fluorobenzoyl)-4-hydroxycyclohexanone (1.0055 g, 3.19 mmol, 1.0 equiv) in THF (30 mL) was added 95% t-BuOK (0.3440 g, 2.91 mmol, 0.9 equiv) portionwise. The resulting mixture was heated at 100° C. for 1 h. The reaction mixture was then cooled with an ice bath and quenched with $H_2O$, extracted with ethyl acetate, dried over $Na_2SO_4$. After the solvents were evaporated, the residue was purified by chromatography on silica gel eluted with hexanes/ethyl acetate to afford 0.3889 g (41%) of 5-bromo-3H-spiro[benzofuran-2,1'-cyclohexane]-3,4'-dione as a white solid. LC-MS $t_R$=1.58 min in 3 min chromatography, m/z 295, 297 (MH$^+$); $^1$H NMR (400 MHz, CDCl$_3$) δ 7.82-7.81 (m, 1H), 7.76-7.73 (m, 1H), 7.10-7.07 (m, 1H), 2.81-2.72 (m, 2H), 2.60-2.55 (m, 2H), 2.29-2.21 (m, 2H), 2.08-2.03 (m, 2H); $^{13}$C NMR (100 MHz, CDCl$_3$) δ 208.25, 200.80, 169.71, 140.99, 127.47, 121.58, 115.55, 114.81, 88.10, 36.68, 31.86.

Step 4. Synthesis of cis-5-bromo-4'-hydroxy-3H-spiro[benzofuran-2,1'-cyclohexan]-3-one and trans-5-bromo-4'-hydroxy-3H-spiro[benzofuran-2,1'-cyclohexan]-3-one To a solution of 5-bromo-3H-spiro[benzofuran-2,1'-cyclohexane]-3,4'-dione (0.2281 g, 0.77 mmol) in THF (15 mL) was added NaBH$_4$ (0.0266 g, 0.70 mmol) portionwise at −78° C. After 15 min, additional NaBH$_4$ (0.0138 g, 0.36 mmol) was added at −78° C. After 25 min, the reaction mixture was quenched with acetone and stirred at room temperature for 1 h. After the solvents were evaporated, the residue was purified by chromatography on silica gel eluted with hexanes/ethyl acetate to afford 0.0108 g (5%) of trans-5-bromo-4'-hydroxy-3H-spiro[benzofuran-2,1'-cyclohexan]-3-one and 0.1424 g (62%) of cis-5-bromo-4'-hydroxy-3H-spiro[benzofuran-2,1'-cyclohexan]-3-one.

For trans-5-bromo-4'-hydroxy-3H-spiro[benzofuran-2,1'-cyclohexan]-3-one, LC-MS $t_R$=1.56 min in 3 min chromatography, m/z 297, 299 (MH$^+$), 279, 281; $^1$H NMR (400 MHz, CDCl$_3$) δ 7.78-7.77 (m, 1H), 7.70-7.66 (m, 1H), 7.02-6.99 (m, 1H), 4.18-4.17 (m, 1H), 2.23-2.14 (m, 2H), 2.03-1.87 (m, 4H), 1.53-1.49 (m, 2H).

For cis-5-bromo-4'-hydroxy-3H-spiro[benzofuran-2,1'-cyclohexan]-3-one, LC-MS $t_R$=1.47 min in 3 min chromatography, m/z 297, 299 (MH$^+$); $^1$H NMR (400 MHz, CDCl$_3$) δ 7.77-7.76 (m, 1H), 7.70-7.67 (m, 1H), 7.05-7.02 (m, 1H), 3.83-3.78 (m, 1H), 2.08-2.03 (m, 2H), 1.88-1.72 (m, 6H); $^{13}$C NMR (100 MHz, CDCl$_3$) δ 202.30, 169.84, 140.60, 127.21, 121.81, 115.54, 114.20, 89.12, 68.73, 30.67, 30.37.

Step 5. synthesis of cis-5-bromo-4'-methoxy-3H-spiro[benzofuran-2,1'-cyclohexan]-3-one A mixture of cis-5-bromo-4'-hydroxy-3H-spiro[benzofuran-2,1'-cyclohexan]-3-one (0.1424 g, 0.48 mmol), Ag$_2$O (0.3800 g, 1.64 mmol), MeI (0.85 mL, 13.6 mmol), and Drierite® (0.78 g) in CH$_3$CN (5 mL) was vigorously stirred at room temperature for 66 h. The reaction mixture was filtered. After the solvents were evaporated, the residue was purified by chromatography on silica gel eluted with hexanes/ethyl acetate to afford 0.1232 g (83%) of cis-5-bromo-4'-methoxy-3H-spiro[benzofuran-2,1'-cyclohexan]-3-one and recover 0.0220 g (15%) of cis-5-bromo-4'-hydroxy-3H-spiro[benzofuran-2,1'-cyclohexan]-3-one.

For cis-5-bromo-4'-methoxy-3H-spiro[benzofuran-2,1'-cyclohexan]-3-one, LC-MS $t_R$=1.86 min in 3 min chromatography, m/z 311, 313 (MH$^+$); $^1$H NMR (400 MHz, CDCl$_3$) δ 7.68-7.67 (m, 1H), 7.63-7.60 (m, 1H), 6.97 (d, J=8.8 Hz, 1H), 3.33 (s, 3H), 3.29-3.22 (m, 1H), 2.08-2.04 (m, 2H), 1.77-1.57 (m, 6H); $^{13}$C NMR (100 MHz, CDCl$_3$) δ 202.15, 169.74, 140.44, 127.07, 121.77, 115.48, 114.04, 89.32, 55.70, 30.09, 26.95.

Step 6: Synthesis of intermediate 2

A solution of compound 1 (500 mg, 1.613 mmol), Ti(OEt)$_4$ (4.58 g, 16.13 mmol) and compound 1A (780 mg, 6.45 mmol) in THF (10 mL) was heated at reflux overnight. Then the mixture was partitioned between H$_2$O (10 mL) and EtOAc (30 mL). The mixture was filtered and the filtrate was extracted with EtOAc (3×100 mL). The combined organic layers were washed with brine (20 mL), dried over Na$_2$SO$_4$ and concentrated in vacuo. The residue was purified by preparative TLC (petroleum:ethyl acetate, 5:1) to give compound 2 (300 mg, 45%) as a yellow solid.

Step 7: Synthesis of intermediate 3

To a solution of compound 2A (183 mg, 0.8 mmol) in THF (2 mL) was added n-BuLi (0.35 mL, 0.878 mmol) at −78° C. slowly. After being stirred at −78° C. for 30 min, a solution of compound 4 (300 mg, 0.726 mmol) in THF (1 mL) was added dropwise at −78° C. slowly. The mixture was stirred at −78° C. for 2 h, then was allowed to warm to the room temperature and stirred overnight. The mixture was quenched with saturated aqueous NH$_4$Cl (2 mL). The aqueous layer was extracted with EtOAc (3×20 mL), and the combined organic layers were washed with brine (15 mL), dried over Na$_2$SO$_4$ and concentrated under reduced pressure to give the residue, which was purified by preparative TLC (CH$_2$Cl$_2$:MeOH=10:1) and preparative HPLC to give compound 3 (60 mg, 20%) as a yellow solid.

Step 8: Synthesis of compound 21

A solution containing compound 3 (30 mg, 0.073 mol) and compound 3A (0.2 mL, excess) in toluene (2 mL) was deoxygenated by bubbling a stream of nitrogen through the reaction mixture for 5 min. Then, PdCl$_2$(PPh$_3$)$_2$ (5 mg) was added. The reaction vial was sealed and placed into CEM microwave reactor and irradiated at 130° C. for 35 min. After being cooled to room temperature, the mixture was partitioned between EtOAc (20 mL) and aqueous CsF (4 M, 10 mL), and the aqueous layer was extracted with EtOAc (3×20 mL). The combined organic layers were washed with brine (15 mL), dried over anhydrous Na$_2$SO$_4$, filtered, and concentrated in vacuo. The residue was purified by preparative TLC (CH$_2$Cl$_2$:MeOH, 10:1) and HPLC to give compound 21 (2.0 mg, 8%) as a white solid.

LC-MS $t_R$=0.950 min in 2 min chromatography, MS (ESI) ink 399 [M+H]$^+$.

$^1$H-NMR (CD$_3$OD 400 MHz): δ 8.19 (d, J=8.0 Hz, 1H), 7.75-7.83 (m, 2H), 7.51 (d, J=8.0 Hz, 1H), 7.38 (d, J=8.0 Hz, 1H), 7.00 (d, J=8.4 Hz, 1H), 6.87 (s, 1H), 3.33 (s, 3H), 3.00-3.11 (m, 1H), 1.95-2.07 (m, 4H), 1.53-1.66 (m, 3H), 1.26-1.37 (m, 2H), 0.81-0.83 (m, 2H), 0.63-0.65 (m, 2H).

Example 20

Synthesis of Compound 22

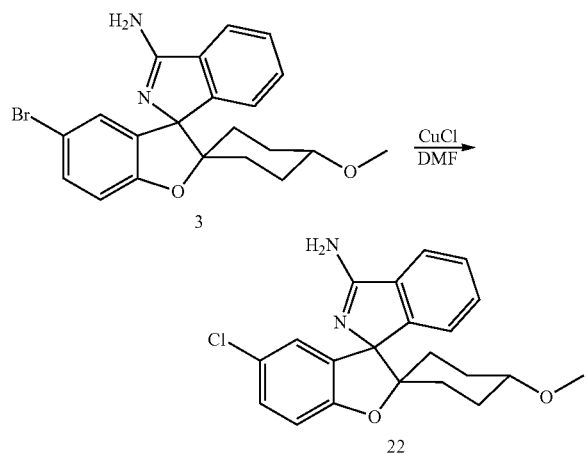

A mixture of compound 3 (20 mg, 0.049 mmol), CuCl (9.7 mg, 0.097 mmol)) in DMF (1.5 mL) was placed into CEM microwave reactor and irradiated at 170° C. for 40 min. After being cooled to room temperature, the mixture was partitioned between H$_2$O (10 mL) and EtOAc (20 mL). The aqueous layer was extracted with EtOAc (3×20 mL). The combined organic layers were washed with brine (10 mL), dried over Na$_2$SO$_4$ and concentrated to dryness. The residue was purified by preparative HPLC (acidic) to give compound 22 (5.3 mg, 30%) as a white solid.

LC-MS t$_R$=0.864 min in 2 min chromatography, MS (ESI) ink 369 [M+H]$^+$.

$^1$H-NMR (CD$_3$OD 400 MHz): δ 8.18 (d, J=7.6 Hz, 1H), 7.85 (t, J=7.6 Hz, 1H), 7.77 (t, J=7.2 Hz, 1H), 7.52 (d, J=8.0 Hz, 1H), 7.39 (dd, J=2.0, 8.4 Hz, 1H), 7.08 (d, J=8.4 Hz, 1H), 6.91 (s, 1H), 3.33 (s, 3H), 3.18 (m, 1H), 2.18-2.23 (m, 1H), 1.96-2.10 (m, 3H), 1.55-1.70 (m, 3H), 1.25-1.26 (m, 1H).

Example 21

Synthesis of Compound 23

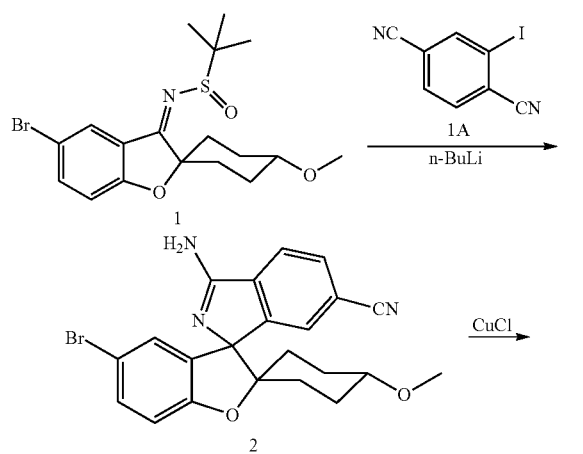

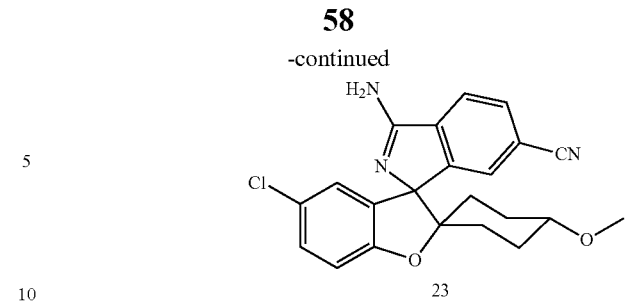

Procedure for Preparation of Compound 2

To a solution of compound 1A (135 mg, 0.533 mmol) in THF (3 mL) was added n-BuLi (0.234 mL, 0.586 mmol) at −78° C. slowly. The reaction mixture was stirred at −78° C. for 30 min, a solution of compound 1 (200 mg, 0.484 mmol) in THF (2 mL) was added dropwise to above mixture slowly. After being stirred at −78° C. for 2 h, the mixture was allowed to warm to the room temperature and stir overnight. Then the mixture was quenched with saturated aqueous NH$_4$Cl (2 mL). The aqueous layer was extracted with EtOAc (3×20 mL), and the combined organic layers were washed with brine (20 mL), dried over Na$_2$SO$_4$ and concentrated in vacuo to give the residue, which was purified by preparative TLC (CH$_2$Cl$_2$: MeOH=10:1) to give compound 2 (42 mg, 20%) as a yellow solid.

General Procedure for Preparation of Compound 23

A mixture of compound 2 (42 mg, 0.096 mmol) and CuCl (19 mg, 0.192 mmol)) in DMF (2 mL) was placed into CEM microwave reactor and irradiated at 170° C. for 40 min. After being cooled to room temperature, the mixture was partitioned between H$_2$O (10 mL) and EtOAc (20 mL). The aqueous layer was extracted with EtOAc (3×20 mL). The combined organic layers were washed with brine (10 mL), dried over Na$_2$SO$_4$ and concentrated in vacuo to dryness. The residue was purified by preparative HPLC (acidic) to give compound 23 (3.2 mg, 9%) as a white solid.

LC-MS t$_R$=0.920 min in 2 min chromatography, MS (ESI) m/z 390 [M+H]$^+$.

$^1$H-NMR (CD$_3$OD 400 MHz): δ 8.26 (d, J=8.0 Hz, 1H), 8.04 (d, J=8.0 Hz, 1H), 7.89 (s, 1H), 7.33 (m, 1H), 7.01 (d, J=8.8 Hz, 1H), 6.94 (s, 1H), 3.21 (s, 3H), 3.08 (m, 1H), 2.00-2.12 (m, 1H), 1.89-1.99 (m, 3H), 1.47-1.61 (m, 3H), 1.15-1.22 (m, 2H).

Example 22

Synthesis of Compound 24

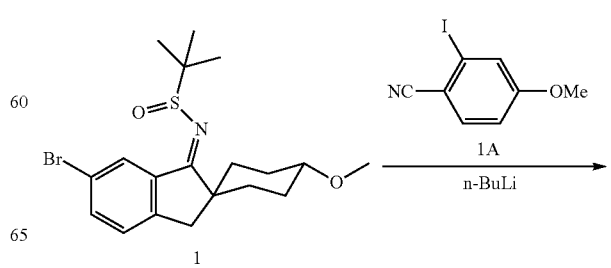

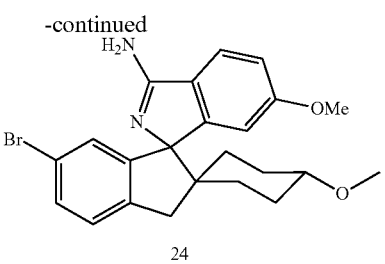

24

This compound was synthesized by method described in Example 19, step 7. The crude product was purified by preparative TLC (CH₂Cl₂:MeOH=10:1) and HPLC to give compound 24 (183 mg, yield 21%) as a yellow solid.

LC-MS $t_R$=1.020 min in 2 min chromatography, MS (ESI) m/z 441/443 [M+H]⁺.

¹H-NMR (CD₃OD 400 MHz): δ 8.08 (d, J=8.8 Hz, 1H), 7.54 (d, J=8.0 Hz, 1H), 7.42 (d, J=8.0 Hz, 1H), 7.23 (d, J=8.8 Hz, 1H), 7.05 (s, 1H), 6.75 (s, 1H), 3.33 (s, 3H), 3.23-3.33 (m, 2H), 3.00-3.11 (m, 1H), 1.96-2.05 (m, 2H), 1.70-1.71 (m, 1H), 1.45-1.53 (m, 3H), 1.31 (m, 1H); 1.05-1.06 (m, 1H).

Example 23

Synthesis of Compound 25

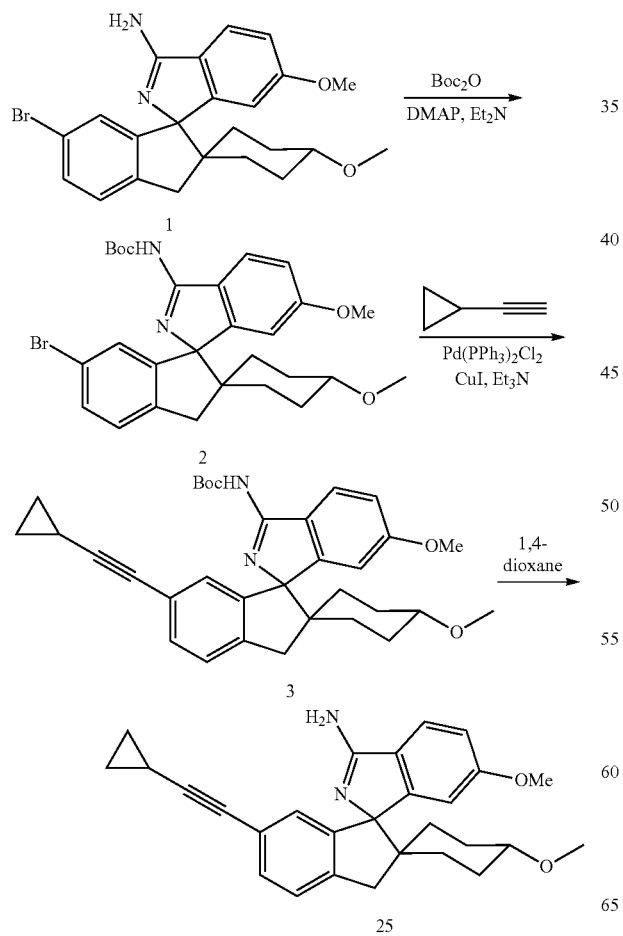

General Procedure for Preparation of Compound 2

To a solution of compound 1 (150 mg, 0.34 mmol) in THF (7.5 mL) was added DMAP (63 mg, 0.51 mmol), (Boc)₂O (112 mg, 0.51 mmol) and Et₃N (69 mg, 0.68 mmol) at room temperature and the resulting mixture was stirred overnight. The solvent was removed in vacuo to yield the crude compound, which was purified by preparative TLC (petroleum ether:ethyl acetate=3:1) to give compound 2 (60 mg, 33%) as a white solid.

General Procedure for Preparation of Compound 3

An oven dried three-necked round bottom flask equipped with condenser was charged with compound 2 (60 mg, 0.11 mmol), Et₃N (3.6 mL) and Et₂NH (0.7 mL) under N₂ atmosphere. To this solution was added CuI (1 mg, 0.0055 mmol) and PdCl₂(PPh₃)₂ (4 mg, 0.0055 mmol). The system was degassed once again, then cyclopropyl acetylene (0.6 mL, excess) was added and the mixture was stirred at 60° C. (oil bath) overnight. The solvent was evaporated in vacuo and the residue was partitioned between ethyl acetate (2×70 mL) and water (20 mL). The combined organic layers were washed with brine (30 mL), dried over Na₂SO₄, and concentrated under reduced pressure to dryness. The crude product was purified by preparative TLC (petroleum ether:ethyl acetate=3:1) to give compound 3 (23 mg, 39%) as a white solid.

General Procedure for Preparation of Compound 25

A solution of compound 3 (23 mg, 0.0218 mmol) in dioxane (5 mL) was placed into CEM microwave reactor and irradiated at 120° C. for 15 min. The solvent was removed by evaporation in vacuo to yield the crude compound, which was purified by HPLC (basic) to give compound 25 (2.4 mg, 16%) as a white solid.

LC-MS $t_R$=1.0564 min in 2 min chromatography, MS (ESI) m/z 427.1 [M+H]⁺.

¹H-NMR (CD₃OD 400 MHz): δ 8.050 (d, J=8.8 Hz, 1H), 7.394 (d, J=7.6 Hz, 1H), 7.334 (d, J=7.6 Hz, 1H), 7.218 (d, J=2.4 Hz, 1H), 6.802 (s, 1H), 6.733 (s, 1H), 3.863 (s, 3H), 3.334 (s, 3H), 3.289 (m, 3H), 2.031 (m, 2H), 1.721 (m, 1H), 1.315-1.530 (m, 5H), 1.073 (m, 1H), 0.857 (m, 2H), 0.689 (m, 2H).

Example 24

Synthesis of Compound 26

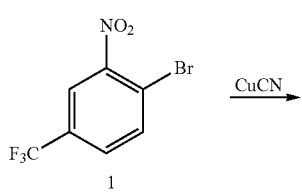

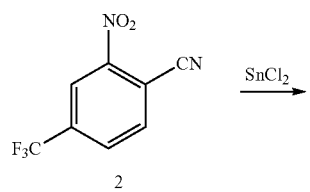

-continued

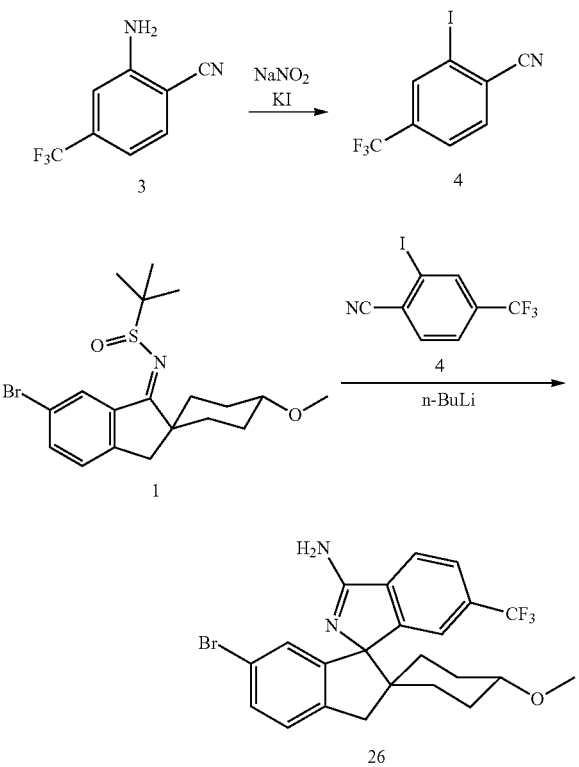

Step 1. Synthesis of Intermediate 2

A mixture of compound 1 (1.5 g, 2.79 mmol), CuCN (0.55 g, 6.11 mmol)) in NMP (4 mL) was heated at 130° C. for 4 h. Then the mixture was cooled to room temperature, and partitioned between H₂O (20 mL) and EtOAc (30 mL). The aqueous layer was extracted with EtOAc (3×30 mL). The combined organic layers were washed with brine (20 mL), dried over Na₂SO₄ and concentrated to dryness. The residue was purified by column chromatography on silica gel (petroleum ether:ethyl acetate=10:1) to give compound 2 (0.8 g, 67%) as a yellow solid.

Step 2. Synthesis of Intermediate Compound 3

To a solution of SnCl₂ (3.34 g, 14.8 mmol) in concentrated HCl (2.7 mL) was added a solution of compound 2 (0.8 g, 3.7 mmol) in 95% ethanol (1.3 mL). The resulting mixture was stirred at room temperature for 2 h. TLC showed the reaction was completed, and the mixture was treated with 50% aqueous NaOH solution (10 mL) to give the yellow solid. The resulting mixture was filtered, and the filter cake was dissolved in CH₂Cl₂ (200 mL). The mixture was filtered, and the filtrate was dried over Na₂SO₄ and concentrated in vacuo to give compound 3 (0.4 g, 58%) as a yellow solid.

Step 3. Synthesis of Intermediate 4

To a solution of compound 3 (0.4 g, 2.15 mmol) in concentrated HCl (1 mL) was added a solution of NaNO₂ (0.222 g, 3.22 mmol) in H₂O (8 mL) slowly while keeping temperature between −5° C.~0° C. After addition, the reaction mixture was stirred at 0° C. for 30 min. Then, a solution of KI (3.57 g, 21.5 mmol) in H₂O (7 mL) was added slowly and stirred for another 3 h. The resulting mixture was filtered, and the filtrate was extracted with ethyl acetate (2×100 mL). The combined organic layer was dried over Na₂SO₄ and concentrated in vacuo to give the residue, which was purified by column chromatography on silica gel (petroleum ether:ethyl acetate=10:1) to give compound 4 (0.6 g, 94%) as a yellow solid.

Step 4. Preparation of Compound 26

This was synthesized by method described in example 25. The crude product was purified by preparative TLC (CH₂Cl₂: MeOH=10:1) and HPLC to give compound 26 (2.5 mg, 4%) as a yellow solid.

LC-MS $t_R$=0.949 min in 2 min chromatography, MS (ESI) m/z 479/481 [M+H]⁺.

¹H-NMR (CD₃OD 400 MHz): δ 8.39 (d, J=8.4 Hz, 1H), 8.04 (d, J=7.6 Hz, 1H), 7.56-7.59 (m, 2H), 7.46 (d, J=8.0 Hz, 1H), 7.13 (s, 1H), 3.23-3.33 (m, 2H), 3.20 (s, 3H), 3.00-3.11 (m, 1H), 1.86-1.98 (m, 2H), 1.59-1.62 (m, 1H), 1.30-1.40 (m, 3H), 1.15-1.29 (m, 1H), 0.92-1.01 (m, 1H).

¹⁹F-NMR (706-182-1J CD₃OD 400 MHz): δ −64.176.

Example 25

Synthesis of Compound 27

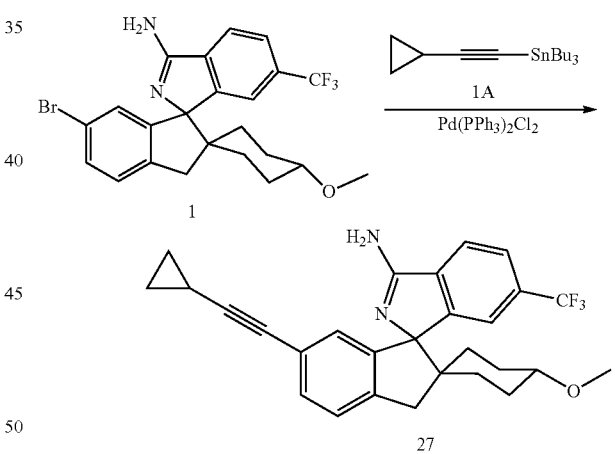

This was synthesized by method described in example 14. The crude product was purified by preparative TLC (CH₂Cl₂: MeOH=10:1) and RP-HPLC (acidic) to yield compound 27 (9.2 mg,) as a white solid.

LC-MS $t_R$=1.058 min in 2 min chromatography, MS (ESI) m/z 465 [M+H]⁺.

¹H-NMR (CD₃OD 400 MHz): δ 8.37 (d, J=8.0 Hz, 1H), 8.01 (d, J=8.4 Hz, 1H), 7.56 (s, 1H), 7.43 (d, J=7.6 Hz, 1H), 7.40 (d, J=9.2 Hz, 1H), 6.87 (s, 1H), 3.33 (s, 3H), 3.25-3.28 (s, 2H), 3.10 (m, 1H), 1.95-2.07 (m, 2H), 1.74-1.76 (m, 1H), 1.36-1.45 (m, 5H), 1.05-1.06 (m, 1H), 0.81-0.86 (m, 2H), 0.66-0.68 (m, 2H).

¹⁹F-NMR (CD₃OD 400 MHz): δ −64.198.

Example 26

Synthesis of Compound 28

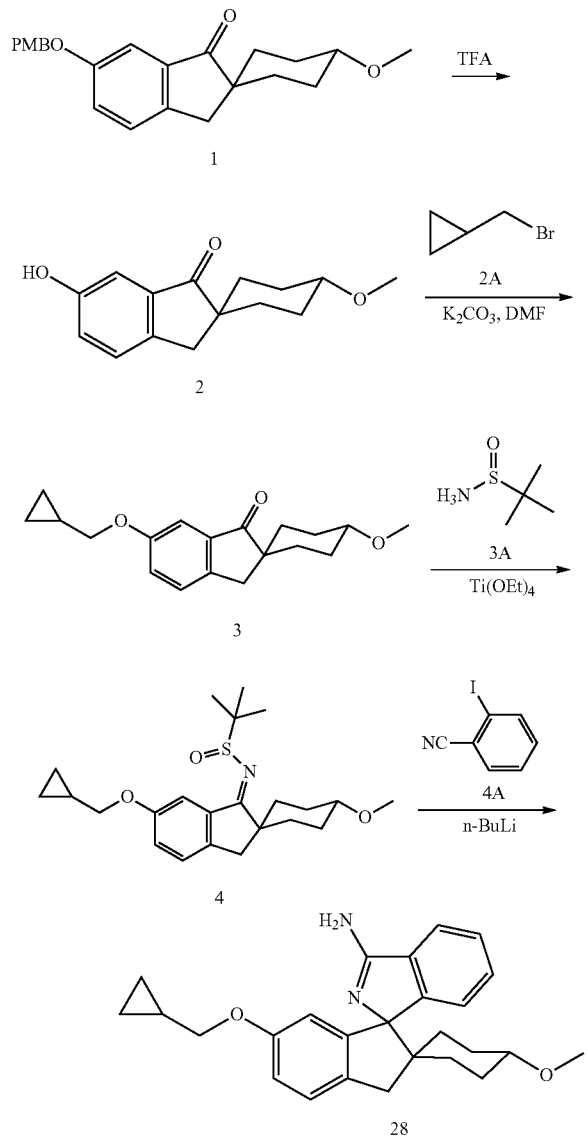

Step 1. Synthesis of Intermediate 2

To a solution of compound 1 (500 mg, 1.37 mmol) in $CH_2Cl_2$ (10 mL) was added TFA (0.8 mL) at room temperature and stirred overnight, and then ice-water (20 g) was added. The aqueous layer was extracted with $CH_2Cl_2$ (3×20 mL), and the combined organic layers were dried over $Na_2SO_4$ and concentrated in vacuo to give the residue, which was purified by preparative TLC (petroleum:ethyl acetate=5:1) to give compound 2 (300 mg, 88%) as a yellow oil.

Step 2. Synthesis of Intermediate 3

To a solution of compound 2 (200 mg, 0.82 mmol) and $K_2CO_3$ (227 mg, 1.64 mmol) in DMF (6 mL) was added compound 2A (165 mg, 1.224 mmol) at room temperature and stirred overnight. The solvent was added water (20 mL). The aqueous layer was extracted with EtOAc (3×20 mL), and the combined organic layers were dried over $Na_2SO_4$ and concentrated in vacuo to give the residue, which was purified by preparative TLC (petroleum:ethyl acetate=5:1) to give compound 3 (210 mg, 86%) as a yellow oil.

Step 4. Synthesis of Intermediate 4

A solution of compound 3 (210 mg, 0.7 mmol), $Ti(OEt)_4$ (1.99 g, 7 mmol) and compound 3A (339 mg, 2.8 mmol) in THF (5 mL) was heated at reflux overnight. Then the mixture was partitioned between $H_2O$ (10 mL) and EtOAc (20 mL). The mixture was filtered and the filtrate was extracted with EtOAc (3×100 mL). The combined organic layers were washed with brine (20 mL), dried over $Na_2SO_4$ and concentrated in vacuo to dryness. The residue was purified by preparative TLC (petroleum:ethyl acetate=5:1) to give compound 4 (220 mg, 78%) as a yellow solid.

Procedure for Preparation of Compound 28

To a solution of compound 4A (213 mg, 0.93 mmol) in THF (2 mL) was added n-BuLi (0.372 mL, 0.93 mmol) slowly at −78° C., and the mixture was reacted at −78° C. for 30 min. Then to the above mixture was added a solution of compound 4 (75 mg, 0.186 mmol) in THF (1 mL) slowly at −78° C., and the mixture was reacted at −78° C. for 2 h, then slowly warm to the room temperature and reacted overnight. Then the mixture was quenched with saturated aqueous $NH_4Cl$ (2 mL). The aqueous layer was extracted with EtOAc (3×20 mL), and the combined organic layers were dried over $Na_2SO_4$ and concentrated to give the residue, which was purified by preparative TLC ($CH_2Cl_2$:MeOH, 10:1) and HPLC to give compound 28 (1.7 mg, 2%) as a yellow solid.

LC-MS $t_R$=1.132 min in 2 min chromatography, MS (ESI) m/z 403 $[M+H]^+$.

$^1$H-NMR ($CD_3OD$ 400 MHz): δ 8.10 (d, J=7.6 Hz, 1H), 7.70 (t, J=7.2 Hz, 1H), 7.64 (t, J=7.2 Hz, 1H), 7.30-7.34 (m, 2H), 6.91 (d, J=2.4 Hz, 1H), 6.34 (s, 1H), 3.61-3.70 (m, 2H), 3.23-3.33 (m, 2H), 3.20 (s, 3H), 3.00-3.11 (m, 1H), 1.89-2.00 (m, 2H), 1.71-1.74 (m, 1H), 1.40-1.45 (m, 3H), 0.97-1.30 (m, 3H), 0.51-0.54 (m, 2H), 0.24-0.25 (m, 2H).

Example 27

Synthesis of Compound 29

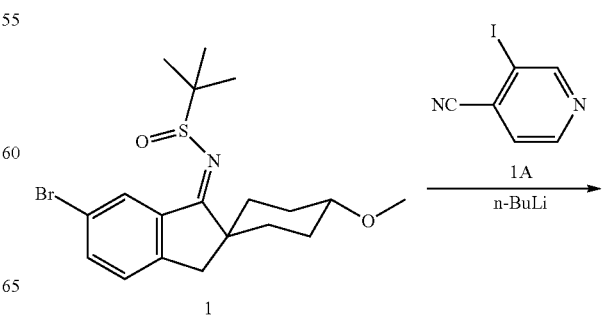

-continued

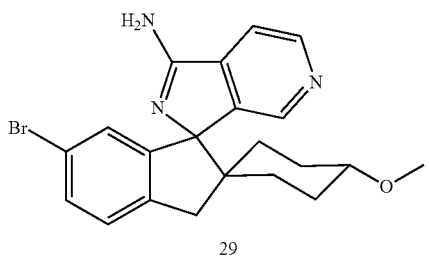

29

This was synthesized as described in example 20. The crude product was purified by preparative TLC (CH$_2$Cl$_2$:MeOH=10:1) and HPLC to give compound 29 (25 mg, yield 4%) as a yellow solid.

LC-MS t$_R$=0.959 min in 2 min chromatography, MS (ESI) m/z 412, 414 [M+H]$^+$.

$^1$H-NMR (CD$_3$OD 400 MHz): δ 8.81 (d, J=5.2 Hz, 1H), 8.59 (s, 1H), 8.05 (d, J=4.8 Hz, 1H), 7.50 (d, J=5.6 Hz, 1H), 7.36 (d, J=5.6 Hz, 1H), 7.06 (s, 1H), 3.23-3.33 (m, 2H), 3.20 (s, 3H), 3.00-3.11 (m, 1H), 1.86-1.98 (m, 2H), 1.59-1.62 (m, 1H), 1.30-1.40 (m, 3H), 1.15-1.29 (m, 1H), 0.92-1.01 (m, 1H).

Example 28

Synthesis of Compound 30

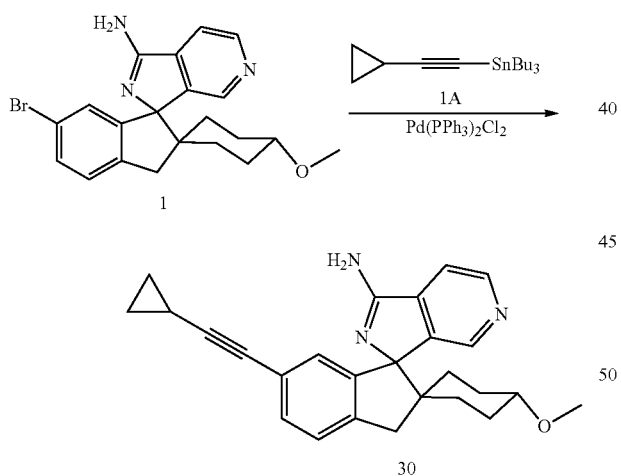

This was synthesized by method described for example 14. The crude product was purified by preparative TLC (CH$_2$Cl$_2$:MeOH=10:1) and HPLC to give compound 30 (3.0 mg, 58%) as a white solid.

LC-MS t$_R$=0.932 min in 2 min chromatography, MS (ESI) m/z 398 [M+H]$^+$.

$^1$H-NMR (CD$_3$OD 400 MHz): δ 8.92 (d, J=5.2 Hz, 1H), 8.69 (s, 1H), 8.15 (d, J=5.2 Hz, 1H), 7.45 (dd, J=8.0, 22.0 Hz, 2H), 6.88 (s, 1H), 3.23-3.33 (m, 2H), 3.20 (s, 3H), 3.00-3.11 (m, 1H), 1.86-1.98 (m, 2H), 1.59-1.62 (m, 1H), 1.30-1.40 (m, 3H), 1.15-1.29 (m, 1H), 0.92-1.01 (m, 1H).

Example 29

Synthesis of Compound 31

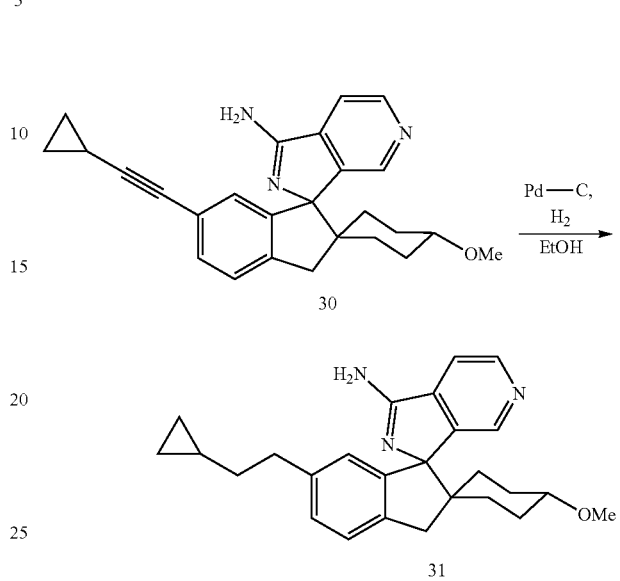

To a solution of compound 30 (11 mg, 0.028 mmol) in EtOH (5 mL) was added Pd/C (2 mg), the mixture was stirred at room temperature under H$_2$ atmosphere (1 atm) for 1 h. The reaction mixture was filtered through a pad of Celite, the filtrate was concentrated in vacuo to give the residue, which was purified by preparative HPLC to give compound 31 (2.5 mg, 22%) as a white solid.

LC-MS t$_R$=1.144 min in 2 min chromatography, MS (ESI) m/z 402 [M+H]$^+$.

$^1$H NMR (CD$_3$OD 400 MHz): δ 8.94 (d, J=5.2 Hz, 1H), 8.70 (s, 1H), 8.19 (d, J=4.8 Hz, 1H), 7.46 (d, J=7.6 Hz, 1H), 7.31 (d, J=7.6 Hz, 1H), 6.79 (s, 1H) 3.38 (s, 2H), 3.37 (s, 3H), 3.13 (m, 1H), 2.70 (m, 2H), 2.08 (m, 2H), 1.83 (m, 1H), 1.56 (m, 6H), 1.39 (m, 1H), 0.67 (m, 1H), 0.38 (m, 2H), 0.00 (m, 2H).

Example 30

Synthesis of Compound 32

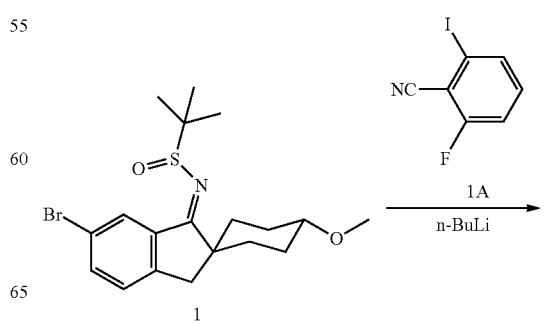

67

-continued

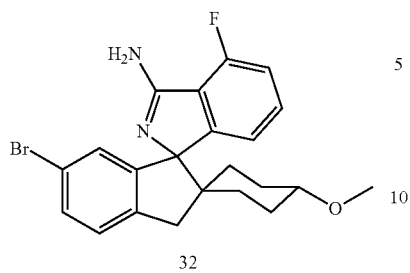

32

This was synthesized by method described in example 19, step 7.

LC-MS $t_R$=0.979 min in 2 min chromatography, MS (ESI) m/z 429/431 [M+H]$^+$.

$^1$H-NMR (CD$_3$OD 400 MHz): δ 7.48-7.50 (m, 1H), 7.39-7.41 (m, 1H), 7.31-7.33 (m, 1H), 7.22 (t, J=9.6 Hz, 1H), 7.04 (d, J=7.6 Hz, 1H), 6.87 (s, 1H), 3.30 (s, 3H), 3.12-3.17 (m, 2H), 3.03-3.05 (m, 1H), 1.89-1.97 (m, 2H), 1.55-1.68 (m, 2H), 1.25-1.42 (m, 3H), 0.98-1.01 (m, 1H).

Example 31

Synthesis of Compound 33

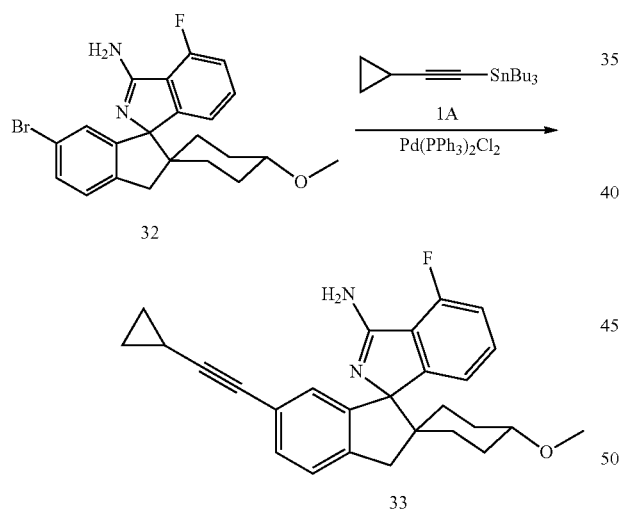

This was synthesized by method described in example 14. The crude product was purified by preparative TLC (CH$_2$Cl$_2$: MeOH=10:1) and preparative HPLC (acidic) to yield compound 33 (5.1 mg, 19%) as a white solid.

LC-MS $t_R$=0.929 min in 2 min chromatography, MS (ESI) m/z 415 [M+H]$^+$.

$^1$H-NMR (CD$_3$OD 400 MHz): δ 7.74-7.80 (m, 1H), 7.34-7.43 (m, 3H), 7.16 (d, J=7.6 Hz, 1H), 6.90 (s, 1H), 3.33 (s, 3H), 3.25-3.28 (s, 2H), 3.10 (m, 1H), 1.95-2.07 (m, 2H), 1.74-1.76 (m, 1H), 1.33-1.49 (m, 5H), 1.05-1.06 (m, 1H), 0.81-0.86 (m, 2H), 0.66-0.67 (m, 2H).

$^{19}$F-NMR (CD$_3$OD 400 MHz): δ −116.633.

68

Example 32

Synthesis of Compound 34

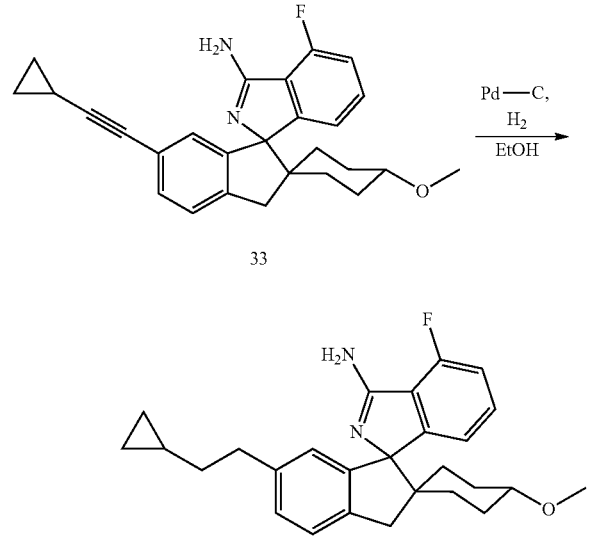

To a solution of compound 33 (13 mg, 0.03 mmol) in EtOH (5 mL) was added Pd/C (2 mg), the mixture was stirred under H$_2$ (30 PSI) at room temperature for 1 h. Then the mixture was filtered, the filtrate was concentrated in vacuo to give the residue, which was purified by preparative HPLC to give compound 34 (1.0 mg, 8%) as a white solid.

$^1$H NMR (CD$_3$OD 400 MHz): δ 7.81 (m, 1H), 7.44 (m, 2H), 7.27 (dd, J=7.6, 13.6 Hz, 2H), 6.82 (s, 1H) 3.67 (m, 1H), 3.16 (s, 3H), 3.13 (m, 2H), 2.70 (m, 2H), 2.03 (m, 2H), 1.81 (m, 1H), 1.48 (m, 5H), 1.36 (m, 2H), 0.66 (m, 1H), 0.38 (m, 2H), 0.00 (m, 2H).

LC-MS $t_R$=1.213 min in 2 min chromatography, MS (ESI) m/z 419 [M+H]$^+$.

Example 33

Synthesis of Compound 35

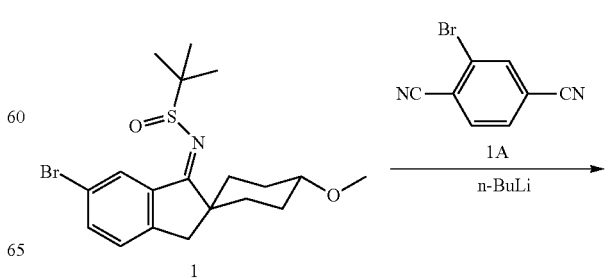

-continued

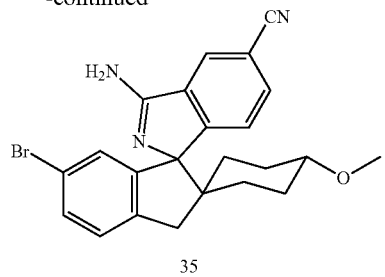

35

This was synthesized by method described in example 19, step 7. The crude product was purified by preparative TLC on silica gel (CH$_2$Cl$_2$:MeOH=10:1) and by HPLC (0.1% TFA as buffer) to give compound 35 (8.0 mg, 7%) as a white solid.

LC-MS (736-022-1Y): $t_R$=0.830 min in 2 min chromatography, MS (ESI) m/z 436 [M+H]$^+$.

$^1$H NMR (CD$_3$OD 400 MHz): δ 8.42 (s, 1H), 7.96 (dd, J=1.2, 8.0 Hz, 1H), 7.47 (d, J=8.0 Hz, 1H), 7.34 (d, J=8.0 Hz, 1H), 7.07 (d, J=9.2 Hz, 1H), 3.30 (m, 3H), 3.20 (m, 2H), 3.01 (m, 1H), 1.95 (m, 1H), 1.86 (m, 1H), 1.64 (m, 1H), 1.38 (m, 2H), 1.18 (m, 2H), 0.93 (m, 1H).

Example 34

Synthesis of Compound 36

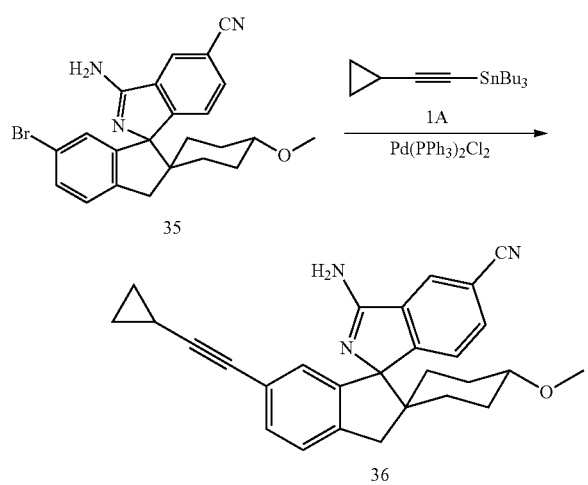

This was synthesized by method described in example 14. The crude product was purified by preparative TLC on silica gel (CH$_2$Cl$_2$:MeOH=10:1) and by preparative HPLC (0.1% TFA as buffer) to give compound 36 (7.3 mg, 9%) as a white solid.

LC-MS (736-056-1B): $t_R$=0.998 min in 2 min chromatography, MS (ESI) m/z 422 [M+H]$^+$.

$^1$H NMR (CD$_3$OD 400 MHz): δ 8.52 (s, 1H), 8.04 (dd, J=1.6, 8.0 Hz, 1H), 7.53 (d, J=8.0 Hz, 1H), 7.42 (d, J=8.0 Hz, 1H), 7.37 (dd, J=1.2, 8.0 Hz, 1H), 6.89 (s, 1H), 3.36 (m, 3H), 3.32 (m, 2H), 3.10 (m, 1H), 2.05 (m, 1H), 1.95 (m, 1H), 1.74 (m, 1H), 1.31-1.50 (m, 5H), 1.05 (m, 1H), 1.01 (m, 2H), 0.85 (m, 2H).

Example 35

Synthesis of Compound 37

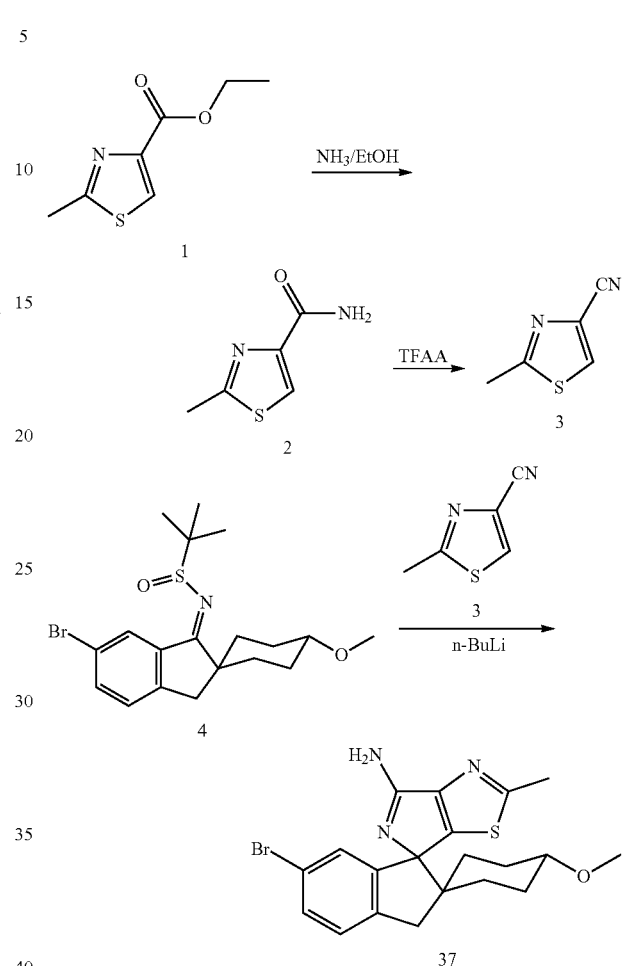

Step 1. Synthesis of Compound 2

A mixture of compound 1 (0.8 g, 4.68 mmol) and NH$_3$/EtOH (10 mL) was stirred at 60° C. for 6 days. Then the mixture was concentrated in vacuo to give the residue, which was purified by chromatography (petroleum:ethyl acetate=1:1) to give compound 2 (0.44 g, 77%) as a white solid.

Step 2. Synthesis of Compound 3

A mixture of compound 2 (340 mg, 2.79 mmol), TFAA (0.99 mL) and Et$_3$N (2.35 mL) in THF (10 mL) was stirred at room temperature for 3 h. Then the mixture was concentrated in vacuo to give the residue. The mixture was partitioned between H$_2$O (20 mL) and EtOAc (30 mL). The aqueous layer was extracted with EtOAc (3×30 mL). The combined organic layers were washed with brine (20 mL), dried over Na$_2$SO$_4$ and concentrated in vacuo to the crude product, which was purified by preparative TLC (petroleum ether:ethyl acetate=1:1) to give compound 3 (160 g, 55%) as a yellow solid.

Step 3. Synthesis of Compound 37

To a solution of compound 3 (100 mg, 0.89 mmol) in THF (2 mL) was added dropwise n-BuLi (0.392 mL, 0.98 mmol) at −78° C. slowly. After being stirred at −78° C. for 30 min, a solution of compound 4 (333 mg, 0.81 mmol) in THF (1 mL) was added at −78° C. slowly. After addition, the mixture was stirred at −78° C. for another 2 h, then was allowed to warm to room temperature and stirred overnight. The mixture was quenched with saturated aqueous NH$_4$Cl (3 mL). The aqueous layer was extracted with EtOAc (3×10 mL), and the combined organic layers were washed with brine (10 mL), dried over Na$_2$SO$_4$ and concentrated in vacuo to give the residue, which was purified by preparative TLC (CH$_2$Cl$_2$:MeOH=10:1) and preparative HPLC to give compound 37 (4.9 mg, 7%) as a yellow solid.

LC-MS $t_R$=0.951 min in 2 min chromatography, MS (ESI) m/z 432/434 [M+H]$^+$.

$^1$H-NMR (CD$_3$OD 400 MHz): δ 7.56 (d, J=2.0 Hz, 1H), 7.39 (d, J=8.4 Hz, 1H), 7.09 (s, 1H), 3.33 (s, 3H), 3.23-3.33 (m, 2H), 3.00-3.11 (m, 1H), 2.88 (s, 3H), 2.03-2.05 (m, 2H), 1.81 (m, 1H), 1.58 (m, 1H), 1.38-1.43 (m, 4H).

Example 36

Synthesis of Compound 38

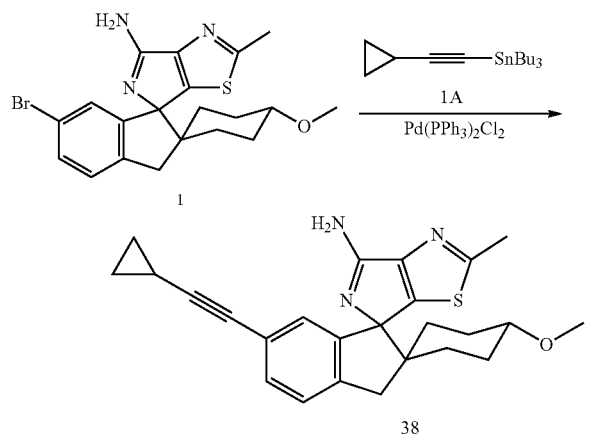

This was synthesized by method described in example 14. The crude product was purified by preparative TLC (CH$_2$Cl$_2$:MeOH=10:1) and preparative HPLC to yield compound 38 (3.3 mg, 18%) as a white solid.

LC-MS $t_R$=0.916 min in 2 min chromatography, MS (ESI) m/z 418 [M+H]$^+$.

$^1$H-NMR (CD$_3$OD 400 MHz): δ 7.37 (m, 2H), 6.82 (s, 1H), 3.33 (s, 3H), 3.23-3.33 (m, 2H), 3.00-3.11 (m, 1H), 2.88 (s, 3H), 2.03-2.05 (m, 2H), 1.81 (m, 1H), 1.58 (m, 1H), 1.38-1.43 (m, 5H), 0.84-0.88 (m, 2H), 0.67-0.70 (m, 2H).

Example 37

BACE Enzyme Assay

Inhibitory activity of compounds was assessed by a fluorescence quench assay of BACE activity using commercially available substrate HiLyte Fluor™488-Glu-Val-Asn-Leu-Asp-Ala-Glu-Phe-Lys-(QXL™ 520)-OH (AnaSpec, San Jose, Calif.) and truncated human beta-secretase (residues 1-458, His$_6$-tagged at the C-terminus) expressed in insect cells *D. melanogaster* S2 using a baculovirus expression system (Mallender et al., Characterization of recombinant, soluble beta-secretase from an insect cell expression system., Mol Pharmacol 59:619-26, 2001). The assay was performed at room temperature in 96-well white opaque Optiplates aque Optiplates (PerkinElmer, Waltham, Mass.) in a total volume of 200 μl of the incubation mixture containing 50 mM sodium acetate buffer, pH 4.5, 0.4 μM FRET substrate, 2.4 nM enzyme, 5% DMSO, and 0.05% Brij-35. The tested compounds were serially diluted in DMSO and pre-incubated with the substrate. The reaction was started by addition of enzyme, and the progress of the reaction was followed by measuring fluorescence with an excitation wavelength of 480 nm and an emission wavelength of 520 nm. Ten measurements were taken every 5-10 min, and the intensity of fluorescence was regressed against time in order to derive velocities of reaction in all 96 wells. These velocities were used for calculating percent inhibition using an uninhibited control containing 5% DMSO and a fully inhibited control incubations performed in the absence of enzyme. IC$_{50}$ values were calculated by fitting percent inhibition vs. inhibitor concentration into a four-parametric logistic model using XLFit software (IDBS, Guildford, UK).

Example 38

BACE Assay

For each compound being tested, the BACE activity was monitored in a fluorescence quenching assay (FRET) using the ectodomain of BACE (aa 1-454) fused to a myc-his tag and secreted from HEK293/BACE$_{ect.}$ cells into OptiMEM™ (Invitrogen) as enzyme source and a substrate peptide derived from the APP-Swedish mutation which possesses a Cy3-fluorophore at the N-terminus and a Cy5Q-quencher at the C-terminus (Cy3-SEVNLDAEFK-Cy5Q-NH2; Amersham). The substrate was dissolved at 1 mg/ml in DMSO.

The assay was performed in the presence of 5 μl OptiMEM (supernatant collected over 24 hours and cleared from cellular debris by centrifugation) containing the ectodomain of BACE, 25 μl water containing the desired concentration of test compound and 1% DMSO, 1 μM substrate peptide, 20 mM NaOAc, pH 4.4 and 0.04% Triton-X100 in a total assay volume of 50 μl in a 384 well plate. In general, 25 μl of compound dilution were given to the plate followed by the addition of 10 μl of BACE containing OptiMEM™ diluted 1:2 in water with 0.2% Triton X-100. The reaction was started with the addition of 15 μl substrate in NaOAc buffer. The reaction was incubated at 30° C. in a fluorimeter and the cleavage of the substrate was recorded as kinetic for 60 min. at ex: 530 nm, em: 590 nm Blank wells containing either no inhibitor or no enzyme were included on each plate.

The intensity of fluorescence was regressed against time in order to derive velocities of reaction in all 384 wells. These velocities were used for calculating percent inhibition using an uninhibited control containing 1% DMSO and a fully inhibited control incubations performed in the absence of enzyme. IC$_{50}$ values were calculated by fitting percent inhibition vs inhibitor concentration using standard software like GraphPadPrism.

Using this assay protocol, compound dilutions were either done using a Tecan Freedom EV0 (assay format A) or manually using multichannel pipettes (assay format B).

Example 39

BACE Activities of Compounds of the Invention

The BACE inhibitor activities of compounds of the invention were tested according to protocols described in Example 38 or Example 39, and are shown below:

| Compound No. | Structure/Example No. | IC$_{50}$ |
|---|---|---|
| 1 | 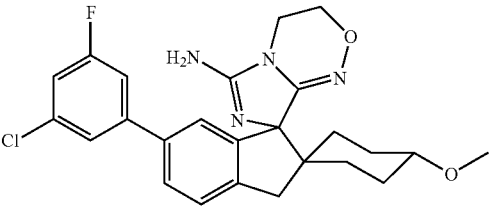<br>Ex. 1 | 1.1[a] |
| 2 | 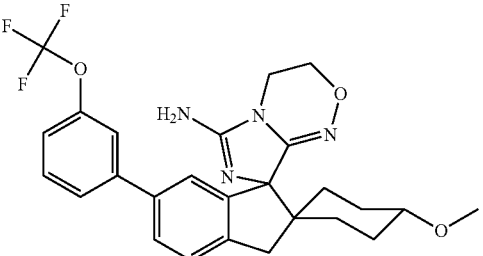<br>Ex. 2 | 2.19[a] |
| 3 | 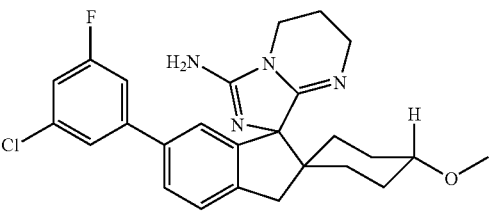<br>Ex. 3 | 9.5[a] |
| 4 | 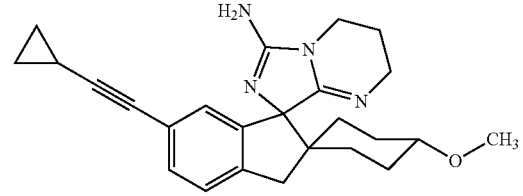<br>Ex. 4 | 29[a] |
| 5 | 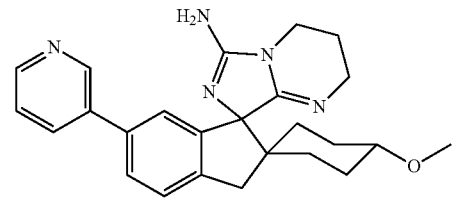<br>Ex. 5 | 14[a] |
| 6 | 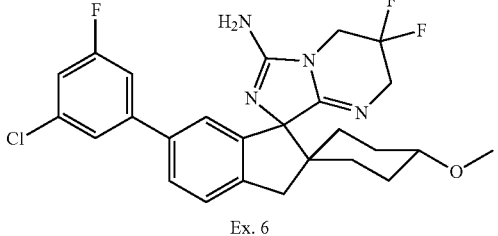<br>Ex. 6 | 5[a] |

-continued
| Compound No. | Structure/Example No. | IC$_{50}$ |
|---|---|---|
| 7 | 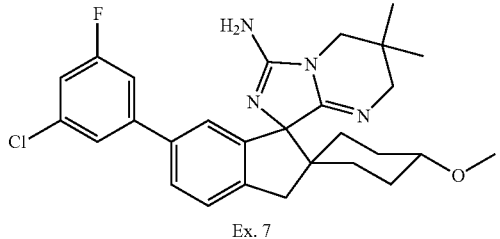 [SMILES: COC1CCC2(CC1)Cc1ccc(-c3cc(F)cc(Cl)c3)cc1C21N=C(N)N2CC(C)(C)CN=C21]<br>Ex. 7 | 2816[a] |
| 8 | 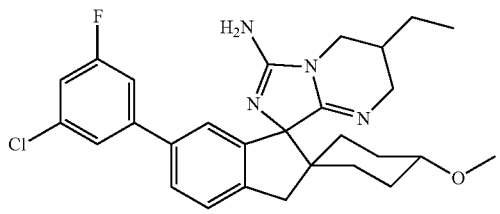<br>Ex. 8 | 7.5[a] |
| 9 | 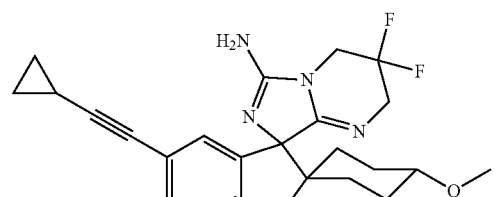<br>Ex. 9 | 16.3[a] |
| 10 | 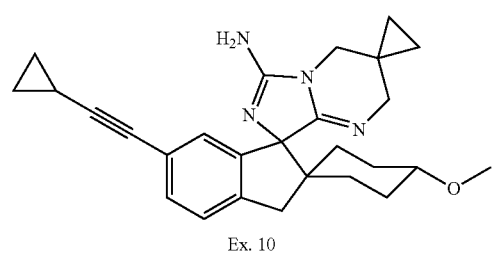 [SMILES: COC1CCC2(CC1)Cc1ccc(C#CC3CC3)cc1C21N=C(N)N2CC3(CC3)CN=C21]<br>Ex. 10 | 733[a] |
| 11 | 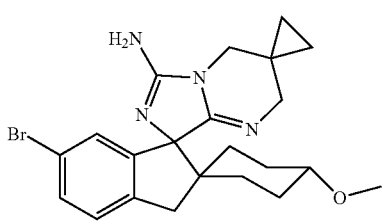<br>Ex. 11 | 242[a] |

-continued
| Compound No. | Structure/Example No. | IC$_{50}$ |
|---|---|---|
| 12 | 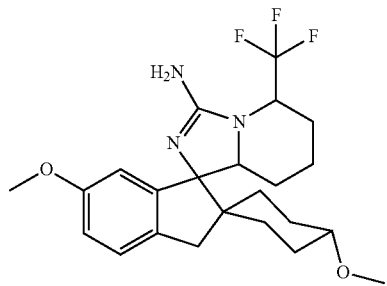<br>Ex. 12 | 50000[b] |
| 13 | 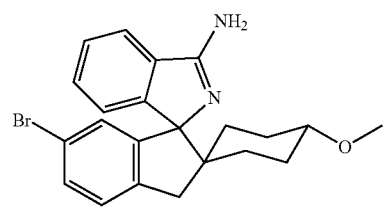<br>Ex. 13 | 55[a] |
| 14 | 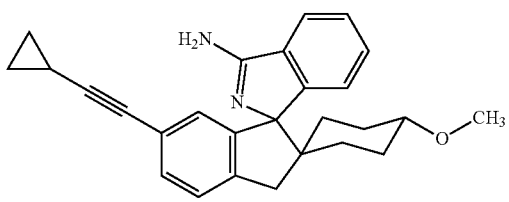<br>Ex. 14 | 14.5[b] |
| 15 | 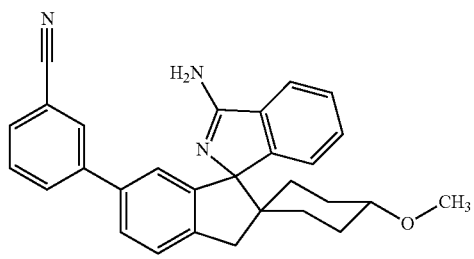<br>Ex. 15 | 6[b] |
| 16 | 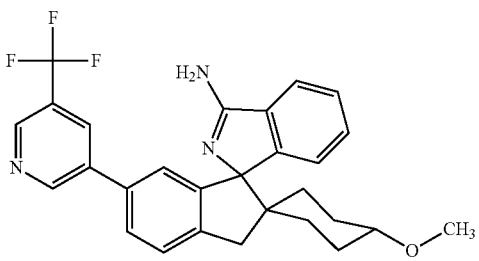<br>Ex. 16 | 47[b] |

-continued
| Compound No. | Structure/Example No. | IC$_{50}$ |
|---|---|---|
| 17 | 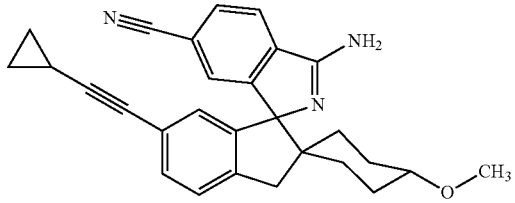<br>Ex. 17 | 3.6[b] |
| 18 | 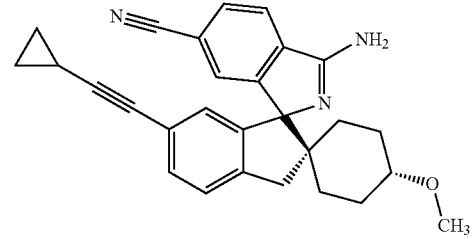<br>Ex. 17 | 4.6[b] |
| 19 | 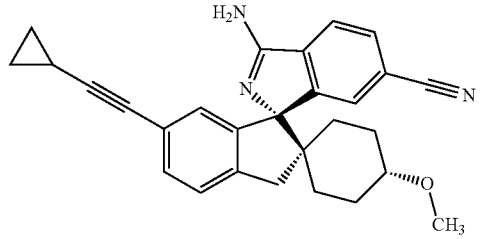<br>Ex. 17 | 5.9[b] |
| 20 | 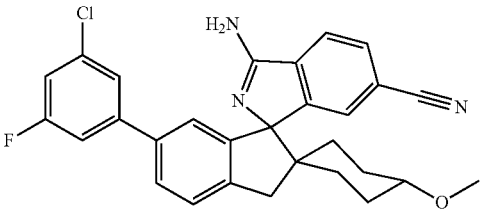<br>Ex. 18 | 20[b] |
| 21 | 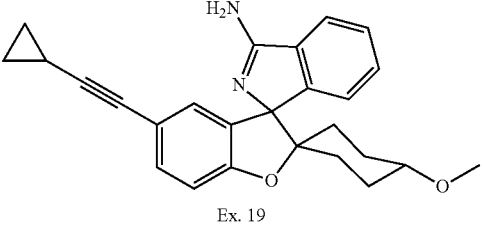 [SMILES: COC1CCC2(CC1)Oc1ccc(C#CC3CC3)cc1C21N=C(N)c2ccccc21]<br>Ex. 19 | 74[b] |
| 22 | 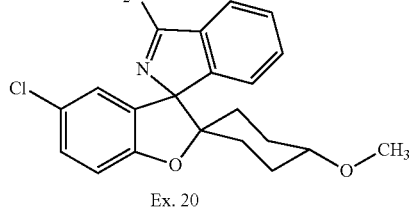<br>Ex. 20 | 413[b] |

-continued
| Compound No. | Structure/Example No. | IC$_{50}$ |
|---|---|---|
| 23 | 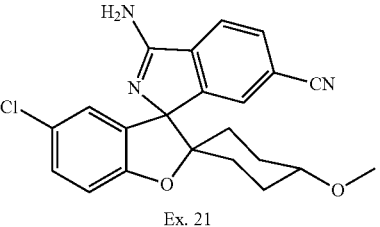 [SMILES: COC1CCC2(CC1)Oc1ccc(Cl)cc1C21N=C(N)c2ccc(C#N)cc21] Ex. 21 | 83[b] |
| 24 | 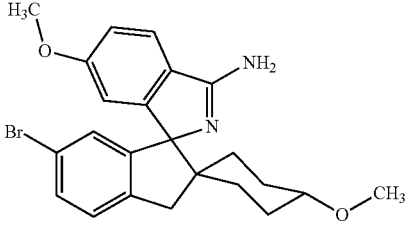 Ex. 22 | 1428[b] |
| 25 | 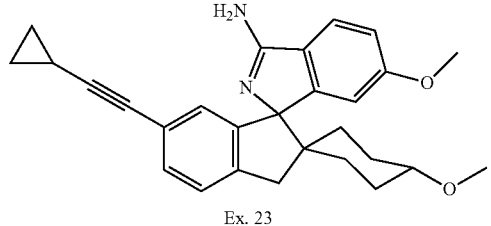 [SMILES: COc1ccc2c(c1)C1(N=C2N)c2cc(C#CC3CC3)ccc2CC12CCC(OC)CC2] Ex. 23 | 35[b] |
| 26 | 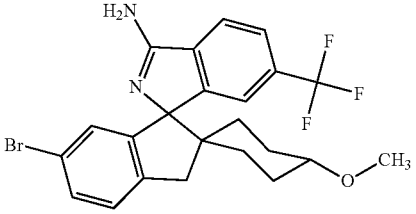 Ex. 24 | 65[b] |
| 27 | 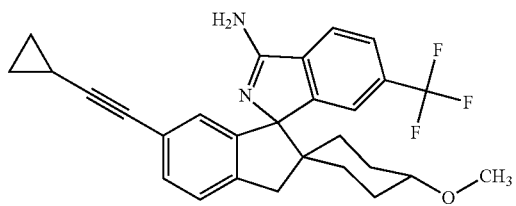 Ex. 25 | 6.5[b] |
| 28 | 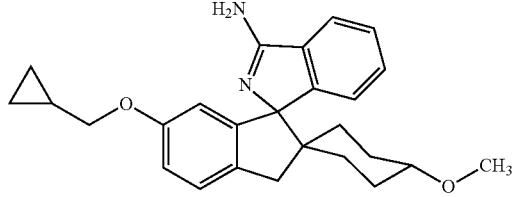 Ex. 26 | 13[b] |

-continued
| Compound No. | Structure/Example No. | IC$_{50}$ |
|---|---|---|
| 29 | 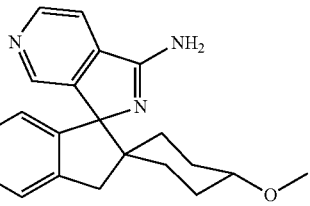<br>Ex. 27 | N/A |
| 30 | 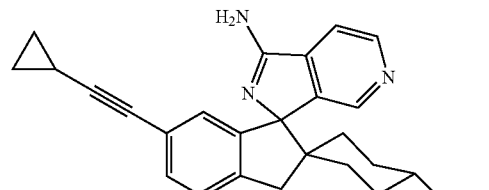<br>Ex. 28 | N/A |
| 31 | 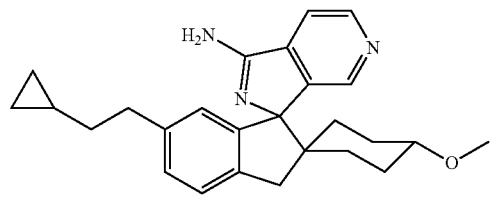<br>Ex. 29 | N/A |
| 32 | 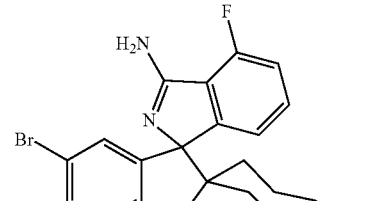<br>Ex. 30 | N/A |
| 33 | 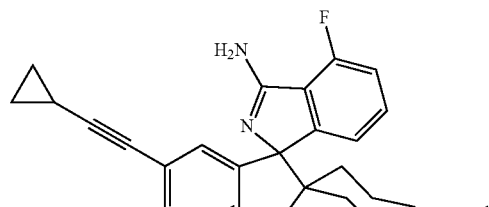<br>Ex. 31 | 5[b] |
| 34 | 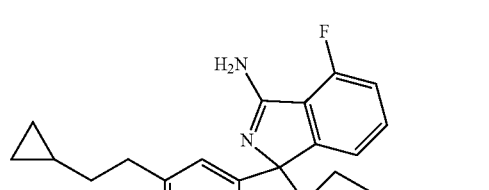<br>Ex. 32 | 13[b] |

85
-continued

| Compound No. | Structure/Example No. | IC$_{50}$ |
|---|---|---|
| 35 | 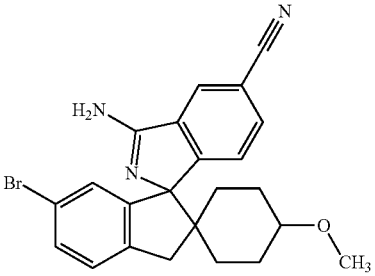  Ex. 33 | 24.8[b] |
| 36 | 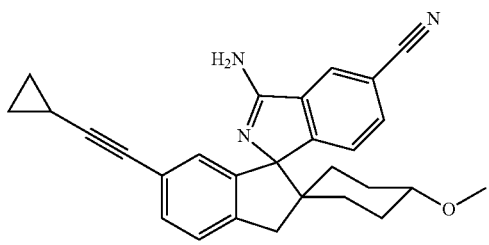  Ex. 34 | 4.09[b] |
| 37 | 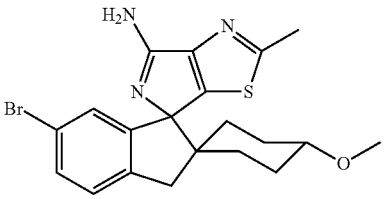  Ex. 35 | N/A |
| 38 | 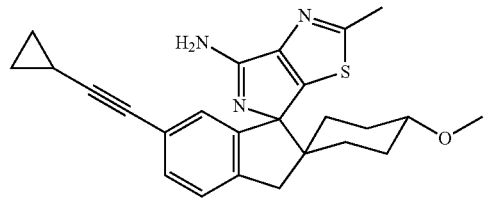  Ex. 36 | N/A |

[a]IC$_{50}$ values were determined according to protocols described in Example 37.
[b]IC$_{50}$ values were determined according to protocols described in Example 38.

What is claimed is:

1. A compound represented by the following structural formula:

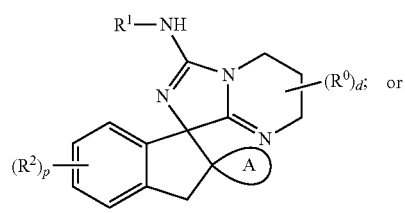 (Va)

or

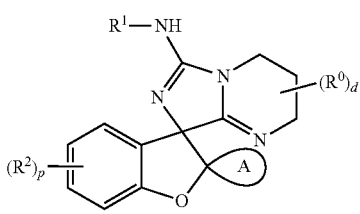 (Vb)

or a pharmaceutically acceptable salt thereof, wherein:
each $R^0$ is independently selected from —H, —CN, —NO$_2$, halogen, —OR$^5$, —NR$^6$R$^7$, —S(O)$_r$R$^5$, —NR$^{11}$S(O)$_2$R$^5$, —S(O)$_2$NR$^{12}$R$^{13}$, —C(=O)OR$^5$, —OC(=O)R$^5$, —C(=S)OR$^5$, —OC(=S)R$^5$, —C(=O)NR$^{12}$R$^{13}$, —NR$^{11}$C(=O)R$^5$, —C(=S)NR$^{12}$R$^{13}$, —NR$^{11}$C(=S)R$^5$, —NR$^{11}$(C=O)OR$^5$, —O(C=O)NR$^{12}$R$^{13}$, —NR$^{11}$(C=S)OR$^5$, —O(C=S)NR$^{12}$R$^{13}$, —NR$^{11}$(C=O)NR$^{12}$R$^{13}$, —NR$^{11}$(C=S)NR$^{12}$R$^{13}$, —C(=O)R$^5$, —C(=S)R$^5$, (C$_1$-C$_6$)alkyl, (C$_3$-C$_4$)cycloalkyl and (C$_3$-C$_4$)cycloalkyl(C$_1$-C$_3$)alkyl and wherein each (C$_1$-C$_6$)alkyl and (C$_1$-C$_3$)alkoxy represented by R$^0$ are optionally substituted with 1 to 5 substituents independently selected from the group consisting of halogen, —CN, (C$_1$-C$_6$)alkyl, halo(C$_1$-C$_6$)alkyl, (C$_1$-C$_3$)alkoxy(C$_1$-C$_6$)alkyl, (C$_1$-C$_3$)alkoxy, and —NR$^6$R$^7$, or two R$^0$ together with the ring carbon atom to which they are attached form a (C$_3$-C$_6$)cycloalkyl, optionally substituted with halogen, —CN, (C$_1$-C$_6$)alkyl, halo(C$_1$-C$_6$)alkyl, (C$_1$-C$_3$)alkoxy(C$_1$-C$_6$)alkyl, (C$_1$-C$_3$)alkoxy, and —NR$^6$R$^7$;

R$^1$ is —H, —OH, —(C$_1$-C$_4$)alkoxy, (C$_1$-C$_6$)alkyl, aryl(C$_1$-C$_6$)alkyl, or heteroaryl(C$_1$-C$_6$)alkyl, wherein each alkyl, aryl and heteroaryl is optionally substituted with 1 to 5 substituents independently selected from halogen, —CN, —OH, (C$_1$-C$_4$)alkyl, halo(C$_1$-C$_4$)alkyl, (C$_1$-C$_3$)alkoxy and halo(C$_1$-C$_3$)alkoxy;

each R$^2$ is independently selected from a) —H, halogen, —CN, —NO$_2$, —OR$^5$, —NR$^6$R$^7$, —S(O)$_i$R$^5$, —NR$^{11}$S(O)$_2$R$^5$, —S(O)$_2$NR$^{12}$R$^{13}$, —C(=O)OR$^5$, —OC(=O)R$^5$, —C(=S)OR$^5$, —OC(=S)R$^5$, —C(=O)NR$^{12}$R$^{13}$, —NR$^{11}$C(=O)R$^5$, —C(=S)NR$^{12}$R$^{13}$, —NR$^{11}$C(=S)R$^5$, —NR$^{11}$(C=O)OR$^5$, —O(C=O)NR$^{12}$R$^{13}$, —NR$^{11}$(C=S)OR$^5$, —O(C=S)NR$^{12}$R$^{13}$, —NR$^{11}$(C=O)NR$^{12}$R$^{13}$, —NR$^{11}$(C=S)NR$^{12}$R$^{13}$, —C(=O)R$^5$, —C(=S)R$^5$; and b) (C$_1$-C$_6$)alkyl, (C$_2$-C$_6$)alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkynyl, (C$_4$-C$_8$)cycloalkenyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkynyl, aryl, aryl(C$_1$-C$_6$)alkyl, aryl(C$_2$-C$_6$)alkynyl, heteroaryl, heteroaryl(C$_1$-C$_6$)alkyl, and heteroaryl(C$_2$-C$_6$)alkynyl, wherein each (C$_1$-C$_6$)alkyl, (C$_2$-C$_6$)alkenyl, (C$_2$-C$_6$)alkynyl, (C$_3$-C$_8$)cycloalkyl, (C$_3$-C$_8$)cycloalkyl(C$_1$-C$_6$)alkyl, (C$_3$-C$_8$)cycloalkyl(C$_2$-C$_6$)alkynyl, (C$_4$-C$_8$)cycloalkenyl, (C$_3$-C$_9$)heterocycloalkyl, (C$_3$-C$_9$)heterocycloalkyl(C$_1$-C$_6$)alkyl, (C$_3$-C$_9$)heterocycloalkyl(C$_2$-C$_6$)alkynyl, aryl, aryl(C$_1$-C$_6$)alkyl, aryl(C$_2$-C$_6$)alkynyl, heteroaryl, heteroaryl(C$_1$-C$_6$)alkyl, and heteroaryl(C$_2$-C$_6$)alkynyl is optionally substituted with 1 to 5 substituents independently selected from the group consisting of halogen, —CN, —NO$_2$, —OR$^5$, —NR$^6$R$^7$, —S(O)$_i$R$^5$, —NR$^{11}$S(O)$_2$R$^5$, —S(O)$_2$NR$^{12}$R$^{13}$, —C(=O)OR$^5$, —OC(=O)R$^5$, —C(=S)OR$^5$, —OC(=S)R$^5$, —C(=O)NR$^{12}$R$^{13}$, —NR$^{11}$C(=O)R$^5$, —C(=S)NR$^{12}$R$^{13}$, —NR$^{11}$C(=S)R$^5$, —NR$^{11}$(C=O)OR$^5$, —O(C=O)NR$^{12}$R$^{13}$, —NR$^{11}$(C=S)OR$^5$, —O(C=S)NR$^{12}$R$^{13}$, —NR$^{11}$(C=O)NR$^{12}$R$^{13}$, —NR$^{11}$(C=S)NR$^{12}$R$^{13}$, —C(=O)R$^5$, —C(=S)R$^5$, (C$_1$-C$_6$)alkyl, (C$_2$-C$_6$)alkynyl, (C$_3$-C$_8$)cycloalkyl, (C$_4$-C$_8$)cycloalkenyl, (C$_3$-C$_9$)heterocycloalkyl, (C$_2$-C$_6$)alkenyl, halo(C$_1$-C$_6$)alkyl, —(C$_1$-C$_6$)alkylene-NR$^{11}$—SO$_2$—(C$_1$-C$_3$)alkyl, hydroxy(C$_1$-C$_6$)alkyl, cyano(C$_1$-C$_6$)alkyl, —(C$_1$-C$_6$)alkylene-NR$^{11}$—C(=O)—(C$_1$-C$_3$)alkyl, (C$_1$-C$_3$)alkoxy, halo(C$_1$-C$_3$)alkoxy, (C$_1$-C$_6$)alkoxy(C$_1$-C$_3$)alkyl, aryl, and heteroaryl, wherein the cycloalkyl, heterocycloalkyl, aryl and heteroaryl groups in the substituents on the groups represented by R$_2$ are each optionally substituted with 1 to 3 substituents independently selected from halogen, —CN, (C$_1$-C$_6$)alkyl, halo(C$_1$-C$_6$)alkyl, (C$_1$-C$_3$)alkoxy, halo(C$_1$-C$_3$)alkoxy and (C$_1$-C$_3$)alkoxy(C$_1$-C$_6$)alkyl;

R$^5$ is selected from the group consisting of —H, (C$_1$-C$_3$)alkyl, halo(C$_1$-C$_3$)alkyl, (C$_1$-C$_3$)alkoxy(C$_1$-C$_3$)alkyl, (C$_3$-C$_6$)cycloalkyl, (C$_3$-C$_6$)cycloalkyl(C$_1$-C$_3$)alkyl and phenyl optionally substituted with halogen, —CN, —NO$_2$, (C$_1$-C$_3$)alkyl, halo(C$_1$-C$_3$)alkyl or (C$_1$-C$_3$)alkoxy(C$_1$-C$_3$)alkyl;

R$^6$ is —H or (C$_1$-C$_3$)alkyl;

R$^7$ is —H, (C$_1$-C$_3$)alkyl, halo(C$_1$-C$_3$)alkyl, (C$_3$-C$_6$)cycloalkyl, (C$_3$-C$_6$)cycloalkyl(C$_1$-C$_3$)alkyl or (C$_1$-C$_3$)alkoxy(C$_1$-C$_3$)alkyl;

Ring A is a 3-9 membered cycloalkyl optionally substituted with 1 to 4 substituents independently selected from the group consisting of halogen, —CN, —OR$^5$, —NR$^6$R$^7$, —S(O)$_i$R$^5$, —NR$^{11}$S(=O)$_2$R$^5$, —C(=O)OR$^5$, —C(=O)NR$^{12}$R$^{13}$, —NR$^{11}$C(=O)R$^5$, —C(=S)NR$^{12}$R$^{13}$, —C(=O)R$^5$, (C$_1$-C$_6$)alkyl, (C$_2$-C$_6$)alkenyl, aryl, aryl(C$_1$-C$_6$)alkyl, heteroaryl and heteroaryl(C$_1$-C$_6$)alkyl, wherein each of the (C$_1$-C$_6$)alkyl, (C$_2$-C$_6$)alkenyl, aryl, aryl(C$_1$-C$_6$)alkyl, heteroaryl and heteroaryl(C$_1$-C$_6$)alkyl substituents on Ring A is optionally substituted with 1 to 5 substituents independently selected from the group consisting of (C$_1$-C$_6$)alkyl, halogen, —CN, —OH, —NR$^{11}$SO$_2$(C$_1$-C$_3$)alkyl, —NR$^{11}$C(=O)—(C$_1$-C$_3$)alkyl, (C$_1$-C$_6$)alkyl, halo(C$_1$-C$_6$)alkyl, (C$_1$-C$_3$)alkoxy and (C$_1$-C$_3$)alkoxy(C$_1$-C$_6$)alkyl, and wherein Ring A is optionally fused to a phenyl group optionally substituted with 1 to 5 substituents independently selected from the group consisting of (C$_1$-C$_6$)alkyl, halogen, —CN, —OH, —NR$^{11}$SO$_2$(C$_1$-C$_3$)alkyl, —NR$^{11}$C(=O)—(C$_1$-C$_3$)alkyl, (C$_1$-C$_6$)alkyl, halo(C$_1$-C$_6$)alkyl, (C$_1$-C$_3$)alkoxy and (C$_1$-C$_3$)alkoxy(C$_1$-C$_6$)alkyl;

R$^{11}$ is —H or (C$_1$-C$_3$)alkyl;

R$^{12}$ is —H or (C$_1$-C$_3$)alkyl;

R$^{13}$ is —H, (C$_1$-C$_3$)alkyl, halo(C$_1$-C$_3$)alkyl, (C$_3$-C$_6$)cycloalkyl(C$_1$-C$_3$)alkyl or (C$_1$-C$_3$)alkoxy(C$_1$-C$_3$)alkyl;

d is an integer from 1 to 6;

i is 0, 1 or 2; and p is 1, 2, 3 or 4.

2. The compound of claim 1, wherein:

R$^1$ is a —H or a (C$_1$-C$_3$)alkyl;

each R$^2$ is independently selected from the group consisting of —H, halogen, —CN, —NO$_2$, —OR$^5$, —C(=O)NR$^{12}$R$^{13}$, (C$_1$-C$_6$)alkyl, (C$_2$-C$_6$)alkenyl, (C$_2$-C$_6$)alkynyl, phenyl(C$_2$-C$_6$)alkynyl, (C$_3$-C$_8$)cycloalkyl, (C$_4$-C$_8$)cycloalkenyl, phenyl, pyridyl, thiazolyl, pyridazinyl, pyridazinone, pyridinone, thiophenyl, pyrrolyl, pyrimidinyl, pyrazinyl, indolyl, pyrrolidinyl, piperazinyl and morpholinyl, each of the (C$_1$-C$_6$)alkyl, (C$_2$-C$_6$)alkenyl, (C$_2$-C$_6$)alkynyl, phenyl(C$_2$-C$_6$)alkynyl, (C$_3$-C$_8$)cycloalkyl, (C$_4$-C$_8$)cycloalkenyl, phenyl, pyridinyl, thiazolyl, pyridazinyl, pyridazinone, pyridinone, thiophenyl, pyrrolyl, pyrimidinyl, pyrazinyl, indolyl, pyrrolidinyl, piperazinyl and morpholinyl is optionally substituted with 1 to 3 substituents independently selected from the group consisting of halogen, —OH, —CN, —NO$_2$, (C$_1$-C$_6$)alkyl, (C$_2$-C$_6$)alkynyl, halo(C$_1$-C$_6$)alkyl, (C$_3$-C$_8$)cycloalkyl, (C$_1$-C$_3$)alkoxy, halo(C$_1$-C$_3$)alkoxy, (C$_1$-C$_3$)alkoxy(C$_1$-C$_6$)alkyl, —NR$^6$R$^7$ and —SO$_2$R$^5$; and each R$^0$, when present, is independently selected from the group consisting of —H, halogen, —CN, (C$_1$-C$_6$)alkyl, halo(C$_1$-C$_6$)alkyl, (C$_1$-C$_3$)alkoxy and —NR$^6$R$^7$, or two R$^0$, taken together to the carbon atom to which they are attached, form a (C$_3$-C$_6$)cycloalkyl.

3. The compound of claim 2, wherein:
each $R^2$ is independently selected from —Br, —Cl, —CN, —$OR^5$, ($C_1$-$C_6$)alkyl, ($C_2$-$C_6$)alkynyl, phenyl and pyridinyl, wherein each of the ($C_1$-$C_6$)alkyl, ($C_2$-$C_6$)alkynyl, phenyl and pyridinyl is optionally substituted with 1 to 3 substituents independently selected from —F, —Cl, —Br, —CN, ($C_3$-$C_6$)cycloalkyl, ($C_1$-$C_3$)alkyl, halo($C_1$-$C_3$)alkyl, ($C_1$-$C_3$)alkoxy and halo($C_1$-$C_3$)alkoxy.

4. The compound of claim 3, wherein:
$R^1$ is —H;
each $R^2$ is independently selected from the group consisting of —Br, —Cl, —CN, cyclopropylethyl, cyclopropylethynyl, cyclopropylmethoxy, 5-trifluoromethyl-2-pyridyl, 2-pyridyl, 3-chloro-5-fluorophenyl, 3-cyanophenyl, 3-trifluoromethoxyphenyl and methoxy; and
each $R^0$, when present, is independently selected from the group consisting of —H, —F, —CN, -Me, -Et, —OMe, —$CF_3$ and —$NH_2$, or two $R^0$ together with the carbon atom to which they are attached form a cyclopropyl ring.

5. The compound of claim 4, wherein:
$R^5$ is selected from the group consisting of —H, -Me, —$CF_3$ and cyclopropylmethyl; and
$R^6$, $R^7$, $R^{11}$, $R^{12}$ and $R^{13}$ are all —H.

6. A pharmaceutical composition comprising a pharmaceutically acceptable carrier or diluent and a compound of claim 1 or a pharmaceutically acceptable salt thereof.

7. A method of treating a BACE mediated disorder in a subject comprising administering to the subject an effective amount of a compound of claim 1 or a pharmaceutically acceptable salt thereof, wherein the BACE mediated disorder is selected from the group consisting of Alzheimer's disease, Down's Syndrome, cerebral amyloid angiopathy, glaucoma, HCHWA-D, cognitive impairment and cognitive decline.

8. The method of claim 7, wherein the disorder is Alzheimer's disease.

9. The method of claim 7, wherein the disorder is glaucoma.

10. A compound represented by any one of the following structural formulas:

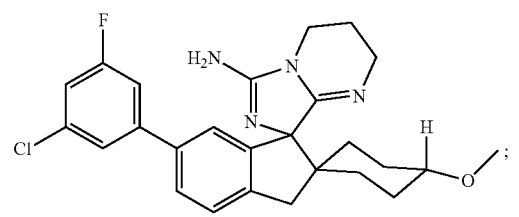

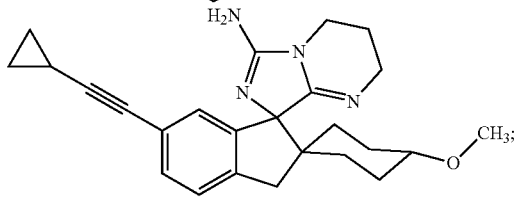

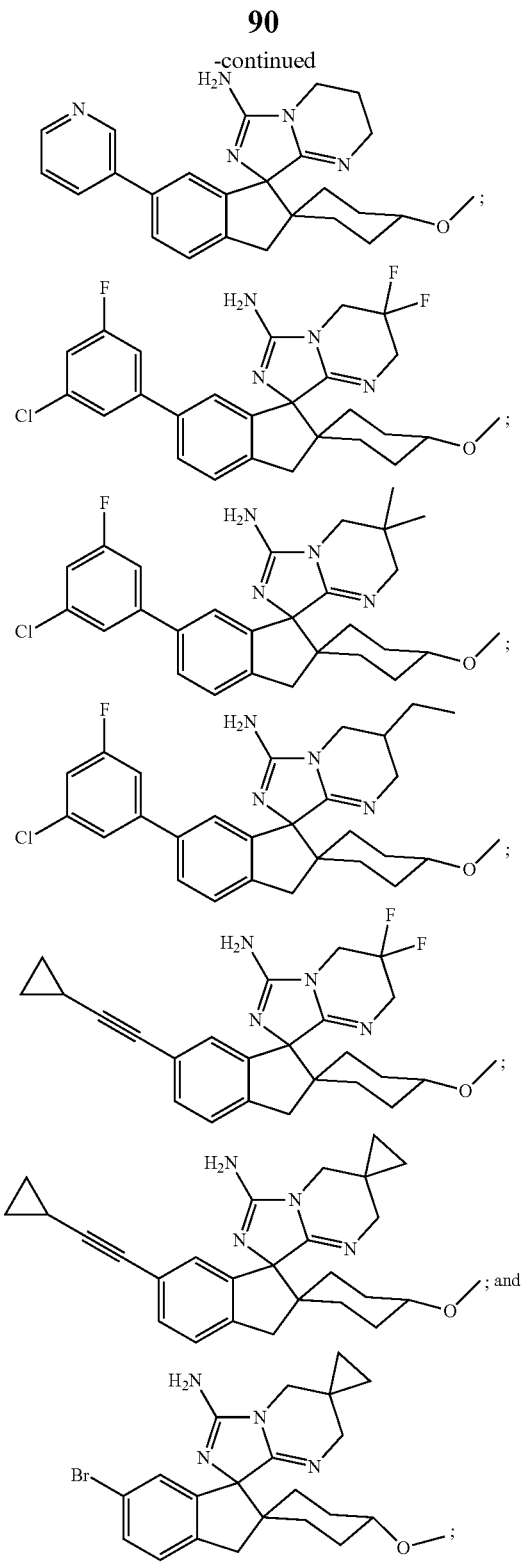

or a pharmaceutically acceptable salt thereof.

* * * * *